US012446905B2

(12) United States Patent
Cannata et al.

(10) Patent No.: US 12,446,905 B2
(45) Date of Patent: Oct. 21, 2025

(54) HISTOTRIPSY SYSTEMS AND ASSOCIATED METHODS INCLUDING USER INTERFACES AND WORKFLOWS FOR TREATMENT PLANNING AND THERAPY

(71) Applicant: HistoSonics, Inc., Plymouth, MN (US)

(72) Inventors: Jonathan M. Cannata, Ann Arbor, MI (US); Alexander P. Duryea, Ann Arbor, MI (US); Ryan M. Miller, Saline, MI (US); Zeljko Mladenovic, Orefield, PA (US); Joshua Stopek, Minneapolis, MN (US); Erin-Anne Lemieux, Mont Vernon, NH (US); Carolyn M. Turner, Minneapolis, MN (US); Carol L. Shaffer, Minnetrista, MN (US)

(73) Assignee: HistoSonics, Inc., Plymouth, MN (US)

( * ) Notice: Subject to any disclaimer, the term of this patent is extended or adjusted under 35 U.S.C. 154(b) by 0 days.

(21) Appl. No.: 18/642,529

(22) Filed: Apr. 22, 2024

(65) Prior Publication Data

US 2024/0350153 A1 Oct. 24, 2024

Related U.S. Application Data

(60) Provisional application No. 63/497,277, filed on Apr. 20, 2023.

(51) Int. Cl.
*A61B 17/22* (2006.01)
*A61B 8/00* (2006.01)
(Continued)

(52) U.S. Cl.
CPC ...... *A61B 17/22004* (2013.01); *A61B 8/4218* (2013.01); *A61B 8/461* (2013.01);
(Continued)

(58) Field of Classification Search
CPC . A61B 17/22004; A61B 8/4218; A61B 8/461; A61B 8/469; A61B 34/25;
(Continued)

(56) References Cited

U.S. PATENT DOCUMENTS

| | | | |
|---|---|---|---|
| 3,243,497 | A | 3/1966 | Kendall et al. |
| 3,679,021 | A | 7/1972 | Goldberg et al. |

(Continued)

FOREIGN PATENT DOCUMENTS

| | | | |
|---|---|---|---|
| AU | 2017222925 | B2 | 11/2021 |
| AU | 2023231624 | A1 | 9/2024 |

(Continued)

OTHER PUBLICATIONS

Ma et al.; Acoustic focusing and imaging via phononic crystal and acoustic metamaterials; Journal of Applied Physics; 131(1); doi:10.10653/5.0074503; 29 pages; Jan. 5, 2022.

(Continued)

*Primary Examiner* — Sanjay Cattungal
(74) *Attorney, Agent, or Firm* — Shay Glenn LLP

(57) ABSTRACT

A system and method, including an ultrasound imaging transducer, an ultrasound therapy transducer, a robotic arm configured to orient the ultrasound imaging transducer and the ultrasound therapy transducer about a patient, a display connected to imaging transducer, and a memory, storing instructions that when executed by a processor receive ultrasound images from the imaging transducer, present ultrasound images, receive an input to alter a shape of a contour line, present the contour line, receive an input of a size of a margin around the treatment area, present the margin, determine end points at locations where X, Y, and Z axes bisect the contour line in an XZ plane and a YZ plane, drive the ultrasound therapy transducer to a location where a focal point of the ultrasound therapy transducer is at the (Continued)

end point, and determining whether a resistance to movement exceeds a threshold.

20 Claims, 73 Drawing Sheets

(51) Int. Cl.
*A61B 34/00* (2016.01)
*A61B 34/30* (2016.01)
*A61B 17/00* (2006.01)
*A61B 34/10* (2016.01)

(52) U.S. Cl.
CPC .............. *A61B 8/469* (2013.01); *A61B 34/25* (2016.02); *A61B 34/30* (2016.02); *A61B 2017/00106* (2013.01); *A61B 2017/22008* (2013.01); *A61B 2034/107* (2016.02)

(58) Field of Classification Search
CPC .......... A61B 34/30; A61B 2017/00106; A61B 2017/22008; A61B 2034/107; A61B 2034/105; A61B 34/10; A61B 34/32; A61B 2017/00725; A61B 2034/252; A61B 2034/256; A61B 2090/378; A61N 7/00; A61N 2007/0039; A61N 2007/0086
See application file for complete search history.

(56) References Cited

U.S. PATENT DOCUMENTS 3,693,415 A 9/1972 Whittington
3,879,699 A 4/1975 Pepper
4,016,749 A 4/1977 Wachter
4,024,501 A 5/1977 Herring et al.
4,051,394 A 9/1977 Tieden
4,114,457 A 9/1978 Thun
4,117,446 A 9/1978 Alais
4,266,747 A 5/1981 Souder, Jr. et al.
4,269,174 A 5/1981 Adair
4,277,367 A 7/1981 Madsen et al.
4,351,038 A 9/1982 Alais
4,406,153 A 9/1983 Ophir et al.
4,440,025 A 4/1984 Hayakawa et al.
4,447,031 A 5/1984 Souder, Jr. et al.
4,453,408 A 6/1984 Clayman
4,483,343 A 11/1984 Beyer et al.
4,483,345 A 11/1984 Miwa
4,548,374 A 10/1985 Thompson et al.
4,549,533 A 10/1985 Cain et al.
4,550,606 A 11/1985 Drost
4,551,794 A 11/1985 Sandell
4,575,330 A 3/1986 Hull
4,622,972 A 11/1986 Giebeler, Jr.
4,625,731 A 12/1986 Quedens et al.
4,641,378 A 2/1987 McConnell et al.
4,669,483 A 6/1987 Hepp et al.
4,689,986 A 9/1987 Carson et al.
4,757,820 A 7/1988 Itoh
4,791,915 A 12/1988 Barsotti et al.
4,819,621 A 4/1989 Ueberle et al.
4,829,491 A 5/1989 Saugeon et al.
4,856,107 A 8/1989 Dory
4,865,042 A 9/1989 Umemura et al.
4,888,746 A 12/1989 Wurster et al.
4,890,267 A 12/1989 Rudolph
4,922,917 A 5/1990 Dory
4,928,672 A 5/1990 Grasser et al.
4,938,217 A 7/1990 Lele
4,957,099 A 9/1990 Hassler
4,973,980 A 11/1990 Howkins et al.
4,984,575 A 1/1991 Uchiyama et al.
4,991,151 A 2/1991 Dory
4,995,012 A 2/1991 Dory
RE33,590 E 5/1991 Dory
5,014,686 A 5/1991 Schafer
5,065,751 A 11/1991 Wolf
5,078,140 A 1/1992 Kwoh
5,080,101 A 1/1992 Dory
5,080,102 A 1/1992 Dory
5,091,893 A 2/1992 Smith et al.
5,092,336 A 3/1992 Fink
5,097,709 A 3/1992 Masuzawa et al.
5,111,822 A 5/1992 Dory
5,143,073 A 9/1992 Dory
5,143,074 A 9/1992 Dory
5,150,711 A 9/1992 Dory
5,158,070 A 10/1992 Dory
5,158,071 A 10/1992 Umemura et al.
5,163,421 A 11/1992 Bernstein et al.
5,165,412 A 11/1992 Okazaki
5,174,294 A 12/1992 Saito et al.
5,195,509 A 3/1993 Rentschler et al.
5,209,221 A 5/1993 Riedlinger
5,215,680 A 6/1993 D'Arrigo
5,219,401 A 6/1993 Cathignol et al.
5,222,806 A 6/1993 Roberts
5,230,340 A 7/1993 Rhyne
5,295,484 A 3/1994 Marcus et al.
5,316,000 A 5/1994 Chapelon et al.
5,354,258 A 10/1994 Dory
5,380,411 A 1/1995 Schlief
5,393,296 A 2/1995 Rattner
5,409,002 A 4/1995 Pell
5,431,621 A 7/1995 Dory
5,435,311 A 7/1995 Umemura et al.
5,443,069 A 8/1995 Schaetzle
5,450,305 A 9/1995 Boys et al.
5,469,852 A 11/1995 Nakamura et al.
5,474,071 A 12/1995 Chapelon et al.
5,474,531 A 12/1995 Carter
5,490,051 A 2/1996 Messana
5,492,126 A 2/1996 Hennige et al.
5,501,655 A 3/1996 Rolt et al.
5,520,188 A 5/1996 Hennige et al.
5,523,058 A 6/1996 Umemura et al.
5,524,620 A 6/1996 Rosenschein
5,540,909 A 7/1996 Schutt
5,542,935 A 8/1996 Unger et al.
5,558,092 A 9/1996 Unger et al.
5,563,346 A 10/1996 Bartelt et al.
5,566,675 A 10/1996 Li et al.
5,573,497 A 11/1996 Chapelon
5,580,575 A 12/1996 Unger et al.
5,582,578 A 12/1996 Zhong et al.
5,590,657 A 1/1997 Cain et al.
5,601,526 A 2/1997 Chapelon et al.
5,617,862 A 4/1997 Cole et al.
5,648,098 A 7/1997 Porter
5,665,054 A 9/1997 Dory
5,666,954 A 9/1997 Chapelon et al.
5,676,452 A 10/1997 Scholz
5,676,692 A 10/1997 Sanghvi et al.
5,678,554 A 10/1997 Hossack et al.
5,683,064 A 11/1997 Copeland et al.
5,694,936 A 12/1997 Fujimoto et al.
5,695,460 A 12/1997 Siegel et al.
5,717,657 A 2/1998 Ruffa
5,720,287 A 2/1998 Chapelon et al.
5,724,972 A 3/1998 Petrofsky
5,743,863 A 4/1998 Chapelon
5,753,929 A 5/1998 Bliss
5,759,162 A 6/1998 Oppelt et al.
5,766,138 A 6/1998 Rattner
5,769,790 A 6/1998 Watkins et al.
5,797,848 A 8/1998 Marian et al.
5,820,623 A 10/1998 Ng
5,823,962 A 10/1998 Schaetzle et al.
5,827,204 A 10/1998 Grandia et al.
5,836,896 A 11/1998 Rosenschein
5,849,727 A 12/1998 Porter et al.
5,873,902 A 2/1999 Sanghvi et al.
5,879,314 A 3/1999 Peterson et al.

(56) References Cited

U.S. PATENT DOCUMENTS 5,928,169 A 7/1999 Schitzle et al.
5,932,807 A 8/1999 Mallart
5,947,904 A 9/1999 Hossack et al.
6,001,069 A 12/1999 Tachibana et al.
6,007,499 A 12/1999 Martin et al.
6,022,309 A 2/2000 Celliers et al.
6,036,667 A 3/2000 Manna et al.
6,088,613 A 7/2000 Unger
6,093,883 A 7/2000 Sanghvi et al.
6,113,558 A 9/2000 Rosenschein et al.
6,126,607 A 10/2000 Whitmore, III et al.
6,128,958 A 10/2000 Cain
6,143,018 A 11/2000 Beuthan et al.
6,165,144 A 12/2000 Talish et al.
6,176,842 B1 1/2001 Tachibana et al.
6,296,619 B1 10/2001 Brisken et al.
6,308,585 B1 10/2001 Nilsson et al.
6,308,710 B1 10/2001 Silva
6,309,355 B1 10/2001 Cain et al.
6,318,146 B1 11/2001 Madsen et al.
6,321,109 B2 11/2001 Ben-Haim et al.
6,338,566 B1 1/2002 Verdier
6,344,489 B1 2/2002 Spears
6,391,020 B1 5/2002 Kurtz et al.
6,413,216 B1 7/2002 Cain et al.
6,419,648 B1 7/2002 Vitek et al.
6,424,885 B1 7/2002 Niemeyer et al.
6,470,204 B1 10/2002 Uzgiris et al.
6,488,639 B1 12/2002 Ribault et al.
6,490,469 B2 12/2002 Candy
6,500,141 B1 12/2002 Irion et al.
6,506,154 B1 1/2003 Ezion et al.
6,506,171 B1 1/2003 Vitek et al.
6,508,774 B1 1/2003 Acker et al.
6,511,428 B1 1/2003 Azuma et al.
6,511,444 B2 1/2003 Hynynen et al.
6,522,142 B1 2/2003 Freundlich
6,524,251 B2 2/2003 Rabiner et al.
6,536,553 B1 3/2003 Scanlon
6,543,272 B1 4/2003 Vitek
6,556,750 B2 4/2003 Constantino et al.
6,559,644 B2 5/2003 Froundlich et al.
6,576,220 B2 6/2003 Inger
6,599,288 B2 7/2003 Maguire et al.
6,607,498 B2 8/2003 Eshel
6,612,988 B2 9/2003 Maor et al.
6,613,004 B1 9/2003 Vitek et al.
6,613,005 B1 9/2003 Friedman et al.
6,626,854 B2 9/2003 Friedman et al.
6,626,855 B1 9/2003 Weng et al.
6,645,162 B2 11/2003 Friedman et al.
6,648,839 B2 11/2003 Manna et al.
6,666,833 B1 12/2003 Friedman et al.
6,685,640 B1 2/2004 Fry et al.
6,685,657 B2 2/2004 Jones
6,705,994 B2 3/2004 Vortman et al.
6,719,449 B1 4/2004 Laugharn, Jr. et al.
6,719,694 B2 4/2004 Weng et al.
6,735,461 B2 5/2004 Vitek et al.
6,736,814 B2 5/2004 Manna et al.
6,750,463 B1 6/2004 Riley
6,770,031 B2 8/2004 Hynynen et al.
6,773,401 B1 * 8/2004 Dreschel .............. A61B 8/4483
600/459
6,775,438 B1 8/2004 Gaedke et al.
6,788,977 B2 9/2004 Fenn et al.
6,790,180 B2 9/2004 Vitek
6,820,160 B1 11/2004 Allman
6,852,082 B2 2/2005 Strickberger et al.
6,869,439 B2 3/2005 White et al.
6,890,332 B2 5/2005 Truckal et al.
6,929,609 B2 8/2005 Asafusa
7,004,282 B2 2/2006 Manna et al.
7,059,168 B2 6/2006 Hibi et al.
7,128,711 B2 10/2006 Medan et al.
7,128,719 B2 10/2006 Rosenberg
7,175,596 B2 2/2007 Vitek et al.
7,175,599 B2 2/2007 Hynynen et al.
7,196,313 B2 3/2007 Quinones
7,223,239 B2 5/2007 Schulze et al.
7,258,674 B2 8/2007 Cribbs et al.
7,273,458 B2 9/2007 Prausnitz et al.
7,273,459 B2 9/2007 Desilets et al.
7,300,414 B1 11/2007 Holland et al.
7,311,679 B2 12/2007 Desilets et al.
7,331,951 B2 2/2008 Eshel et al.
7,341,569 B2 3/2008 Soltani et al.
7,347,855 B2 3/2008 Eshel et al.
7,358,226 B2 4/2008 Dayton et al.
7,359,640 B2 4/2008 Onde et al.
7,367,948 B2 5/2008 O'Donnell et al.
7,374,551 B2 5/2008 Liang et al.
7,377,900 B2 5/2008 Vitek et al.
7,429,249 B1 9/2008 Winder et al.
7,431,704 B2 10/2008 Babaev
7,442,168 B2 10/2008 Novak et al.
7,462,488 B2 12/2008 Madsen et al.
7,559,905 B2 7/2009 Kagosaki et al.
7,656,638 B2 2/2010 Laakso et al.
7,695,437 B2 4/2010 Quistgaard et al.
7,714,481 B2 5/2010 Sakai
7,771,359 B2 8/2010 Adam
7,967,763 B2 6/2011 Deem et al.
8,057,408 B2 11/2011 Cain et al.
8,295,912 B2 10/2012 Gertner
8,333,115 B1 12/2012 Garvey et al.
8,337,407 B2 12/2012 Quistgaard et al.
8,342,467 B2 1/2013 Stachowski et al.
8,376,970 B2 2/2013 Babaev
8,539,813 B2 9/2013 Cain et al.
8,568,339 B2 10/2013 Rybyanets
8,636,664 B2 1/2014 Brannan
8,715,187 B2 5/2014 Landberg Davis et al.
8,845,537 B2 9/2014 Tanaka et al.
8,932,239 B2 1/2015 Sokka et al.
9,028,434 B2 5/2015 Tanaka
9,049,783 B2 6/2015 Teofilovic
9,061,131 B2 6/2015 Jahnke et al.
9,144,694 B2 9/2015 Cain
9,220,476 B2 12/2015 Coussios et al.
9,228,730 B1 1/2016 Inbody
9,302,124 B2 4/2016 Konofagou et al.
9,457,201 B2 10/2016 Hoelscher et al.
9,526,923 B2 12/2016 Jahnke et al.
9,636,133 B2 5/2017 Hall et al.
9,642,634 B2 5/2017 Cain et al.
9,763,688 B2 9/2017 Stulen et al.
9,901,753 B2 2/2018 Cain et al.
9,943,708 B2 4/2018 Roberts et al.
10,022,107 B2 7/2018 Thornton et al.
10,046,179 B2 8/2018 Oskar-Kohler
10,046,181 B2 8/2018 Barthe et al.
10,058,352 B2 8/2018 Carvell et al.
10,071,266 B2 9/2018 Cain
10,130,828 B2 11/2018 Vortman et al.
10,219,815 B2 3/2019 Maxwell et al.
10,293,187 B2 5/2019 Cannata et al.
10,293,374 B2 * 5/2019 Torashima ......... G01N 29/2418
10,751,015 B2 8/2020 Anderson et al.
10,751,125 B2 8/2020 Levy et al.
10,765,892 B1 9/2020 Vitek et al.
10,772,646 B2 9/2020 Lu et al.
10,780,298 B2 9/2020 Cain et al.
10,791,991 B2 10/2020 Burkett et al.
10,799,209 B2 10/2020 Lahti et al.
10,806,421 B2 10/2020 Keller
10,820,813 B2 11/2020 Lipert
10,847,264 B2 11/2020 Mansker et al.
10,849,511 B2 12/2020 Tochterman et al.
10,869,603 B2 12/2020 Millett et al.
10,869,633 B2 12/2020 Burkett
10,869,648 B2 12/2020 Hubbard et al.
10,874,353 B2 12/2020 Assif
10,874,409 B2 12/2020 Matsubara et al.

(56) References Cited

U.S. PATENT DOCUMENTS

| | | | |
|---|---|---|---|
| 10,878,586 | B2 | 12/2020 | Brokman et al. |
| 10,888,232 | B2 | 1/2021 | Anderson et al. |
| 10,893,808 | B2 | 1/2021 | Dorando |
| 10,900,933 | B2 | 1/2021 | Prus et al. |
| 10,905,394 | B2 | 2/2021 | Stigall et al. |
| 10,912,463 | B2 | 2/2021 | Davies et al. |
| 10,925,688 | B2 | 2/2021 | Millett et al. |
| 10,927,003 | B2 | 2/2021 | Millett et al. |
| 10,932,678 | B2 | 3/2021 | Burkett |
| 10,939,826 | B2 | 3/2021 | Glynn et al. |
| 10,942,022 | B2 | 3/2021 | Johansson et al. |
| 10,973,419 | B2 | 4/2021 | Corl |
| 10,993,618 | B2 | 5/2021 | Mansker et al. |
| 10,993,628 | B2 | 5/2021 | Tochterman |
| 10,993,694 | B2 | 5/2021 | Meyer et al. |
| 11,000,185 | B2 | 5/2021 | Stigall et al. |
| 11,006,840 | B2 | 5/2021 | Stigall |
| 11,013,491 | B2 | 5/2021 | Rice et al. |
| 11,020,087 | B2 | 6/2021 | Hoffman |
| 11,020,089 | B2 | 6/2021 | Corl |
| 11,026,591 | B2 | 6/2021 | Burkett et al. |
| 11,040,140 | B2 | 6/2021 | Unser et al. |
| 11,058,399 | B2 | 7/2021 | Xu et al. |
| 11,071,522 | B2 | 7/2021 | Hynynen et al. |
| 11,103,731 | B2 | 8/2021 | Vortman et al. |
| 11,112,473 | B2 | 9/2021 | Assif |
| 11,119,552 | B2 | 9/2021 | Spencer et al. |
| 11,120,896 | B2 | 9/2021 | Balignasay et al. |
| 11,123,019 | B2 | 9/2021 | Merritt et al. |
| 11,123,575 | B2 | 9/2021 | Vortman et al. |
| 11,135,454 | B2 | 10/2021 | Xu et al. |
| 11,141,063 | B2 | 10/2021 | Kemp et al. |
| 11,141,131 | B2 | 10/2021 | Stigall et al. |
| 11,160,513 | B2 | 11/2021 | Anderson et al. |
| 11,205,507 | B2 | 12/2021 | Anderson et al. |
| 11,219,748 | B2 | 1/2022 | Burkett et al. |
| 11,224,349 | B2 | 1/2022 | Davies et al. |
| 11,224,403 | B2 | 1/2022 | Cort |
| 11,224,407 | B2 | 1/2022 | Wrolstad et al. |
| 11,234,649 | B2 | 2/2022 | Matsubara et al. |
| 11,246,533 | B2 | 2/2022 | Henderson et al. |
| 11,246,565 | B2 | 2/2022 | Corl |
| 11,253,225 | B2 | 2/2022 | Hancock et al. |
| 11,260,160 | B2 | 3/2022 | Matsubara et al. |
| 11,272,845 | B2 | 3/2022 | Cheline et al. |
| 11,272,904 | B2 | 3/2022 | Vortman et al. |
| 11,291,866 | B2 | 4/2022 | Levy et al. |
| 11,298,030 | B2 | 4/2022 | Davies et al. |
| 11,309,071 | B2 | 4/2022 | Anderson |
| 11,311,271 | B2 | 4/2022 | Stigall et al. |
| 11,324,410 | B2 | 5/2022 | Burkett |
| 11,350,906 | B2 | 6/2022 | Castella et al. |
| 11,350,954 | B2 | 6/2022 | De Cicco et al. |
| 11,364,042 | B2 | 6/2022 | Maxwell et al. |
| 11,369,346 | B2 | 6/2022 | De Cicco et al. |
| 11,369,994 | B2 | 6/2022 | Greenberg et al. |
| 11,395,638 | B2 | 7/2022 | Shin et al. |
| 11,406,334 | B2 | 8/2022 | Merritt |
| 11,406,355 | B2 | 8/2022 | Hoffman et al. |
| 11,406,498 | B2 | 8/2022 | Stigall et al. |
| 11,408,987 | B2 | 8/2022 | Vignon et al. |
| 11,413,017 | B2 | 8/2022 | Stigall et al. |
| 11,419,580 | B2 | 8/2022 | Stigall et al. |
| 11,426,140 | B2 | 8/2022 | Sudol et al. |
| 11,432,795 | B2 | 9/2022 | Merritt |
| 11,432,900 | B2 | 9/2022 | Rakic et al. |
| 11,446,000 | B2 | 9/2022 | Minas et al. |
| 11,452,496 | B2 | 9/2022 | Minas et al. |
| 11,452,506 | B2 | 9/2022 | Perez et al. |
| 11,471,215 | B2 | 10/2022 | Stigall et al. |
| 11,484,294 | B2 | 11/2022 | Hancock et al. |
| 11,510,632 | B2 | 11/2022 | Begin et al. |
| 11,517,291 | B2 | 12/2022 | Kantor et al. |
| 11,520,874 | B2 | 12/2022 | Kennedy et al. |
| 11,524,183 | B1 | 12/2022 | Garcia Gutierrez et al. |
| 11,527,001 | B2 | 12/2022 | Brokman et al. |
| 11,547,389 | B2 | 1/2023 | Shin et al. |
| 11,553,889 | B2 | 1/2023 | Spencer et al. |
| 11,554,386 | B2 | 1/2023 | Pernot et al. |
| 11,559,207 | B2 | 1/2023 | Stigall et al. |
| 11,567,153 | B2 | 1/2023 | Stormont et al. |
| 11,576,649 | B2 | 2/2023 | Corl |
| 11,576,652 | B2 | 2/2023 | De Cicco et al. |
| 11,583,193 | B2 | 2/2023 | Groenland et al. |
| 11,589,835 | B2 | 2/2023 | Stigall et al. |
| 11,596,351 | B2 | 3/2023 | Nair |
| 11,596,384 | B2 | 3/2023 | Nair et al. |
| 11,596,385 | B2 | 3/2023 | Stigall et al. |
| 11,596,387 | B2 | 3/2023 | Song |
| 11,596,389 | B2 | 3/2023 | Nair |
| 11,596,469 | B2 | 3/2023 | Nair |
| 11,622,746 | B2 | 4/2023 | Minas et al. |
| 11,638,576 | B2 | 5/2023 | Groenland et al. |
| 11,647,989 | B2 | 5/2023 | Hope Simpson et al. |
| 11,648,424 | B2 | 5/2023 | Cannata et al. |
| 11,653,895 | B2 | 5/2023 | Stigall et al. |
| 11,660,070 | B2 | 5/2023 | Stigall et al. |
| 11,666,245 | B2 | 6/2023 | Rajguru et al. |
| 11,666,307 | B2 | 6/2023 | Unser |
| 11,672,433 | B2 | 6/2023 | Park et al. |
| 11,672,552 | B2 | 6/2023 | Pasquino et al. |
| 11,672,953 | B2 | 6/2023 | May |
| 11,684,342 | B2 | 6/2023 | Groenland et al. |
| 11,684,807 | B2 | 6/2023 | Vortman et al. |
| 11,701,134 | B2 | 7/2023 | Maxwell et al. |
| 11,707,207 | B2 | 7/2023 | Stigall et al. |
| 11,707,254 | B2 | 7/2023 | Tuillio et al. |
| 11,733,881 | B2 | 8/2023 | Perez |
| 11,737,728 | B2 | 8/2023 | Davies et al. |
| 11,744,527 | B2 | 9/2023 | Scott et al. |
| 11,744,547 | B2 | 9/2023 | Hynynen |
| 11,759,169 | B2 | 9/2023 | Cort |
| 11,759,174 | B2 | 9/2023 | Saroha et al. |
| 11,766,237 | B2 | 9/2023 | Anderson |
| 11,771,370 | B2 | 10/2023 | Hynynen |
| 11,771,405 | B2 | 10/2023 | Rhodes |
| 11,771,869 | B2 | 10/2023 | Cicco |
| 11,779,307 | B2 | 10/2023 | Norris et al. |
| 11,806,167 | B2 | 11/2023 | Burkett |
| 11,813,484 | B2 | 11/2023 | Cannata et al. |
| 11,813,485 | B2 | 11/2023 | Xu et al. |
| 11,819,712 | B2 | 11/2023 | Cain et al. |
| 11,854,687 | B2 | 12/2023 | Keller |
| 11,857,362 | B2 | 1/2024 | Wrolstad et al. |
| 11,857,807 | B2 | 1/2024 | Levy et al. |
| 11,864,918 | B2 | 1/2024 | Burkett et al. |
| 11,872,412 | B2 | 1/2024 | Vortman et al. |
| 11,879,973 | B2 | 1/2024 | Prus et al. |
| 11,883,235 | B2 | 1/2024 | Stigall et al. |
| 11,890,025 | B2 | 2/2024 | Stigall et al. |
| 11,890,136 | B2 | 2/2024 | Stigall et al. |
| 11,890,137 | B2 | 2/2024 | Jenkins et al. |
| 11,950,954 | B2 | 4/2024 | Hyun et al. |
| 11,963,822 | B2 | 4/2024 | Wrolstad |
| 11,980,778 | B2 | 5/2024 | Cannata et al. |
| 11,986,682 | B2 | 5/2024 | Prus et al. |
| 11,992,366 | B2 | 5/2024 | Stigall et al. |
| 12,017,013 | B2 | 6/2024 | Sasamine et al. |
| 12,035,919 | B2 | 7/2024 | Unser |
| 12,036,066 | B2 | 7/2024 | De Cicco et al. |
| 12,053,194 | B2 | 8/2024 | Goertz et al. |
| 12,082,970 | B2 | 9/2024 | Goodman |
| 12,096,949 | B2 | 9/2024 | Fermi et al. |
| 12,097,072 | B2 | 9/2024 | Stigall et al. |
| 12,112,850 | B2 | 10/2024 | Kuo et al. |
| 12,115,007 | B2 | 10/2024 | Merritt et al. |
| 12,144,677 | B2 | 11/2024 | Corl |
| 12,167,931 | B2 | 12/2024 | Corl |
| 12,178,642 | B2 | 12/2024 | Rajguru et al. |
| 12,178,643 | B2 | 12/2024 | Stigall et al. |
| 12,186,130 | B2 | 1/2025 | Davies |
| 12,220,259 | B2 | 2/2025 | Burkett et al. |
| 12,232,907 | B2 | 2/2025 | Chao et al. |
| 12,246,195 | B2 | 3/2025 | Levy et al. |

(56) References Cited

U.S. PATENT DOCUMENTS

2001/0039420 A1 11/2001 Burbank et al.
2001/0041163 A1 11/2001 Sugita
2002/0045890 A1 4/2002 Celliers et al.
2002/0078964 A1 6/2002 Kovac et al.
2002/0099356 A1 7/2002 Unger et al.
2002/0145091 A1 10/2002 Talish et al.
2003/0092982 A1 5/2003 Eppstein
2003/0112922 A1 6/2003 Burdette et al.
2003/0149352 A1 8/2003 Liang et al.
2003/0157025 A1 8/2003 Unger et al.
2003/0169591 A1 9/2003 Cochran
2003/0181833 A1 9/2003 Faragalla et al.
2003/0199857 A1 10/2003 Eizenhofer
2003/0221561 A1 12/2003 Milo
2003/0236539 A1 12/2003 Rabiner et al.
2004/0127815 A1 7/2004 Marchitto et al.
2004/0138563 A1 7/2004 Moehring et al.
2004/0162571 A1 8/2004 Rabiner et al.
2004/0164213 A1 8/2004 Stephan
2004/0236248 A1 11/2004 Svedman
2004/0243021 A1 12/2004 Murphy et al.
2004/0249509 A1 12/2004 Rogers et al.
2004/0260214 A1 12/2004 Echt et al.
2005/0011296 A1 1/2005 Koseki
2005/0020945 A1 1/2005 Tosaya et al.
2005/0038339 A1 2/2005 Chauhan et al.
2005/0038361 A1 2/2005 Zhong et al.
2005/0121734 A1* 6/2005 Degertekin ........... B06B 1/0292 438/48
2005/0152561 A1 7/2005 Spencer
2005/0154314 A1 7/2005 Quistgaard
2005/0154431 A1 7/2005 Quistgaard et al.
2005/0203399 A1 9/2005 Vaezy et al.
2005/0215901 A1 9/2005 Anderson et al.
2005/0234438 A1 10/2005 Mast et al.
2005/0283098 A1 12/2005 Conston et al.
2006/0058678 A1 3/2006 Vitek et al.
2006/0060991 A1 3/2006 Holsteyns et al.
2006/0074303 A1 4/2006 Chornenky et al.
2006/0089636 A1 4/2006 Christopherson et al.
2006/0173321 A1 8/2006 Kubota et al.
2006/0173387 A1 8/2006 Hansmann et al.
2006/0184166 A1 8/2006 Valle et al.
2006/0206028 A1 9/2006 Lee et al.
2006/0229659 A1 10/2006 Gifford et al.
2006/0241466 A1 10/2006 Ottoboni et al.
2006/0241523 A1 10/2006 Sinelnikov et al.
2006/0241533 A1 10/2006 Geller
2006/0264760 A1 11/2006 Liu et al.
2006/0293598 A1 12/2006 Fraser
2006/0293630 A1 12/2006 Manna et al.
2007/0010805 A1 1/2007 Fedewa et al.
2007/0016039 A1 1/2007 Vortman et al.
2007/0044562 A1 3/2007 Sarr
2007/0065420 A1 3/2007 Johnson
2007/0083120 A1 4/2007 Cain et al.
2007/0140413 A1 6/2007 Saracen
2007/0161902 A1 7/2007 Dan
2007/0167764 A1 7/2007 Hynynen
2007/0205785 A1 9/2007 Nilsson
2007/0219448 A1 9/2007 Seip et al.
2007/0239001 A1 10/2007 Mehl et al.
2007/0293762 A1* 12/2007 Sawada ................. B06B 1/0633 600/459
2008/0013593 A1 1/2008 Kawabata
2008/0033297 A1 2/2008 Sliwa
2008/0033417 A1 2/2008 Nields et al.
2008/0051656 A1 2/2008 Vaezy et al.
2008/0055003 A1 3/2008 Unnikrishnan et al.
2008/0082026 A1 4/2008 Schmidt et al.
2008/0091125 A1 4/2008 Owen et al.
2008/0126665 A1 5/2008 Burr et al.
2008/0154132 A1 6/2008 Hall et al.
2008/0167555 A1 7/2008 Qian et al.
2008/0177180 A1 7/2008 Azhari et al.
2008/0194965 A1 8/2008 Sliwa et al.
2008/0214964 A1 9/2008 Chapelon et al.
2008/0262345 A1 10/2008 Fichtinger et al.
2008/0262486 A1 10/2008 Zvuloni et al.
2008/0269614 A1* 10/2008 Adachi .................... A61B 8/12 310/317
2008/0300485 A1 12/2008 Liu et al.
2008/0312561 A1 12/2008 Chauhan
2008/0319376 A1 12/2008 Wilcox et al.
2009/0012514 A1 1/2009 Moonen et al.
2009/0030339 A1 1/2009 Cheng et al.
2009/0036773 A1 2/2009 Lau et al.
2009/0112098 A1 4/2009 Vaezy et al.
2009/0198094 A1 8/2009 Fenster et al.
2009/0211587 A1 8/2009 Lawrentschuk
2009/0227874 A1 9/2009 Suri et al.
2009/0230822 A1 9/2009 Kushculey et al.
2009/0254008 A1 10/2009 Shields, Jr.
2009/0287083 A1 11/2009 Kushculey et al.
2009/0306502 A1 12/2009 Lacoste
2010/0011845 A1 1/2010 Laugharn et al.
2010/0042020 A1 2/2010 Ben-Ezra
2010/0056924 A1 3/2010 Powers
2010/0059264 A1 3/2010 Hasegawa et al.
2010/0069797 A1 3/2010 Cain et al.
2010/0125225 A1 5/2010 Gelbart et al.
2010/0152624 A1 6/2010 Tanis et al.
2010/0163694 A1 7/2010 Fadler et al.
2010/0204578 A1 8/2010 Schmidt et al.
2010/0251823 A1* 10/2010 Adachi ................ A61B 8/4483 73/606
2010/0255623 A1* 10/2010 Huang .................... H01L 24/19 257/E21.532
2010/0261994 A1 10/2010 Davalos et al.
2010/0274136 A1 10/2010 Cerofolini
2010/0286519 A1 11/2010 Lee et al.
2010/0298744 A1 11/2010 Altshuler et al.
2010/0305432 A1 12/2010 Duhay et al.
2010/0317971 A1 12/2010 Fan et al.
2010/0318002 A1 12/2010 Prus et al.
2011/0072970 A1 3/2011 Slobodzian et al.
2011/0112400 A1 5/2011 Emery et al.
2011/0118600 A1 5/2011 Gertner
2011/0118602 A1 5/2011 Weng et al.
2011/0144490 A1 6/2011 Davis et al.
2011/0144545 A1 6/2011 Fan et al.
2011/0172529 A1 7/2011 Gertner
2011/0178444 A1 7/2011 Slayton et al.
2011/0245671 A1 10/2011 Sato
2011/0251528 A1 10/2011 Canney et al.
2011/0257524 A1 10/2011 Gertner
2011/0263967 A1 10/2011 Bailey et al.
2011/0270136 A1 11/2011 Vitek et al.
2011/0319927 A1 12/2011 Nita
2012/0029337 A1 2/2012 Aoyag
2012/0029353 A1 2/2012 Slayton et al.
2012/0029393 A1 2/2012 Lee
2012/0059264 A1 3/2012 Hope Simpson et al.
2012/0059285 A1 3/2012 Soltani et al.
2012/0092724 A1 4/2012 Pettis
2012/0111339 A1 5/2012 Barthe et al.
2012/0130288 A1 5/2012 Holland et al.
2012/0136279 A1 5/2012 Tanaka et al.
2012/0158013 A1 6/2012 Stefanchik et al.
2012/0172720 A1 7/2012 Asami et al.
2012/0189998 A1 7/2012 Kruecker et al.
2012/0215157 A1 8/2012 Berryman et al.
2012/0232388 A1 9/2012 Curra et al.
2012/0259250 A1 10/2012 Sapozhnikov et al.
2012/0271167 A1 10/2012 Holland et al.
2012/0271223 A1 10/2012 Khanna
2012/0281902 A1 11/2012 Oikawa et al.
2013/0051178 A1 2/2013 Rybyanets
2013/0053691 A1 2/2013 Kawabata et al.
2013/0090579 A1 4/2013 Cain et al.
2013/0102932 A1 4/2013 Cain et al.
2013/0144165 A1 6/2013 Ebbini et al.
2013/0172739 A1 7/2013 Paladini
2013/0190623 A1 7/2013 Bertolina et al.

(56) References Cited

U.S. PATENT DOCUMENTS

| | | | |
|---|---|---|---|
| 2013/0190661 A1 | 7/2013 | Wing et al. | |
| 2013/0255426 A1 | 10/2013 | Kassow et al. | |
| 2013/0257224 A1* | 10/2013 | Wodnicki | B06B 1/0622 29/25.35 |
| 2013/0261467 A1* | 10/2013 | Dausch | A61B 8/12 29/25.35 |
| 2013/0267853 A1* | 10/2013 | Dausch | A61B 8/4494 600/459 |
| 2013/0303906 A1 | 11/2013 | Cain et al. | |
| 2014/0005521 A1* | 1/2014 | Kohler | A61B 6/4057 601/3 |
| 2014/0030806 A1 | 1/2014 | Dudley et al. | |
| 2014/0039358 A1 | 2/2014 | Zhou et al. | |
| 2014/0046181 A1 | 2/2014 | Benchimol et al. | |
| 2014/0058293 A1 | 2/2014 | Hynynen et al. | |
| 2014/0058294 A1 | 2/2014 | Gross et al. | |
| 2014/0073995 A1 | 3/2014 | Teofilovic et al. | |
| 2014/0074076 A1 | 3/2014 | Gertner | |
| 2014/0088613 A1 | 3/2014 | Seo et al. | |
| 2014/0100459 A1 | 4/2014 | Xu et al. | |
| 2014/0112107 A1 | 4/2014 | Guo et al. | |
| 2014/0128734 A1 | 5/2014 | Genstler et al. | |
| 2014/0180072 A1* | 6/2014 | Davies | A61B 6/12 600/424 |
| 2014/0180273 A1* | 6/2014 | Nair | A61B 18/1492 606/34 |
| 2014/0200489 A1 | 7/2014 | Behar et al. | |
| 2014/0243664 A1 | 8/2014 | El-Sayed et al. | |
| 2014/0288428 A1* | 9/2014 | Rothberg | G01S 7/52047 600/443 |
| 2014/0316269 A1 | 10/2014 | Zhang et al. | |
| 2014/0324034 A1 | 10/2014 | Assaf et al. | |
| 2014/0330124 A1 | 11/2014 | Carol | |
| 2014/0378832 A1 | 12/2014 | Sanghvi et al. | |
| 2014/0378964 A1 | 12/2014 | Pearson | |
| 2015/0011875 A1 | 1/2015 | Noordhoek et al. | |
| 2015/0063668 A1 | 3/2015 | You et al. | |
| 2015/0073261 A1 | 3/2015 | Kohler et al. | |
| 2015/0080926 A1 | 3/2015 | Emery | |
| 2015/0148659 A1 | 5/2015 | Vahala | |
| 2015/0151141 A1 | 6/2015 | Arnal et al. | |
| 2015/0190121 A1 | 7/2015 | Slayton et al. | |
| 2015/0190659 A1 | 7/2015 | Kolher | |
| 2015/0196239 A1 | 7/2015 | Meehan et al. | |
| 2015/0224347 A1 | 8/2015 | Barthe et al. | |
| 2015/0257779 A1 | 9/2015 | Sinelnikov et al. | |
| 2015/0258352 A1 | 9/2015 | Lin et al. | |
| 2015/0265243 A1 | 9/2015 | Kelly | |
| 2015/0273246 A1 | 10/2015 | Darlington et al. | |
| 2015/0297177 A1 | 10/2015 | Boctor et al. | |
| 2015/0305710 A1* | 10/2015 | Stigall | A61B 8/0891 600/424 |
| 2016/0004933 A1 | 1/2016 | Hu et al. | |
| 2016/0114194 A1 | 4/2016 | Gertner | |
| 2016/0120572 A1 | 5/2016 | Lee | |
| 2016/0135782 A1 | 5/2016 | Chen et al. | |
| 2016/0151618 A1 | 6/2016 | Powers et al. | |
| 2016/0184614 A1 | 6/2016 | Matula et al. | |
| 2016/0206341 A1 | 7/2016 | Slayton | |
| 2016/0206867 A1 | 7/2016 | Hossack et al. | |
| 2016/0249859 A1 | 9/2016 | Babkin et al. | |
| 2016/0287909 A1 | 10/2016 | Maxwell et al. | |
| 2016/0303166 A1 | 10/2016 | Katz et al. | |
| 2016/0331583 A1 | 11/2016 | Geringer | |
| 2016/0331585 A1 | 11/2016 | Kim | |
| 2016/0339273 A1 | 11/2016 | Al Mayiah | |
| 2016/0345938 A1 | 12/2016 | Tanter et al. | |
| 2016/0354087 A1 | 12/2016 | Noonan et al. | |
| 2016/0361574 A1 | 12/2016 | Barthe et al. | |
| 2017/0000376 A1 | 1/2017 | Partanen et al. | |
| 2017/0049463 A1 | 2/2017 | Popovic et al. | |
| 2017/0071515 A1 | 3/2017 | Chevillet et al. | |
| 2017/0072227 A1 | 3/2017 | Khokhlova et al. | |
| 2017/0072228 A1 | 3/2017 | Wang et al. | |
| 2017/0100145 A1 | 4/2017 | Khoklova et al. | |
| 2017/0120080 A1 | 5/2017 | Phillips et al. | |
| 2017/0165046 A1 | 6/2017 | Johnson et al. | |
| 2017/0183062 A1 | 6/2017 | Lee | |
| 2017/0197099 A1 | 7/2017 | Ruebel et al. | |
| 2017/0232277 A1 | 8/2017 | Hall et al. | |
| 2017/0263846 A1 | 9/2017 | Nakamura et al. | |
| 2017/0281983 A1 | 10/2017 | Marquet et al. | |
| 2017/0326589 A1* | 11/2017 | Sudol | H03H 3/0072 |
| 2018/0000444 A1 | 1/2018 | Dayton et al. | |
| 2018/0028841 A1 | 2/2018 | Konofagou et al. | |
| 2018/0064412 A1 | 3/2018 | Messas et al. | |
| 2018/0161086 A1 | 6/2018 | Davalos et al. | |
| 2018/0169444 A1 | 6/2018 | Averkiou et al. | |
| 2018/0206816 A1 | 7/2018 | Prus et al. | |
| 2018/0236271 A1 | 8/2018 | Tanter et al. | |
| 2018/0317884 A1 | 11/2018 | Chapelon et al. | |
| 2018/0374471 A1 | 12/2018 | Dirksen et al. | |
| 2019/0000422 A1 | 1/2019 | West et al. | |
| 2019/0023804 A1 | 1/2019 | Onik et al. | |
| 2019/0082998 A1 | 3/2019 | Nowroozi et al. | |
| 2019/0275353 A1 | 9/2019 | Cannata et al. | |
| 2019/0282294 A1 | 9/2019 | Davalos et al. | |
| 2019/0314045 A1 | 10/2019 | Cunitz et al. | |
| 2019/0320904 A1 | 10/2019 | Mei | |
| 2019/0323086 A1 | 10/2019 | Leuthardt et al. | |
| 2019/0328500 A1 | 10/2019 | Cichon et al. | |
| 2020/0010575 A1 | 1/2020 | Hode et al. | |
| 2020/0055085 A1 | 2/2020 | Taffler | |
| 2020/0078608 A1 | 3/2020 | Maxwell et al. | |
| 2020/0107843 A1 | 4/2020 | Goertz et al. | |
| 2020/0182989 A1 | 6/2020 | Freeman et al. | |
| 2020/0194117 A1 | 6/2020 | Krieger et al. | |
| 2020/0253550 A1 | 8/2020 | Nair | |
| 2020/0254285 A1 | 8/2020 | Jang et al. | |
| 2020/0260964 A1 | 8/2020 | Collins et al. | |
| 2020/0282239 A1 | 9/2020 | Beder et al. | |
| 2020/0289080 A1 | 9/2020 | Yang et al. | |
| 2020/0305842 A1 | 10/2020 | Rosenzweig et al. | |
| 2020/0323515 A1 | 10/2020 | Levy | |
| 2020/0330039 A1 | 10/2020 | Burkett et al. | |
| 2020/0330075 A1 | 10/2020 | O'Reilly et al. | |
| 2020/0353293 A1 | 11/2020 | Khokhlova et al. | |
| 2020/0367835 A1 | 11/2020 | Anderson | |
| 2020/0375576 A1 | 12/2020 | Moulton | |
| 2020/0405258 A1 | 12/2020 | Dayton et al. | |
| 2020/0405259 A1 | 12/2020 | Merritt | |
| 2021/0000541 A1 | 1/2021 | Levy et al. | |
| 2021/0022703 A1 | 1/2021 | Nair | |
| 2021/0022714 A1 | 1/2021 | Zagrodsky et al. | |
| 2021/0100527 A1 | 4/2021 | Martin | |
| 2021/0108866 A1 | 4/2021 | Lucht et al. | |
| 2021/0161398 A1 | 6/2021 | Millett et al. | |
| 2021/0169515 A1 | 6/2021 | Pahk et al. | |
| 2021/0170204 A1 | 6/2021 | Vortman et al. | |
| 2021/0170205 A1 | 6/2021 | Vortman et al. | |
| 2021/0187331 A1 | 6/2021 | Zadicario et al. | |
| 2021/0196295 A1 | 7/2021 | Goudot et al. | |
| 2021/0220607 A1 | 7/2021 | Sasamine et al. | |
| 2021/0330294 A1 | 10/2021 | Hynynen et al. | |
| 2021/0353161 A1 | 11/2021 | Merritt et al. | |
| 2021/0386451 A1 | 12/2021 | Escudero et al. | |
| 2021/0401400 A1 | 12/2021 | Sheehan et al. | |
| 2022/0008036 A1 | 1/2022 | Gulsen et al. | |
| 2022/0022845 A1 | 1/2022 | Cori | |
| 2022/0031287 A1 | 2/2022 | Ebbini et al. | |
| 2022/0043143 A1 | 2/2022 | Prus et al. | |
| 2022/0079563 A1 | 3/2022 | Kemp | |
| 2022/0087640 A1 | 3/2022 | Minas et al. | |
| 2022/0166462 A1 | 5/2022 | Deurenberg et al. | |
| 2022/0167920 A1 | 6/2022 | Margolis | |
| 2022/0168470 A1 | 6/2022 | Ricotti et al. | |
| 2022/0196771 A1 | 6/2022 | Zur et al. | |
| 2022/0203139 A1 | 6/2022 | Shapira | |
| 2022/0219019 A1 | 7/2022 | Xu et al. | |
| 2022/0233890 A1 | 7/2022 | Hynynen et al. | |
| 2022/0240890 A1 | 8/2022 | Hancock et al. | |
| 2022/0257329 A1 | 8/2022 | Stigall et al. | |
| 2022/0280233 A1 | 9/2022 | Park et al. | |

(56) References Cited

U.S. PATENT DOCUMENTS

| | | | |
|---|---|---|---|
| 2022/0280367 | A1 | 9/2022 | Diodato et al. |
| 2022/0296211 | A1 | 9/2022 | Saroha et al. |
| 2022/0338750 | A1 | 10/2022 | Allen et al. |
| 2022/0346756 | A1 | 11/2022 | Chen |
| 2022/0370025 | A1 | 11/2022 | Regensburger et al. |
| 2022/0386970 | A1 | 12/2022 | Merritt |
| 2022/0395333 | A1 | 12/2022 | Merritt et al. |
| 2022/0409171 | A1 | 12/2022 | Sudol et al. |
| 2022/0409858 | A1 | 12/2022 | Lin |
| 2023/0000466 | A1 | 1/2023 | Levy et al. |
| 2023/0000469 | A1 | 1/2023 | Prus et al. |
| 2023/0008714 | A1 | 1/2023 | Rajguru et al. |
| 2023/0012365 | A1 | 1/2023 | Alpert et al. |
| 2023/0024998 | A1 | 1/2023 | Greenberg |
| 2023/0031859 | A1 | 2/2023 | Davies et al. |
| 2023/0037603 | A1 | 2/2023 | Pombo et al. |
| 2023/0038498 | A1 | 2/2023 | Xu et al. |
| 2023/0038543 | A1 | 2/2023 | Minas et al. |
| 2023/0042834 | A1 | 2/2023 | Henderson et al. |
| 2023/0045488 | A1 | 2/2023 | Rajguru et al. |
| 2023/0050732 | A1 | 2/2023 | Hancock et al. |
| 2023/0061534 | A1 | 3/2023 | Stopek |
| 2023/0073447 | A1 | 3/2023 | Minas et al. |
| 2023/0100912 | A1 | 3/2023 | Amar et al. |
| 2023/0112722 | A1 | 4/2023 | Hoffman et al. |
| 2023/0114972 | A1 | 4/2023 | Bigham et al. |
| 2023/0121688 | A1 | 4/2023 | Begin et al. |
| 2023/0145064 | A1 | 5/2023 | Vortman et al. |
| 2023/0181140 | A1 | 6/2023 | Cohen et al. |
| 2023/0181156 | A1 | 6/2023 | Cohen et al. |
| 2023/0190119 | A1 | 6/2023 | Groenland et al. |
| 2023/0190215 | A1 | 6/2023 | Nachtomy et al. |
| 2023/0190224 | A1 | 6/2023 | Rajguru et al. |
| 2023/0190225 | A1 | 6/2023 | Cohen et al. |
| 2023/0190226 | A1 | 6/2023 | Rajguru et al. |
| 2023/0190227 | A1 | 6/2023 | Cohen et al. |
| 2023/0190228 | A1 | 6/2023 | Cohen et al. |
| 2023/0190229 | A1 | 6/2023 | Cohen et al. |
| 2023/0190230 | A1 | 6/2023 | Yang et al. |
| 2023/0191162 | A1 | 6/2023 | Yau et al. |
| 2023/0196569 | A1 | 6/2023 | Cohen et al. |
| 2023/0200899 | A1 | 6/2023 | Nair |
| 2023/0201553 | A1 | 6/2023 | Levy et al. |
| 2023/0218230 | A1 | 7/2023 | Wu et al. |
| 2023/0218262 | A1 | 7/2023 | Boutelle et al. |
| 2023/0218266 | A1 | 7/2023 | Stigall et al. |
| 2023/0218269 | A1 | 7/2023 | Alpert et al. |
| 2023/0218930 | A1 | 7/2023 | Stopek et al. |
| 2023/0240615 | A1 | 8/2023 | May et al. |
| 2023/0240647 | A1 | 8/2023 | Minas et al. |
| 2023/0240792 | A1 | 8/2023 | Rakic et al. |
| 2023/0255597 | A1 | 8/2023 | O'Reilly et al. |
| 2023/0260601 | A1 | 8/2023 | Abel et al. |
| 2023/0263507 | A1 | 8/2023 | Groenland et al. |
| 2023/0270388 | A1 | 8/2023 | Richardson et al. |
| 2023/0293148 | A1 | 9/2023 | Stigall et al. |
| 2023/0293149 | A1 | 9/2023 | Stigall et al. |
| 2023/0309859 | A1 | 10/2023 | Sreedhar et al. |
| 2023/0310899 | A1 | 10/2023 | Hall et al. |
| 2023/0310900 | A1 | 10/2023 | Cannata et al. |
| 2023/0320600 | A1 | 10/2023 | Tochterman et al. |
| 2023/0321327 | A1 | 10/2023 | Maxwell et al. |
| 2023/0321398 | A1 | 10/2023 | May |
| 2023/0329559 | A1 | 10/2023 | Xu et al. |
| 2023/0333617 | A1 | 10/2023 | Spencer et al. |
| 2023/0334659 | A1 | 10/2023 | Marama et al. |
| 2023/0334677 | A1 | 10/2023 | Sturm |
| 2023/0338010 | A1 | 10/2023 | Sturm |
| 2023/0372025 | A1 | 11/2023 | Van Der Zaag et al. |
| 2023/0381544 | A1 | 11/2023 | Penot et al. |
| 2023/0389891 | A1 | 12/2023 | Cohen et al. |
| 2023/0398381 | A1 | 12/2023 | Vitek et al. |
| 2024/0000422 | A1 | 1/2024 | Cort |
| 2024/0000426 | A1 | 1/2024 | Davies et al. |
| 2024/0001157 | A1 | 1/2024 | Cannata et al. |
| 2024/0001158 | A1 | 1/2024 | Cannata et al. |
| 2024/0023928 | A1 | 1/2024 | Di Tullio et al. |
| 2024/0023930 | A1 | 1/2024 | Anderson |
| 2024/0023941 | A1 | 1/2024 | Rhodes |
| 2024/0024705 | A1 | 1/2024 | Xu et al. |
| 2024/0033542 | A1 | 2/2024 | Cain et al. |
| 2024/0065632 | A1 | 2/2024 | Burkett |
| 2024/0130746 | A1 | 4/2024 | Maxwell et al. |
| 2024/0138807 | A1 | 5/2024 | Minas |
| 2024/0139552 | A1 | 5/2024 | Duryea et al. |
| 2024/0139553 | A1 | 5/2024 | Miller et al. |
| 2024/0149078 | A1 | 5/2024 | Duryea et al. |
| 2024/0165666 | A1 | 5/2024 | Hynynen et al. |
| 2024/0188929 | A1 | 6/2024 | Minas et al. |
| 2024/0188931 | A1 | 6/2024 | Ossmann et al. |
| 2024/0189267 | A1 | 6/2024 | Bogott et al. |
| 2024/0189628 | A1 | 6/2024 | Grumbir et al. |
| 2024/0207654 | A1 | 6/2024 | Xu et al. |
| 2024/0225592 | A1 | 7/2024 | May et al. |
| 2024/0245374 | A1 | 7/2024 | Jenkins et al. |
| 2024/0245390 | A1 | 7/2024 | Winkler Brown et al. |
| 2024/0245465 | A1 | 7/2024 | Jenkins et al. |
| 2024/0285249 | A1 | 8/2024 | May |
| 2024/0299092 | A1 | 9/2024 | Boinagrov et al. |
| 2024/0307027 | A1 | 9/2024 | Minas |
| 2024/0315713 | A1 | 9/2024 | Maxwell et al. |
| 2024/0316367 | A1 | 9/2024 | Cannata et al. |
| 2024/0335680 | A1 | 10/2024 | Achrol et al. |
| 2024/0341732 | A1 | 10/2024 | Hoffman et al. |
| 2024/0350118 | A1 | 10/2024 | Jenkins et al. |
| 2024/0374242 | A1 | 11/2024 | Merritt et al. |
| 2024/0408416 | A1 | 12/2024 | Cannata et al. |
| 2025/0018227 | A1 | 1/2025 | Son et al. |
| 2025/0040912 | A1 | 2/2025 | Levy et al. |
| 2025/0041577 | A1 | 2/2025 | Shapira et al. |
| 2025/0072872 | A1 | 3/2025 | Nachtomy et al. |

FOREIGN PATENT DOCUMENTS

| | | | |
|---|---|---|---|
| BR | 112018017326 | B1 | 12/2022 |
| BR | 102023017634 | A2 | 1/2025 |
| CA | 3073552 | A1 | 3/2019 |
| CA | 3101381 | A1 | 11/2019 |
| CA | 3055856 | A1 | 4/2020 |
| CA | 3153080 | A1 | 4/2021 |
| CA | 2910561 | C | 7/2021 |
| CA | 2908740 | C | 10/2021 |
| CA | 2980976 | C | 3/2023 |
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |
| CN | 106999076 | B | 8/2017 |
| CN | 109185113 | A | 1/2019 |
| CN | 109219415 | A | 1/2019 |
| CN | 109689160 | A | 4/2019 |
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |
| CN | 112533673 | A | 3/2021 |
| CN | 112566694 | A | 3/2021 |

(56) References Cited

FOREIGN PATENT DOCUMENTS

| | | | |
|---|---|---|---|
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114366154 | A | 4/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 116507295 | A | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 113615098 | B | 9/2023 |
| CN | 114555247 | B | 9/2023 |
| CN | 116744856 | A | 9/2023 |
| CN | 116761554 | A | 9/2023 |
| CN | 109416907 | B | 10/2023 |
| CN | 117321444 | A | 12/2023 |
| CN | 117500437 | A | 2/2024 |
| CN | 117580499 | A | 2/2024 |
| CN | 111212606 | B | 3/2024 |
| CN | 113490459 | B | 5/2024 |
| CN | 118414127 | A | 7/2024 |
| CN | 112601498 | B | 9/2024 |
| CN | 118678921 | A | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 114287963 | B | 2/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 3723857 | A1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 4201342 | A1 | 6/2023 |
| EP | 2931132 | B1 | 7/2023 |
| EP | 3229695 | B1 | 7/2023 |
| EP | 4209178 | A1 | 7/2023 |
| EP | 4209179 | A1 | 7/2023 |
| EP | 4226864 | A1 | 8/2023 |
| EP | 4230121 | A2 | 8/2023 |
| EP | 4230146 | A1 | 8/2023 |

(56) References Cited

FOREIGN PATENT DOCUMENTS

| | | | |
|---|---|---|---|
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 4385428 | A1 | 6/2024 |
| EP | 3324836 | B1 | 9/2024 |
| EP | 3624732 | B1 | 11/2024 |
| EP | 4289415 | A4 | 1/2025 |
| EP | 4406484 | B1 | 1/2025 |
| EP | 3190958 | B1 | 2/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | S62144641 | A | 6/1987 |
| JP | H02104343 | A | 4/1990 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7292448 | B2 | 6/2023 |
| JP | 7299992 | B2 | 6/2023 |
| JP | 2023085350 | A | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7335367 | B2 | 8/2023 |
| JP | 2023116673 | A | 8/2023 |
| JP | 7340594 | B2 | 9/2023 |
| JP | 7346293 | B2 | 9/2023 |
| JP | 7351972 | B2 | 9/2023 |
| JP | 7352561 | B2 | 9/2023 |
| JP | 2023123676 | A | 9/2023 |
| JP | 2023134811 | A | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |

(56) References Cited

FOREIGN PATENT DOCUMENTS

| | | | |
|---|---|---|---|
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 2025013082 | A | 1/2025 |
| JP | 7641600 | B2 | 3/2025 |
| JP | 7643694 | B2 | 3/2025 |
| JP | 2025031814 | A | 3/2025 |
| KR | 102574559 | B1 | 9/2023 |
| KR | 102764982 | B1 | 2/2025 |
| KR | 20250019597 | A | 2/2025 |
| RU | 2589649 | C1 | 7/2016 |
| WO | WO94/06355 | A1 | 3/1994 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A8 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/106891 | A1 | 5/2022 |
| WO | WO2022/152724 | A1 | 7/2022 |
| WO | WO2022/152827 | A1 | 7/2022 |
| WO | WO2022/152828 | A1 | 7/2022 |
| WO | WO2022/228922 | A1 | 11/2022 |
| WO | WO2022/238058 | A1 | 11/2022 |
| WO | WO2022/238092 | A1 | 11/2022 |
| WO | WO2022/238229 | A1 | 11/2022 |
| WO | WO2022/238274 | A1 | 11/2022 |
| WO | WO2022/238276 | A1 | 11/2022 |
| WO | WO2022/238392 | A1 | 11/2022 |
| WO | WO2022/247242 | A1 | 12/2022 |
| WO | WO2022/258561 | A1 | 12/2022 |
| WO | WO2023/274899 | A1 | 1/2023 |
| WO | WO2023/275617 | A2 | 1/2023 |
| WO | WO2023/275771 | A1 | 1/2023 |
| WO | WO2023/012516 | A2 | 2/2023 |
| WO | WO2023/036742 | A1 | 3/2023 |
| WO | WO2023/052278 | A1 | 4/2023 |
| WO | WO2023/084307 | A1 | 5/2023 |
| WO | WO2023/104599 | A1 | 6/2023 |
| WO | WO2023/104841 | A1 | 6/2023 |
| WO | WO2023/110555 | A1 | 6/2023 |
| WO | WO2023/110556 | A1 | 6/2023 |
| WO | WO2023/110594 | A1 | 6/2023 |
| WO | WO2023/110607 | A1 | 6/2023 |
| WO | WO2023/117721 | A1 | 6/2023 |
| WO | WO2023/117821 | A1 | 6/2023 |
| WO | WO2023/117822 | A1 | 6/2023 |
| WO | WO2023/118080 | A1 | 6/2023 |
| WO | WO2023105288 | A1 | 6/2023 |
| WO | WO2023105290 | A1 | 6/2023 |
| WO | WO2023/131566 | A1 | 7/2023 |
| WO | WO2023/131574 | A1 | 7/2023 |
| WO | WO2023/135024 | A1 | 7/2023 |
| WO | WO2023/141653 | A2 | 7/2023 |
| WO | WO2023/152639 | A1 | 8/2023 |
| WO | WO2023/169967 | A1 | 9/2023 |
| WO | WO2023/180811 | A2 | 9/2023 |
| WO | WO2023/218428 | A1 | 11/2023 |
| WO | WO2023/230053 | A1 | 11/2023 |
| WO | WO2023/230054 | A1 | 11/2023 |
| WO | WO2024/009143 | A1 | 1/2024 |
| WO | WO2024/016088 | A1 | 1/2024 |
| WO | WO2024/040185 | A2 | 2/2024 |
| WO | WO2024/047580 | A1 | 3/2024 |
| WO | WO2024/092272 | A1 | 5/2024 |
| WO | WO2024/120659 | A1 | 6/2024 |
| WO | WO2024/125872 | A1 | 6/2024 |
| WO | WO2024/130252 | A1 | 6/2024 |
| WO | WO2024/148416 | A1 | 7/2024 |
| WO | WO2024/157226 | A1 | 8/2024 |
| WO | WO2024/163876 | A1 | 8/2024 |
| WO | WO2024/201441 | A1 | 10/2024 |
| WO | WO2024/208895 | A1 | 10/2024 |
| WO | WO2024/209347 | A1 | 10/2024 |
| WO | WO2024/209348 | A1 | 10/2024 |
| WO | WO2024/221001 | A2 | 10/2024 |
| WO | WO2024/235777 | A1 | 11/2024 |
| WO | WO2025/038127 | A1 | 2/2025 |
| WO | WO2025/059671 | A1 | 3/2025 |

OTHER PUBLICATIONS

Snell et al.; U.S. Appl. No. 18/886,807 entitled "Simulation software and tools for evaluating histotripsu therapy for a given pose and position of a therapy array," filed Sep. 16, 2024.

Schell et al.; U.S. Appl. No. 18/890,580 entitled "Co-registration techniques between computed tomography imaging systems and histrotripsy robotic systems," filed Nov. 14, 2024.

Kisting et al.; Imaging for targeting, monitoring, and assessment after histotripsy: a non-invasive, non-thermal therapy for cancer; Blood Vessels; vol. 10; pp. 15-21; Mar. 2023.

Kutlu et al.; A target containing phantom for accuracy assessment of cone?beam CT?guided histotripsy. Journal of Applied Clinical Medical Physics; 25(5); e1432; DOI: 10.1002/acm2.14329; 11 pages; Mar. 18, 2024.

Lu et al.; Transcranial MR-guided histotripsy system; IEEE transactions on ultrasonics, ferroelectrics, and frequency control; 68(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

(56) References Cited

OTHER PUBLICATIONS

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.
Wagner et al.; An X-ray C-arm guided automatic targeting system for histotripsy; IEEE Transactions on Biomedical Engineering; 70(2); pp. 592-602; Aug. 15, 2022.
Wijlemans et al.; Magnetic resonance-guided high-intensity focused ultrasound (MR-HIFU) ablation of liver tumours; Cancer Imaging; 12(2); pp. 387-394; Sep. 28, 2012.
Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.
Miller et al.; U.S. Appl. No. 18/924,812 entitled "Histotripsy systems and methods," filed Oct. 23, 2024.
International Society for Magnetic Resonance in Medicine (ISMRM); No. 105; XP040714022;I Jul. 24, 2020.
Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.
Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.
Stopek.; U.S. Appl. No. 18/761,937 entitled "Minimally invasive histotripsy systems and methods," filed Jul. 2, 2024.
Shaffer et al.; U.S. Appl. No. 18/832,708 entitled "Histotripsy systems and methods," filed Jul. 24, 2024.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
AVAGO Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bader et al.; For whom the bubble grows: physical principles of bubble nucleation and dynamics in histotripsy ultrasound therapy; Ultrasound in medicine & biology; 45(5); pp. 1056-1080; May 1, 2019.
BAK; Rapid protytyping or rapid production? 3D printing processes move industry towards the latter; Assembly Automation: 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+-PowerMOSFETS+-+600V+CoolMOS%E284%A2+-+CP+Most+beneficial+use+of+superjunction+technologie+devices.pdf?folderid=db3a304412b407950112b408e8c90004&fileId=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain et al.; Concentric-ring and sector-vortex phased-array applicators for ultrasound hyperthermia; IEEE Transactions on Microwave Theory and Techniques; 34(5); pp. 542-551; May 1986.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-LI Blockade; Cancer Research: 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Gateau et al.; Transcranial ultrasonic therapy based on time reversal of acoustically induced cavitation bubble signature. IEEE Transactions on Biomedical Engineering; 57(1); pp. 134-144; Sep. 18, 2009.
Giannatsis et al.; Additive fabrication technologies applied to medicine and health care: a review, The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.

(56) References Cited

OTHER PUBLICATIONS

Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle vol. fraction on sound velocity and attenuation of EPDM composites; Ultrasonics, vol. 46, pp. 177-183, Feb. 2007.
Kim et al.; Development of a wearable robotic positioning system for noninvasive transcranial focused ultrasound stimulation. IEEE/ASME Transactions on Mechatronics; 21(5); pp. 2284-2293; Jun. 13, 2016.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al.; Effect of Radial Displacement of Lens on Response of Focused Ultrasonic Transducer; Japanese Journal of Applied Physics, vol. 46, p. 3077-3085; May 15, 2007.
Maréchal et al.; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84, Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer; 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.

(56) References Cited

OTHER PUBLICATIONS

Roy et al.; A precise technique for the measurement of acoustic cavitation thresholds and some preliminary results; Journal of the Acoustical Society of America; vol. 78(5), pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-Invasive Ultrasonic Tissue Fraction for Treatment of Benign Disease and Cancer—“Histotripsy”. University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Wu et al.; Mechanism and dynamics of hydrodynamic-acoustic cavitation (HAC); Ultrasonics sonochemistry; vol. 49., pp. 89-96; Dec. 1, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America, vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Cannata et al.; U.S. Appl. No. 18/311,050 entitled “Histotripsy systems and methods,” filed May 2, 2023.
Duryea et al.; U.S. Appl. No. 18/498,979 entitled “Histotripsy systems and methods,” filed Oct. 31, 2023.
Cannata et al.; U.S. Appl. No. 18/630,758 entitled “Histotripsy systems and methods,” filed Apr. 9, 2024.
Xu et al.; U.S. Appl. No. 18/568,038 entitled “Minimally invasive histotripsy systems and methods,” filed Dec. 7, 2023.
Xu et al.; U.S. Appl. No. 18/568,045 entitled “All-in-one ultrasound systems and methods including histotripsy,” filed Dec. 7, 2023.
Cannata et al.; U.S. Appl. No. 18/594,843 entitled “Histotripsy systems and methods,” filed Mar. 4, 2024.

* cited by examiner

200

200

300

300

500

500

700

700

704

730

700

704

730

700

700

700

1100

1100

1100

1100

1100

1100

1100

1100

1100

1100

1100

1100

1100

1100

1100

1100

1100

1100

HISTOTRIPSY SYSTEMS AND ASSOCIATED METHODS INCLUDING USER INTERFACES AND WORKFLOWS FOR TREATMENT PLANNING AND THERAPY

PRIORITY CLAIM

This patent application claims priority to U.S. provisional patent application No. 63/497,277, titled "HISTOTRIPSY SET-UP AND PLANNING SYSTEMS AND METHODS", and filed on Apr. 20, 2023, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates to histotripsy systems configured to produce acoustic cavitation, methods, devices, and procedures for the minimally and non-invasive treatment of healthy, diseased and/or injured tissue. The histotripsy systems and methods described herein may include transducers, drive electronics, positioning systems including robotics, imaging systems, patient coupling systems, and integrated treatment planning and control software to provide comprehensive treatment and therapy for soft and/or hard tissues in a patient. In particular, soft tissues such as organs or structures found within the abdominal cavity (e.g., liver, kidney, spleen, pancreas, stomach, colon, small intestine), pelvic and reproductive tissues/organs (e.g., prostate, uterus), lungs, brain, esophagus, muscles, tendons/ligaments, hard tissues such as bone, external tissues such as dermis/skin and tissues found on, and/or partially within skin surface, implants, medical devices, are envisioned for use with Histotripsy treatment and therapy.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm, it is necessary to deliver acoustic energy in the form of high amplitude very short acoustic pulses, typically with low duty cycle.

Compared with conventional focused ultrasound technologies, histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, high-intensity focused ultrasound (HIFU) cryo or radiation, Histotripsy relies on the mechanical action of cavitation for tissue destruction and not on heat, cold or ionizing energy. Despite these clear advantages improvements in methods and systems are always desired.

SUMMARY

One aspect of the disclosure is directed to a histotripsy system including an ultrasound imaging probe; an ultrasound therapy transducer coupled to the ultrasound imaging probe. The histotripsy system also includes a robotic arm configured to orient the ultrasound imaging probe and the ultrasound therapy transducer about a patient; a display operably connected to imaging probe; a memory, storing thereon instructions that when executed by a processor operably connected to the memory: receive live ultrasound images from the ultrasound imaging probe; present the live ultrasound images on a user interface in the display; receive via the user interface an input to alter a shape of a treatment contour around a treatment area in the live ultrasound images; present a contour line representative of the treatment contour on the ultrasound images in the user interface; receive via the user interface an input of a size of a margin around the treatment area; present a margin line representative of the margin on the ultrasound images in the user interface; determine survey points at locations where X, Y, and Z axes bisect the margin line in an XZ plane and a YZ plane; receive an input to drive the ultrasound therapy transducer to a location where a focal point of the ultrasound therapy transducer is at one of the survey points, and determine whether resistance to movement of the ultrasound therapy transducer exceeds a threshold. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The histotripsy system where receipt via the user interface of an input to alter the shape of the treatment contour around a treatment area occurs in live ultrasound images in the XZ plane and in the YZ plane. The input to drive the ultrasound therapy transducer is received via the user interface in the display. The input to drive the ultrasound therapy transducer is received for each survey point. Upon determination that the resistance to movement of the ultrasound therapy transducer in driving to reach all of the survey points does not exceed a threshold, a planned therapy is accepted and stored in the memory. Upon determination that the resistance to movement of the ultrasound therapy transducer in driving to reach any of the survey points exceeds a threshold, the instructions stored in memory and executed by the processor cause the user interface to present mitigation instructions. The histotripsy system further including presenting a representation of the contour line and the survey points in a separate field in the user interface. The input to drive the therapy transducer is received via the representation of the contour line and survey points in the separate field in the user interface. The indicator is depicted upon movement of the therapy transducer to a location at which the focal point coincides with the survey point. The instructions when executed by the processor receive in input of a location of an intersection of a muscle layer and a fat layer in the live ultrasound images. The instructions when executed by the processor cause activation of knobs which when manipulated adjust a parameter displayed in an indicator on the user interface. The knobs adjust the contour along the x, y, and z axes. The knobs adjust the size of the margin around the contour. The knobs adjust the focal point of the therapy transducer. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method of planning a histotripsy procedure. The method includes displaying live ultrasound images on a user interface. The method also includes moving an ultrasound assembly to a mark on a patient from which a treatment area within the patient can be observed in the live ultrasound images; presenting a contour line around a treatment area in the live ultrasound images on the user interface; adjusting the contour line in the live ultrasound images; identifying survey points where X, Y, and Z axes intersect the contour line in XZ plane and the YZ plane; displaying a margin around the contour line; displaying a focal point of an therapy transducer, where the therapy transducer is a component of the ultrasound assembly; driving the ultrasound assembly such that the focal point of the therapy transducer coincides with at least one of survey points; and detecting a resistance to movement of the ultrasound assembly as it moves to reach the at least one survey point. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including comparing the resistance to movement to a threshold. The method further including altering a shape of the contour line around a treatment area in the live ultrasound images in the XZ plane and in the YZ plane. The ultrasound assembly is robotically driven to each survey point. Upon determination that the resistance to movement of the therapy transducer in driving to reach each of the survey points does not exceed a threshold, a planned therapy is accepted and stored in a memory. The method further including receiving in indication of a location of an intersection of a muscle layer and a fat layer in the live ultrasound images. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one aspect, a histotripsy system is provided, comprising: an ultrasound imaging system; an ultrasound therapy transducer coupled to the ultrasound imaging system; a robotic arm configured to position the ultrasound imaging system and the ultrasound therapy transducer with respect to a patient and a treatment location, a display operably connected to the ultrasound imaging system; a memory, storing thereon instructions that when executed by a processor operably connected to the memory: receive real-time ultrasound images from the ultrasound imaging system; present the live ultrasound images on a user interface in the display; identify a target; receive via the user interface an input to alter a shape of a target contour around a treatment volume in the live ultrasound images; present a target contour line representative of the target contour on the ultrasound images in the user interface, receive via the user interface an input of a size of a margin around the target area; present a margin contour line representative of the margin contour on the ultrasound images in the user interface; determine survey points at locations where X, Y, and Z axes bisect the margin line in an XZ plane and a YZ plane, receive an input to drive the ultrasound therapy transducer to a location where a focal location of the ultrasound therapy transducer is at one of the survey points; and determine whether resistance to movement of the ultrasound therapy transducer exceeds a threshold.

In some aspects, receipt via the user interface of an input to alter the shape of the treatment contour around a treatment volume occurs in live ultrasound images in the XZ plane and in the YZ plane.

In some aspects, the input to drive the ultrasound therapy transducer is received via the user interface in the display.

In one aspect, the input to drive the ultrasound therapy transducer is received for each survey point.

In some aspects, upon determination that the resistance to movement of the ultrasound therapy transducer in driving to reach all of the survey points does not exceed a threshold, a planned therapy is accepted and stored in the memory.

In one aspect, upon determination that the resistance to movement of the ultrasound therapy transducer in driving to reach any of the survey points exceeds a threshold, the instructions stored in memory and executed by the processor cause the user interface to present mitigation instructions.

In some aspects, the system includes presenting a representation of the contour line and the survey points in a separate field in the user interface.

In another aspect, the input to drive the therapy transducer is received via the representation of the contour line and survey points in the separate field in the user interface.

The histotripsy system of claim 7, further comprising an indicator depicted on the survey point of the representation in the separate field on the user interface, wherein the indicator is depicted upon movement of the therapy transducer to a location at which the focal point coincides with the survey point.

In some aspects, the instructions when executed by the processor receive in input of a location of an intersection of a muscle layer and a fat layer in the live ultrasound images.

In other aspects, the instructions when executed by the processor cause activation of knobs which when manipulated adjust a parameter displayed in an indicator on the user interface.

In some aspects, the knobs adjust the contour along the X, Y, and Z axes.

In other aspects, the knobs adjust the size of the margin around the contour.

In some aspects, the knobs adjust the focal location of the therapy transducer.

A method of planning a histotripsy procedure is provided comprising: displaying live ultrasound images on a user interface; moving an ultrasound assembly to a mark on a patient from which a treatment area within the patient can be observed in the live ultrasound images; presenting a contour line around a treatment volume in the live ultrasound images on the user interface; adjusting the contour line in the live ultrasound images; identifying survey points where X, Y, and Z axes intersect the contour line in XZ plane and the YZ plane; displaying a margin around the contour line; displaying a focal point of a therapy transducer, wherein the therapy transducer is a component of the ultrasound assembly; driving the ultrasound assembly such that the focal point of the therapy transducer coincides with at least one of survey points; and detecting a resistance to movement of the ultrasound assembly as it moves to reach the at least one survey point.

In some aspects, the method includes comparing the resistance to movement to a threshold.

In other aspects, the method comprises altering a shape of the contour line around a treatment area in the live ultrasound images in the XZ plane and in the YZ plane.

In some aspects, the ultrasound assembly is robotically driven to each survey point.

In one aspect, upon determination that the resistance to movement of the therapy transducer in driving to reach each of the survey points does not exceed a threshold, a planned therapy is accepted and stored in a memory.

In some aspects, the method includes receiving in indication of a location of an intersection of a muscle layer and a fat layer in the live ultrasound images.

A method of histotripsy treatment is provided comprising: navigating a therapy transducer to align a focal point with a center of a planned treatment volume; activating histotripsy pulses; increasing a voltage associated with histotripsy pulses until bubble cloud/acoustic cavitation forms; marking a center of the bubble cloud; navigating the therapy transducer to a plurality of survey points about the planned treatment volume, wherein at each survey point the voltage associated with histotripsy pulses is activated and increased until a bubble cloud forms/is created; and initiating an automatic treatment plan, wherein the therapy transducer is robotically driven to a plurality of focal locations within the planned treatment volume and the histotripsy pulses is applied at each focal location.

In some aspects, the method includes interpolating an ultrasonic energy required for each focal location based on the voltage applied at each of the survey points and the center of the planned treatment volume.

In one aspect, the therapy transducer is driven to each focal location in a sequential pattern until all focal locations within the planned treatment volume has received an individualized histotripsy pulses.

In another aspect, the bubble cloud formed at each survey point is confirmed to coincide with the focal point of the therapy transducer.

In some aspects, following completion of the automatic treatment plan, deactivating a voltage knob associated with a source of the therapeutic energy.

In another aspect, the method includes confirming that all focal locations have received histotripsy pulses.

In some aspects, the method includes visualizing the planned treatment volume after completing the treatment plan to confirm complete treatment.

In one aspect, the visualization is performed with an ultrasound imaging probe.

In another aspect, a first survey point of the plurality of survey points to which the therapy transducer is navigated is a −Z survey point.

In one aspect, the method includes calculating an offset of the center of the bubble cloud and a focal point of the therapy transducer.

In some aspects, the method comprises utilizing the offset to calibrate placement of the therapy transducer to arrive at each survey point.

In some aspects, the method comprises displaying on a user interface the automated treatment plan, wherein the automated treatment plan defines one or more of a volume to be treated a depth of plan, and a margin.

In one aspect, a user interface displays an indication of treatment each focal location of the planned treatment volume following application of histotripsy pulses to the focal location.

In some aspects, the user interface displays an indication of which focal locations in the planned treatment volume is currently receiving histotripsy pulses.

In one aspect, the method includes a user interface displaying an ultrasound image acquired by an ultrasound imaging transducer, the ultrasound image depicting at least a portion of the planned treatment volume.

In some aspects, upon application of the histotripsy pulses the bubble cloud is viewable in the ultrasound image.

In one aspect, the method further comprises depicting one or more of a focal point, the planned treatment volume, a margin, or an acoustic field of the therapy transducer on the ultrasound image.

In some aspects, ultrasound imaging continues throughout the automatic treatment plan such that visualization of histotripsy pulses to each focal location is visualized.

In one aspect, the ultrasound images are fused ultrasound images depicted in combination with preprocedural image sets.

In some aspects, the method further comprises detecting a resistance to movement of the therapy transducer and displaying an indicator of the resistance on a user interface.

A method of fusing images is provided comprising: navigating a combined imaging and treatment transducer assembly to a location on a patient enabling visualization of a region of interest; performing an ultrasound sweep using the imaging transducer of the combined imaging and treatment transducer assembly to capture a volume of ultrasound images; marking a registration point in an ultrasound image from the ultrasound sweep; marking a registration point in an image from a preprocedural image set; fusing the preprocedural image set with the ultrasound images from the ultrasound sweep to form fused images; reviewing fused images; accepting a fusion; an displaying on a user interface live ultrasound images fused with the preprocedural image set.

In one aspect, the method includes verifying the combined imaging and therapy transducer assembly is approximately centered over the region of interest in multiple planes.

In some aspects, the method comprises marking a plurality of registration points in images from the ultrasound sweep and a plurality of registration points in the preprocedural image set.

In one aspect, the method further comprises initiating a breath hold of the patient prior to performing the ultrasound sweep.

In some aspects, the method comprises adjusting orientation and position of the combined imaging and therapy transducer assembly to optimize visualization of a region of interest with the imaging transducer.

In another aspect, the method comprises rotating the imaging transducer of the combined imaging and therapy transducer assembly 90 degrees to confirm visualization of the region of interest.

In some aspects, the method comprises displaying the ultrasound images captured during the ultrasound sweep.

In one aspect, the method comprises editing the ultrasound images captured during the ultrasound sweep.

In some aspects, the images remaining after editing of the images are only those images depicting a region of interest.

In another aspect, the registration point placed in the ultrasound images corresponds to the registration point in the preprocedural image set and are placed at an anatomical landmark appearing in both the ultrasound image and the preprocedural image set.

In some aspects, the method comprises determining whether sufficient anatomical landmarks have been identified in the ultrasound image and the preprocedural image set.

In another aspect, the system comprises placing at least one registration point in a plurality of ultrasound images, and at least one registration point in multiple images of the preprocedural image set.

In some aspects, the method includes adjusting a position of the registration point in the ultrasound image or a position of the registration point in the preprocedural image set.

In some aspects, the method includes adjusting the registration of the images from the ultrasound sweep with the preprocedural image set by dragging or rotating at least one image of the preprocedural image set relative to an image of the ultrasound sweep.

In other aspects, the method comprises verifying an alignment of anatomy of the patient in the live ultrasound images and the preprocedural image set.

In one aspect, the method includes rotating the imaging transducer of the combined imaging and therapy transducer assembly 90 degrees to verify the alignment.

In another aspect, the method includes adjusting the displayed live ultrasound images fused with the preprocedural image set.

A system is also provided that is configured for use according to method claims described above.

A method of planning a histotripsy therapy is provided comprising: visualizing a target treatment volume with an ultrasound imaging system in a first plane; displaying a target contour around the treatment volume in an ultrasound image generated by the ultrasound imaging system; adjusting the target contour around the treatment volume in the first plane; confirm that an acoustic pathway of a therapy transducer is substantially free of obstructions in the first plane; visualizing the target treatment volume with the ultrasound imaging system in a second plane; displaying the target contour around the treatment volume in a second ultrasound image generated by the ultrasound imaging system; adjusting the target contour around the treatment volume in the second plane; and confirm that the acoustic pathway of the therapy transducer is substantially free of obstructions in the second plane.

In some aspects, the target contour in the first plane and the target contour in the second plane define a volume for treatment.

In another aspect, the method includes displaying a margin around the treatment volume.

In some aspects, the method comprises defining a plurality of survey points of the treatment volume.

In some aspects, the survey points are located at a center of the treatment volume and at points along three orthogonal axes extending outward from the center of the treatment volume where the axes intersect the margin.

In one aspect, the axes are X, Y, and Z.

In other aspects, the first plane is an YZ plane.

In some aspects, the second plane is an XZ plane.

In another aspect, adjusting the target contour in the first plane defines a diameter of the treatment volume along the Y axis and a diameter of the treatment volume along the Z axis.

In some aspects, the method comprises confirming the target contour in the first plane is centered in the YZ plane and the target contour in the second plane is centered in the XZ plane.

In one aspect, the method comprises receiving a selection of one of the survey points.

In some aspects, the method comprises robotically driving the therapy transducer to the selected survey point.

In some aspects, the method further comprises detecting resistance to movement of the therapy transducer while moving to the selected survey point.

In some aspects, if a value of the detected resistance exceeds a threshold an indicator or the threshold is depicted.

In another aspect, the method includes detecting whether a value of resistance exceeds a second threshold and stopping robotic movement of the therapy transducer.

In one aspect, the method further comprises adjusting one of target contour or margin of the treatment volume or focal point of the therapy transducer and driving to the survey point.

In some aspects, the method comprises receiving confirmation that all survey points have been driven to.

In another aspect, the method includes receiving via a user interface an indication of a location of an intersection of a muscle layer and a fat layer.

In some aspects, the method comprises receiving a verification that the treatment volume is within the target contour in the first plane and the target contour in the second plane throughout a breathing cycle.

In some aspects, a coupling medium level in a coupling container in which a therapy transducer is located is sufficient to ensure ultrasound coupling at all survey points.

DETAILED DESCRIPTION

Figure 1A:
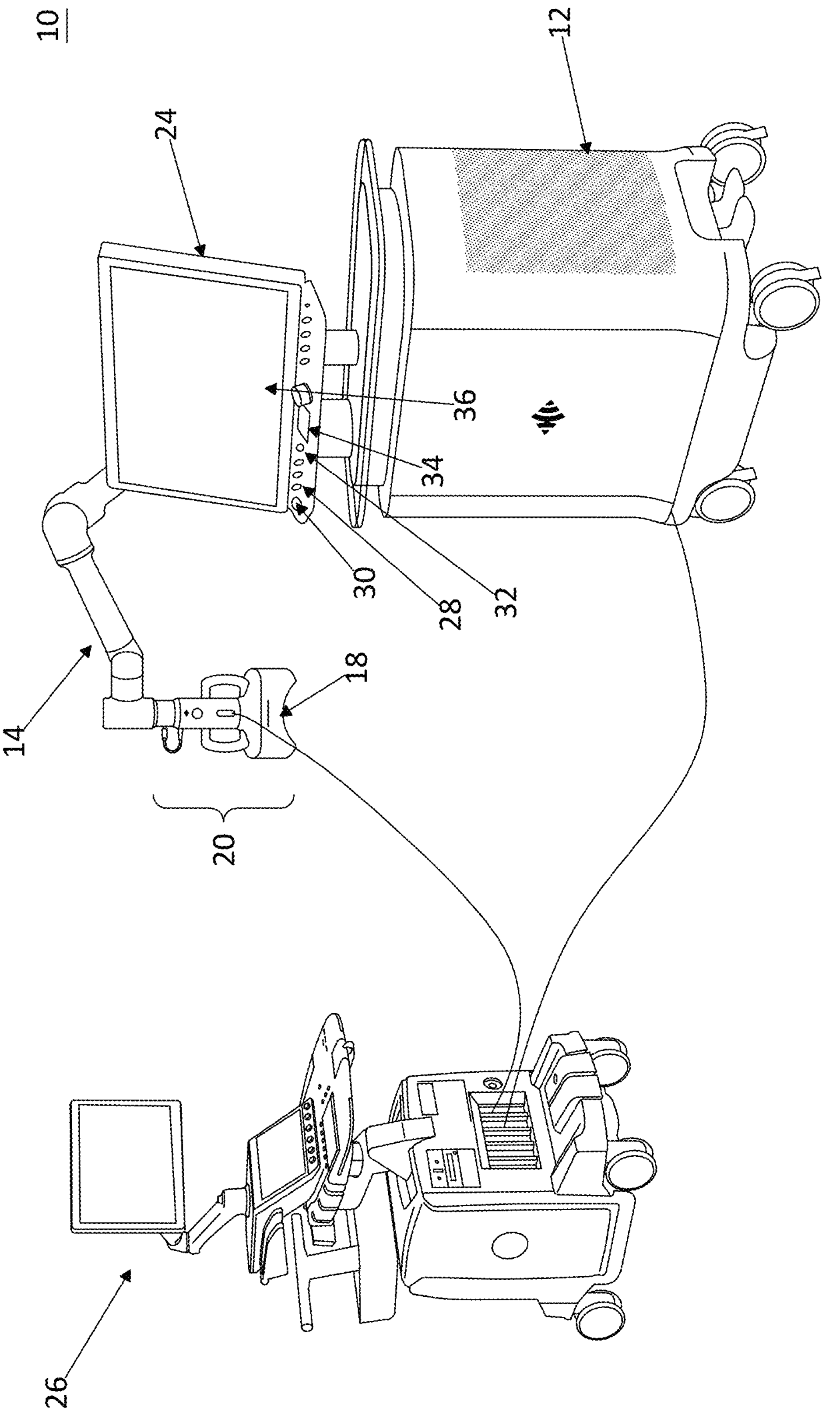
FIGS. 1A-1B depict a histotripsy system in accordance with the disclosure.

This disclosure is directed to systems and methods for histotripsy and histotripsy systems In accordance with the disclosure, one aspect is directed to systems and methods of confirming placement of a treatment head assembly including a focused ultrasound therapy transducer (e.g., histotripsy therapy transducer) exterior to the patient and positioned in alignment with a region of interest comprising target tissue and a planned treatment volume. In some embodiments, the system is configured with features to aid in localizing, targeting, and verifying that the target tissue within the planned treatment volume is visible under ultrasound images prior to commencement of the therapy delivery phases of the procedure In other embodiments, tracked ultrasound imaging may be used to register secondary imaging modalities (e.g., CT, MRI, CBCT, contrast enhanced ultrasound, etc.) with the live ultrasound images to further enrich the visualization of region of interest and target tissue. By these methods, the systems described herein can be placed and configured such that energy obstruction or absorption by tissues (e.g., bone or bowel gas) is minimized or avoided thus reducing the energy required for initiating or maintaining histotripsy therapy as well as mitigating injury to prefocal and intervening tissue. In addition, forces applied to the patient or to a therapy assembly is measured, monitored, and reacted to (if needed) to maintain acceptable safety levels throughout the duration of the procedure. These system features are designed to ensure the safety of the patient, system and system components are maintained. In addition, these system features ensure that the anatomy, organs and other soft tissues of interest are not moved or altered in an unacceptable way during the procedure. Further, based on unique and heterogeneous patient specific treatment scenario(s) given the varied location, size, and tissue pathway to targeted tissue locations, and patient specific variables (body mass index, anatomy, etc.), an in situ treatment plan is developed for a user defined 3D planned treatment volume ensuring complete therapy is delivered to the treatment volume, including a user defined margin, and as delivered using a specific treatment pattern and pathway as the system moves through the plan and delivers one or more histotripsy pulse sequences at one or more treatment zones and defined focal locations.

Histotripsy

Histotripsy comprises short, high amplitude, focused ultrasound pulses to generate a dense, energetic, "bubble cloud," capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with at least a single negative/tensile phase sufficient to cause a cluster of bubble nuclei intrinsic to the medium to undergo inertial cavitation, 2) Shock-Scattering Histotripsy: Delivers pulses of about 3-20 cycles in duration. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) media and tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such. This further includes the ability to vary these parameters, spatially and temporally, throughout treatments and treatment plans.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined. Additionally, the imaging component or probe may be co-registered to the robotic system to accurately locate/display the focus of the therapy system in the context of images from one or more imaging components or probes.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automatically, or fully automatically image the patient (e.g., by hand or using a robotically-enabled imager). In some embodiments, the robotic system can sweep the onboard ultrasound system (e.g., linear and/or angular sweeps) across a target volume to generate volumetric imaging data.

The user may be allowed to further select, annotate, mark, highlight, and/or contour, various regions of interest or treatment sites, and defined treatment targets (on the image (s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses. The system may also various settings or modes of viewing visualization features (e.g., marks, contours, and/or other overlays) including toggling them on and/or off, etc.

The system may further include the ability to conduct image registration, including imaging and image data set registration to allow navigation and localization of the system to the patient, including the treatment site (e.g., tumor, critical structure, bony anatomy, anatomy and identifying features of, etc.). In one aspect, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's therapy and robotics components to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and robotics components tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci multi and single port systems) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Components disclosed herein may also comprise all or some of their component hardware packaged within the other system (e.g., cart, computing device, memory, etc.).

The system may also be configured, through various aforementioned parameters and other parameters, to display real-time visualization of a bubble cloud in a spatial-temporal manner, including the resulting tissue effect peri- or post-treatment from tissue to bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), or where the other procedure further require invasive approaches (e.g., incisions or punctures) and iterative imaging in a scanner between procedure steps (e.g., CT or MRI scanning). The above components, modalities, features and work-flows and methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Software

The system may comprise various software applications, features and components which allow the user to interact, control and use the system for a plethora of clinical applications. The Software may communicate and work with one or more of the components including but not limited to therapy, integrated imaging, robotics and other components, ancillaries and accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and may be used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. The threshold points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the robotics components, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Treatment Patterns and Pathways

A variety of treatment patterns and pathways may be utilized to position the bubble cloud in one or more desired focal locations within a target tissue volume as part of a treatment plan. Patterns may comprise one or more focal locations of specified location in 2D and 3D space, including configurable pattern variables including, but not limited to, the location, spacing, and/or defined overlap (minimum and/or maximum) of focal locations. This may further include the groupings of focal locations into various desired shapes (e.g., columns, ellipses, layers, etc.), wherein the shapes can be packed/placed into a larger volume. For example, an ellipsoidal volume comprised of radial layers (of packed focal locations) or in contrast, an ellipsoidal volume comprised of rectilinear columns. Patterns may comprise unlimited features and variations when considering the size of the treatment volume, bubble cloud configuration (size) and position (placement of the bubble cloud/focal location) in a treatment volume (centered, off-center, similar or varied center to center alignment/orientation, etc.).

In terms of "pathways", these may comprise various techniques for motioning and moving the bubble cloud through the selected or defined pattern. In some embodiments, this may comprise moving to the next nearest point in the pattern. In other embodiments, it may comprise moving to a preferred position in the plan that is at a distance from the current focal location (e.g., two or more focal locations away) In some configurations, the pathway may comprise moving to the farthest focal location. Pathways may be configurable based on, for example, desired cooling profiles.

In some embodiments and system configurations, this may include a linear pattern and pathway that traverses a spherical treatment volume in a series of axial slices (parallel to the imaging plane), beginning with the center slice within the treatment volume and progressing outward in the positive x-dimension (relative to the transducer array) until the entire +x-half of the spherical treatment volume is treated. The treatment then moves to the untreated slice adjacent to the center and treats the remaining half of the spherical volume in an analogous manner, in this case progressing outward in the negative x-dimension. Within each slice, treatment may start at the center point and moves outward in a spiraling fashion.

A "Top-Down" and "Bottom-Up" patterns and pathways differ from other rectilinear patterns in that they do not traverse the treatment volume in axial slices; rather, the robotic system is configured to move the transducer array focus to progress through the treatment volume in a series of lateral slices (i.e., slices perpendicular to the acoustic axis of the therapy transducer). Within each slice, treatment starts at the center point and moves outward in a spiraling fashion (identical to the manner in which a representative rectilinear pattern traverses an axial slice). As the names imply, the "Top-Down" and "Bottom-Up" patterns progress through the lateral planes of the sphere from the upper-most (closest to the transducer) to the distal-most (farthest from the transducer) or distal-most to upper-most, respectively.

In another configuration, the pattern and pathway may comprise a target tissue volume that is divided into a number of slices, which are treated in alternating order starting from the middle of the volume (number below each slice indicates treatment order). Within each slice columns are treated in an alternating fashion (number below each column indicates treatment order). The columns themselves can be traversed in a top-down or a bottom-up manner, and/or combination of, depending on the treatment type, tissue, type, and tissue location.

Other patterns and pathways may represent variations of these patterns. In one example, the spherical volume is still traversed in a set of axial slices parallel to the imaging plane, and the progression of treatment within each slice remains the same. Only the order in which the axial slices are treated is varied in these two schemes. Specifically, in one embodiment, pattern and pathway treats the axial slices starting at one lateral extreme of the volume (e.g., the slice farthest in the +x-dimension) and progresses through slices one at a time until reaching the other lateral extreme of the volume (the slice farthest in the −x-dimension). In another configuration, the pattern and pathway increments through slices in a strategic order selected to maximize the spatial distribution/distance of successive treatment slices. If the center axial slice of the sphere is defined as slice 0, the slice farthest in the +x-dimension as 6, and the slice farthest in the −x-dimension as −6, then in this example, treatment progresses through the 13 slices comprising the 3 cm sphere in the following order: 0, 4, −2, −5, −1, 6, −3, 5, 1, −6, 3, −4, 2.

In one "Spiral In-Out" pattern and pathway example, treatment occurs by traversal through the spherical volume in a series of radial layers, from the center of the sphere outward. Within each layer, and when transitioning between layers, the points are treated in order of proximity (i.e., the next treatment point is the closest untreated point in the current radial layer, or the closest point in the next radial layer when transitioning between layers). In some embodiments, the pattern can move in a spiral or circular movement throughout each layer. When a given layer is completed, the pattern can transition to the next layer, typically the closest layer in the given propagation direction. The spiral patterns described herein can treat from the distal most layer to the proximal most layer (respective to the transducer) or vis versa.

Combinations of pattern and pathway traversal are also included. In particular, combinations of the "Spiral In-Out" and "Bottom-up" are envisioned, wherein the distal-most layer is treated first in a pattern spiraling generally outward, from an interior treatment point. Transitioning between layers in a distal to proximal fashion, while generally treating an interior treatment point initially within each new layer, before progressing to the outward treatment points.

In other examples, the size of the cavitation or bubble cloud at a given focal location can be increased or enhanced with rapid electronic steering techniques that rapidly steer between multiple points at or intersecting with a given focal location. This technique can be referred to herein as "bubble saber". The "bubble saber" or column shape end effector can be implemented by rapidly electronically steering the bubble cloud focus in any direction (e.g., in the z-direction, in the x-y direction, in 3D space) through an enhanced volume of treatment points and defined steering distance, and optionally repeating the rapid electronic steering multiple times. In some embodiments, this configuration may enable the user to manipulate the bubble saber position via the robot and software to treat a defined treatment area. This may include treating tissue for the application of creating a treatment plane (across an organ and/or anatomic structure, e.g., a fissure, an organ segment boundary, and/or a desired resection plane, etc.). In some cases, this may be enabled as a linear end-effector (z-axis only). In other configurations, including those enabling 3D electronic steering, the end-effector may include non-linear shapes (e.g., arc).

The "bubble saber" technique can also provide a large thermal benefit by electronically steering the bubble cloud to a more proximal location than the geometric focus to ablate shallower targets. The primary thermal benefit of the "bubble saber" technique comes from the electronic steering itself (utilization of the lowest possible effective f number). Another benefit of the "bubble saber" is the reduced impact of motion on local dose, and the potential efficacy benefits of a more parallel treatment strategy (providing some protection against untreated volumes of tissue moving or shifting to a previously treated area as a result of treatment in surrounding areas and thereby escaping further treatment). In some embodiments, the "bubble saber" may comprise a linear end-effector, in in some configurations, it may comprise an arc or curved end-effector, based on the desired treatment plan/plane.

In another embodiment, histotripsy therapy can be applied in a "radial spiral" pattern that minimizes the distance between treatment columns while maintaining an "inside-out" lesion development in tissue instead of columns of treatment points arranged in a cartesian grid of locations, the treatment points in this technique are arranged in radial layers. These layers are then treated from inside out, with columns within each layer treated sequentially around each ring in a spiral (or alternating from side to side if preserving the thermal benefit of sequential treatment columns being are distant as possible is required). This pattern provides a more consistent cloud overlap in three-dimensions and minimized the distance between successive treatment columns compared to a rectilinear treatment pattern, resulting in a planned ablation volume that more closely matches ellipsoidal planning contours.

The radial spiral technique allows the flexibility to reduce treatment times by removing the de facto cooling time when moving between spatially distant treatment columns. Though that this pattern does not remove the need for this cooling time, it allows the flexibility to include or exclude cooling time only as required by the anticipated thermal load, i.e., the option to go faster if thermally tolerable. The radial spiral may proceed in a clock-wise or counter-clock-wise direction.

A planned bubble cloud treatment treats a specified percentage of the target tissue volume. In some examples, it is desirable for a chosen pattern to cover completely or nearly the entire tissue volume. In some embodiments, the pattern can be implemented to cover 90-100% of the target tissue volume. In other examples, it may be desirable to treat only 50% or less of a given volume. The amount or percentage of treatment may depend on the tissue type, tissue location, etc. Focal location center points for each bubble cloud may be distributed at discrete spacing in X and Y, with any points outside the tissue volume boundary discarded. Point positions in Z may also be dynamically adjusted to match the tissue volume boundary contour. The spacing between adjacent focal locations may be adjusted to determine the amount, if any, of overlap between focal locations. In one example, focal location center points for each bubble cloud may be distributed in radial layers in X and Y, with radii dynamically adjusted to match the target tissue volume boundaries. Focal location positions in Z may also dynamically adjusted to match the target tissue volume boundary contours.

Threshold Testing

As described above, the systems described herein include the capability to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. During treatment planning or during therapy, cavitation threshold test pulses can be transmitted into a plurality of locations of interest. The number of test locations of interest can be chosen based on the size and/or shape of the treatment region. For example, in a spherical treatment region benefits from at least seven test locations to probe the extremes of the spherical volume, these may include the center of the treatment area or treatment volume and axes end points where each of the X, Y, and Z axes intersect the boundary of the treatment area or treatment volume.

During therapy, the cavitation threshold at each of the locations of interest can be evaluated with a test series of pulses at an initial driving voltage and pulse repetition frequency (PRF) to determine if cavitation has formed before incrementing the driving voltage or to the next PRF. PRF may be defined as the number of pulses delivered every second by the systems described herein. PRF can be adjusted during therapy depending on the cavitation threshold, the tissue type, depth, etc. The formation (or not) of cavitation can be observed in real-time with imaging such as ultrasound imaging. In general, the driving voltage required to initiate a vigorous bubble cloud in tissue decreases as the PRF increases. The cavitation threshold in the tissue can also vary as a treatment procedure progresses. Thus, testing various points of interest within a treatment volume for treatment can be a useful tool to evaluate the cavitation threshold(s) and adjust the PRF or driving voltage of the therapy pulses to optimize treatment at each of the tested locations. The treatment protocol itself can then be adjusted based on the test pulses to utilize variable driving voltages or PRF based on the test results to ensure the optimal amount of energy is delivered into each location of the tissue for histotripsy therapy. Additionally, the depth at each of the test locations can be measured or determined (either manually or automatically with the system) to provide additional information to the system for determining optimal treatment parameters.

In some embodiments, the test locations can be used to determine a maximum amount of energy that may be applied without generating undesired damage to the test location or surround or intervening tissues. For example, while determining the cavitation thresholds at each of the test locations, the drive voltage or PRF of the system can be increased until cavitation is observed under real-time imaging and/or other feedback mechanisms. In some embodiments, the drive voltage or PRF can be increased until undesirable damage to the test location or cavitation or thermal damage to other locations outside of the test location are observed. This can be used to determine the maximum amount of energy that can be applied for a given test location.

Based on the test protocol and tested cavitation thresholds, the appropriate driving voltage for each point in the treatment grid can be chosen. With the required voltage at the center and six extremes of the target volume serving as inputs, the voltages for the remaining points comprising the treatment volume can be interpolated. The driving voltage can then be adjusted automatically by the software as the therapy progresses through the automated treatment volume. In this way each point is ablated using an amplitude sufficient to maintain an efficacious bubble cloud, but not overly so in order to minimize the thermal deposition in the acoustic path.

For example, a method of delivering histotripsy therapy to tissue can comprise delivering histotripsy pulses into tissue at a plurality of target test locations and imaging the test location in real-time to evaluate whether cavitation has formed at the test locations. If cavitation has not formed at the test locations, the driving voltage or the PRF of the histotripsy pulses can be adjusted, and histotripsy pulses with the adjusted parameters can be delivered into the tissue at the test locations. Real-time imaging can again be used to evaluate whether cavitation has formed at each test location. This process can be repeated until the cavitation threshold at each test location is determined, and a high-density map can be created based on various algorithms to extrapolate thresholds across the targeted region of interest/treatment volume, specific to the acoustic pathway and target depth. For example, if cavitation thresholds are known at a first test location and a second test location, then the cavitation threshold at a third test location can be extrapolated based on the cavitation thresholds of the first and second test locations. This extrapolation can be further based on the tissue type, target tissue depth, and acoustic pathway of the third test location.

Treatment Pulse Sequences and Thermal Management

A given Histotripsy therapy or treatment session can be defined in terms of a set number of pulses N that are to be delivered over a set total treatment time T. Thus, the total number of pulses N delivered over a total treatment time T (in seconds) is equal to the total treatment time T multiplied by the PRF of the system. For example, a system operating at a constant 200 Hz PRF for a total treatment time of 10 minutes (600 seconds) will have a total number of pulses N equal to 120,000. The systems and methods described herein can include PRF's of 400 Hz or greater to generate acoustic cavitation, including PRF's ranging from 400 to 900 Hz. As an example, if a PRF of 200 Hz is employed, therapy may be applied over 10 minutes.

Systems and methods are provided herein that implement Histotripsy pulse sequences with frequent short cooling periods that advantageously improve the thermal profile generated by histotripsy treatment, with the limiting case of N pulses equally distributed over the treatment time T yielding the minimum temperature rise. These pulse sequences can further be characterized in terms of the amount of time in which therapy is actively delivered to tissue relative to the amount of cooling time in which no therapy pulses are delivered to tissue. For example, a system delivering therapy pulses at a 400 Hz PRF for 5 minutes, followed by a 5 minute cooling time in which no therapy pulses are delivered (for a total treatment time of 10 minutes) would have a ratio of therapy (5 minutes) to cooling (5 minutes) of 1:1. PRF can be adjusted to any frequency between 200 and 900 Hz, and as frequency pf PRF is increased, greater and more frequent cessations of the application of energy can be employed. For example, at 400 Hz PRF, the therapy can be applied for 2.5 minutes followed by 2.5 minutes of cooling until a total of 10 minutes of therapy is achieved.

In general, when the therapy PRF is doubled and cooling steps are imposed the extent of the temperature rise is dependent on the distribution of cooling steps. A single long cooling step may result in the greatest temperature rise observed with this strategy. Conversely, shorter/more frequent cooling steps more closely approximate the case of equally distributed pulses and result in the lowest temperature rise observed with this strategy. Further, within a given total treatment time window, a higher therapy to cooling time ratio (e.g., 3:1) is generally advantageous to a lower therapy to cooling time ratio (e.g., 1:3). Essentially, for a set number of histotripsy pulses delivered within a given time window, a lower PRF is thermally beneficial.

Further details and examples relating to duration of therapy, PRF, therapy time, colling time, and other factors are described in detail in commonly assigned WO/2021258007 filed Jun. 18, 2021 entitled HISTOTRIPSY ACOUSTIC AND PATIENT COUPLING SYSTEMS AND METHODS, the entire contents of which is incorporated herein by reference.

When Histotripsy is used to ablate a target volume larger than the cavitation bubble clouds created by the system, the cavitation focus of the Histotripsy therapy system is moved (mechanically or electronically) within the target volume to ablate the entire target volume. In the context of this disclosure, mechanical movement can comprise movement of the physical position of the treatment head and/or therapy focus with the robotic positioning arm. Electronic movement of the focus, instead, is achieved with electronic-beam steering of the focus with the transducer array. In some embodiments, the focus can be electronically beam-steering without moving the physical position of the transducer array. In some embodiments, mechanical movement is combined with electronic beam-steering. This disclosure describes methods and workflows to and techniques to achieve a Histotripsy therapy.

The Histotripsy System

FIG. 1A depicts a robotically driven Histotripsy system 10 in accordance with the disclosure, specifically a robotically driven Histotripsy system configured for planning and automated treatment of patient tissues. The Histotripsy system 10 includes a cart 12 in which is housed a histotripsy signal generator and a control computing device (not shown). A robotic arm 14 extends from the can 12 and a treatment head 20 including a therapy transducer 18 and an imaging probe 22 (FIG. 2) is connected at distal end of the robotic arm 14. The robotic arm 14 includes an arm interface 16 (FIG. 2) enabling connection of the treatment head 20 to the robotic arm 14. A user interface display 24 mounted on the cart 12 is configured in connection with the control computing device (not shown) to present one or more user-interfaces (UI) and enable the workflows described herein in connection with FIGS. 3A-15 and 17-50 further below. An ultrasound imaging system 26 is connected to the treatment head 20 and particularly an imaging probe 22 (FIG. 2) for display of ultrasound images during all or portions of the procedure as described herein below. The user interface display 24 includes a variety of input points including physical controls such as knobs or buttons 28 for adjusting the planned treatment volume, contours, target, margin, and focus depth in X, Y, and Z directions as described herein below, an emergency stop button 30, a voltage knob 32 for adjusting, initiating and terminating application of voltage to the therapy transducer 18, a trackpad 34 for making selections and manipulating aspects of the user interfaces, and a space mouse 36 for driving the robotic arm 14 and the treatment head 20 using the robotic drive mechanism of the robotic arm controller. The UI display 24, may be a touch screen device capable of receiving user input into the various UI screens displayed in the UI display 24 and the workflows described therein. It should be noted that user input can include direct input or manipulation though a touch screen enabled UI or user input can include physical manipulation of the knobs 28 and space mouse 36 which interacts with the UI or combinations of those types of inputs. It should be understood that other forms of user input may also be acceptable and are within the scope of this disclosure including but not limited to mobile devices such as tablets, smart phones, smart watches, smart glasses/goggles, virtual reality (VR) enabled devices or systems.

Figure 1B:
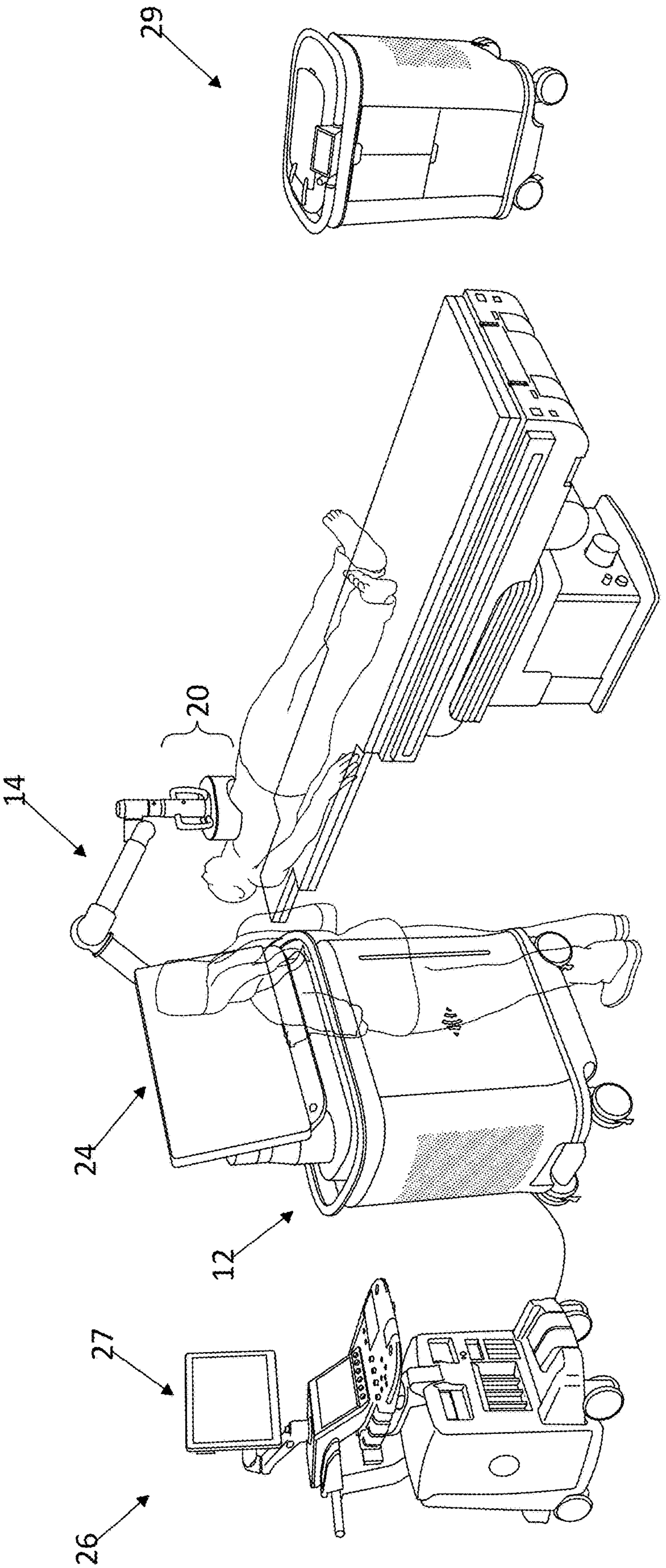

FIG. 1B is another view of the Histotripsy system 10 including cart 12, robotic arm 14, and treatment head 20. FIG. 1B also shows the ultrasound imaging system 26, which can be electrically coupled to the cart 12 to provide ultrasound images to the cart and associated controllers/processors. As shown, the cart 12 can include a user interface or display 24, and the ultrasound imaging system 24 can also include a user interface or display 27.

FIG. 1B also shows a fluidics cart 29 configured to fill a coupling system/container with an acoustic coupling medium for coupling the therapy transducer/treatment head to the patient. The coupling container is not shown in FIG. 1B for ease of illustration.

The Histotripsy system 10 is configured for use with separate imaging systems, such as ultrasound, MRI, cone-beam CT, etc., to provide real-time and/or perioperative imaging during histotripsy therapy. As illustrated in FIGS. 1A-1B, the Histotripsy system 10 may be configured for use with a separate ultrasound imaging system 26. This separate ultrasound imaging system 26 provides real-time visualization and may be used at any point during patient set-up, localization, planning, or post-procedure, as needed. The separate ultrasound imaging system 26 includes a freehand ultrasound and is also connected to the integrated ultrasound imaging probe configured within the treatment head 20. In particular, the histotripsy system 10 is positioned on a first side of the patient (e.g., right side of the patient or left side of the patient), and the separate ultrasound imaging system 26 is positioned on a second, opposite side of the patient (e.g., left side of the patient or right side of the patient) as shown in FIG. 1B. It may be preferable to have the histotripsy system 10 and the separate ultrasound imaging system 26 disposed on opposite sides of the patient for better surgical workflow.

Figure 2:
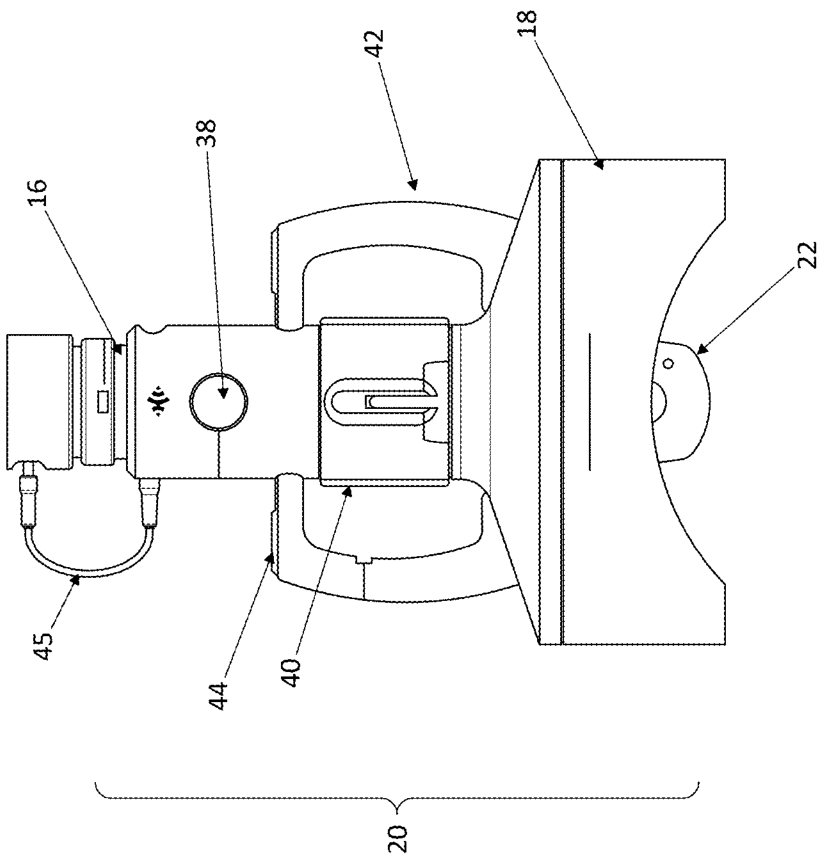
FIG. 2 depicts the treatment and imaging assembly of the histotripsy system in accordance with the disclosure.

FIG. 2 depicts an enhanced view of a treatment head 20 including the therapy transducer 18. The treatment head 20 is configured to interface/connect to robotic arm interface 16 at the distal end of the robotic arm 14 and to allow rapid exchange on and off to further enable a plurality of treatment heads (and therapy configurations) to be utilized on/with the Histotripsy system 10. For example, it is envisioned that a different shaped or sized treatment head 20 may be utilized when targeting treatment volumes and depths within the brain compared to, for example, abdominal locations such as liver or kidney. In particular, if a patient was being treated at various locations and depths within the body, a quick connect/disconnect may enable faster procedure times in the operating room. As noted above, the treatment head 20 includes the therapy transducer 18 and a separate ultrasound imaging probe 22. The imaging probe 22 is connected directly to the ultrasound imaging system 26 on the UI display 24 associated with the ultrasound imaging system 26. Additionally, the ultrasound imaging system 26 is connected to the control computing device within the cart 12 such that the outputs from the imaging probe 22 can also be viewed on the user interface display 24. The imaging probe 22 is configured to translate (extend) beyond the therapy transducer 18 by rotation of dial 38. In FIG. 2, the imaging probe 22 is depicted in its retracted position. An orientation and rotation tab 40 operatively connects to the imaging probe and enables 90 (degrees of) rotation of the imaging probe 22 relative to the therapy transducer 18. Handles 42 allow for grasping, and manual and/or robotically assisted movement of the treatment head 20. Freedrive buttons 44 are located on the top side of the handles 42. The freedrive buttons 44, when at least one is depressed by a user, substantially disconnects the resistance offered by the motors and gearing mechanisms of the robotic arm 14 but maintains sufficient resistance such that the robotic arm 14 does not collapse when the freedrive buttons 44 are depressed. In this manner the handles 42 and free drive buttons 44 enable load compensated positioning of the treatment head 20 and the robotic arm 14.

Figure 3A:
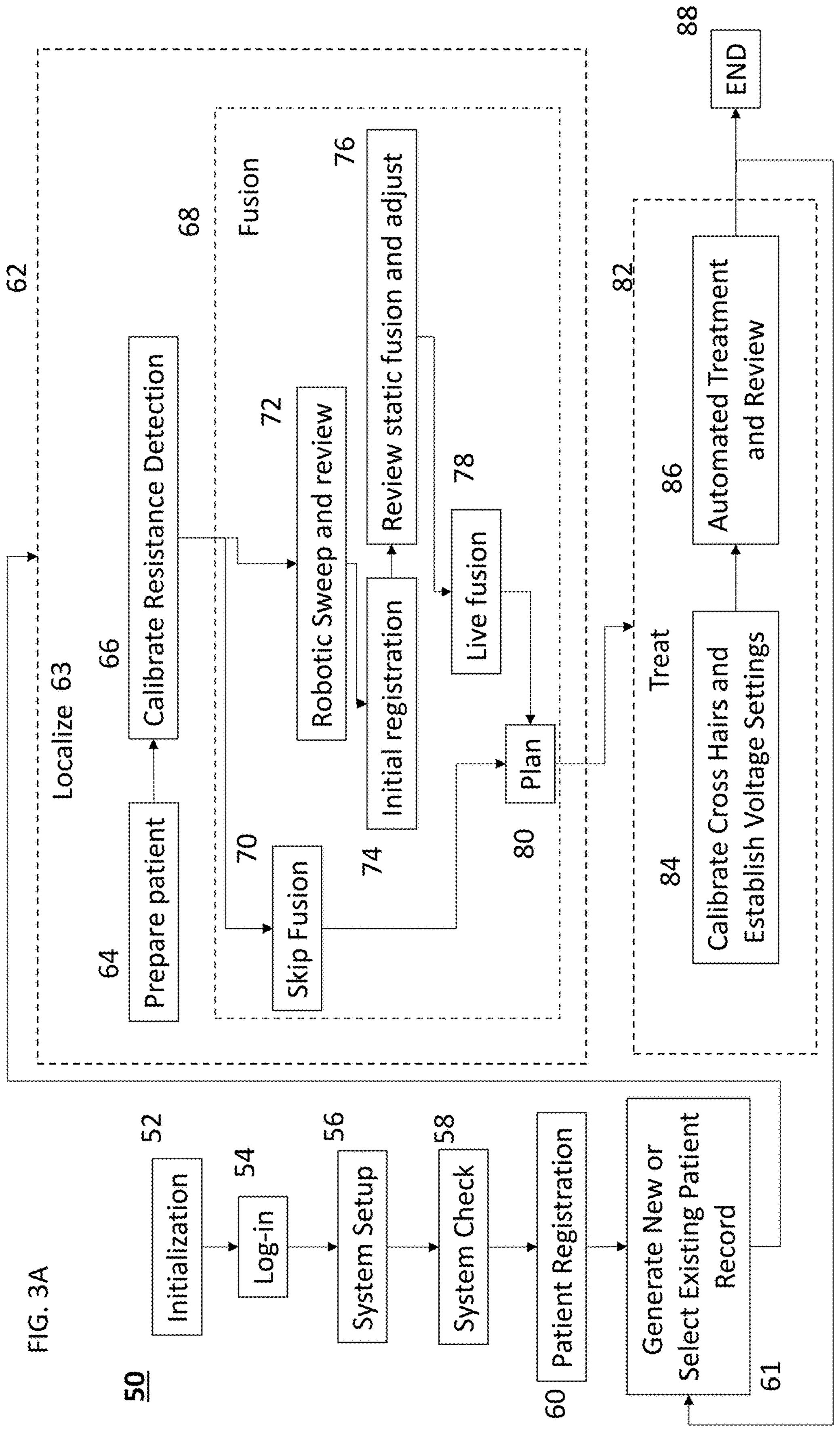
FIG. 3A is a flowchart outlining a method of treatment in accordance with the disclosure.

FIG. 3A depicts a broad overview of the steps employed in performing a Histotripsy treatment workflow 50. The workflow is primarily guide by a software application that runs on the control computing device. In an exemplary implementation, the workflow starts with initialization at step 52, where the software performs self-tests to ensure critical aspects of the Histotripsy system 10 are accessible and configured appropriately for the session. Once initialized, a user must log-in at step 54. At step 56 a systems set-up is undertaken as described in greater detail in connection with FIGS. 4-6, below. After a system set-up a system check is undertaken at step 58, detailed below with reference to FIGS. 7A-10C. Following the system check a patient registration is undertaken at step 60 and described in greater detail below in connection with FIGS. 11-12. Patient registration generates a new or opens an existing a patient record, as shown in FIG. 13, at step 61. A treatment session comprised of localization, planning and treatment, may be started from the opened or new patient record. Next comes a localization process at step 63, that employs patient preparation at step 64 and treatment head 20 buoyancy calculation or resistance detection at step 66 as detailed with reference to FIGS. 14-22. If following the resistance detection calibration at step 66 a skip fusion option 70 is selected (e.g., button 503 as shown on FIG. 24) the workflow progresses immediately to a treatment planning step 80. If fusion is desired then the workflow progresses to capturing a robotic ultrasound sweep of the patient and particularly the target area at step 72, described in detail with reference to FIGS. 24-27. Following the ultrasound sweep an initial registration is performed at step 74 (FIG. 28) by identifying landmarks in the ultrasound images and a pre- or peri-procedural image data set, which may have been selected during the patient registration step at 60, above, an initial registration is formed fusing the ultrasound images from the robotic sweep with those of the pre- or peri-procedural images. The initial registration is reviewed and adjusted at step 76 and described in connection with FIGS. 28-32 and once accepted, the live ultrasound images are fused with the pre- or peri-procedural images at step 78. Now at step 80, described in connection FIGS. 34-40, the live fused images or just the live ultrasound images are used to identify the anatomy to receive treatment, this includes treatment contour and a margin around the treatment contour as well as ensuring that the acoustic field 712 defined by field lines 724 may be used to avoid or take into account treating through bone, gaseous portions of the bowel, or other portions of the anatomy likely to absorb Histotripsy pulses and limit the efficacy of any portion of the treatment. The planning step also requires navigating to extreme regions of the volume to be treated to ensure that the robotic arm 14 and treatment head 20 can be navigated to the necessary locations on the patient's body without breaching a resistance to movement threshold. In addition, planning involves navigating to the highest location(distal-most to patient) in the treatment volume to ensure that sufficient coupling medium is present to complete the treatment. Further, as a part of planning, the user is also required to mark the location of the muscle/fat layer above the target anatomy, which is used as an input to the automated treatment algorithm. Once the plan is complete the workflow progresses to a treatment step 82. Treatment 82 includes a step 84 where the focal point 726 is calibrated to the bubble cloud location and then the voltage required to generated the bubble cloud at each of a number of survey points 739 are established to ensure that when the robotic arm 14 and therapy transducer 18 navigate to a location on the body that application of Histotripsy energy results in a bubble cloud 1108 at the focal point 726 as described in connection with respect to FIGS. 42-50. In addition, there is confirmation that the focal point 726 and bubble cloud are at a location proximate to the treatment contour 728 and the margin 732 for each of the survey points and a center point of a volume defined by those survey points 739. Once acceptable, automated treatment is undertaken at step 86 where a series of focal locations are individually treated with Histotripsy pulses described in connection with FIGS. 46-50. The volume to be treated is formed of a plurality of such focal locations, that may be arranged in an overlapping manner. The robotic arm 14 robotically moves the therapy transducer 18 along the exterior of the patient (ensuring no resistance threshold is breached) until all of the planned focal locations receive Histotripsy pulses. Once all focal locations have received Histotripsy pulses, the treatment can be reviewed using ultrasound imaging probe 22 either manually using the freedrive buttons 44 or electronically using the space mouse 36 to drive to robotic arm 14. Following review, the treatment session ends at step 88, or reverts to step 61 so that a new treatment session can be initiated. As noted above, this is a high-level description of the process and further details are provided below in context with their relevant figures.

Figure 3B:
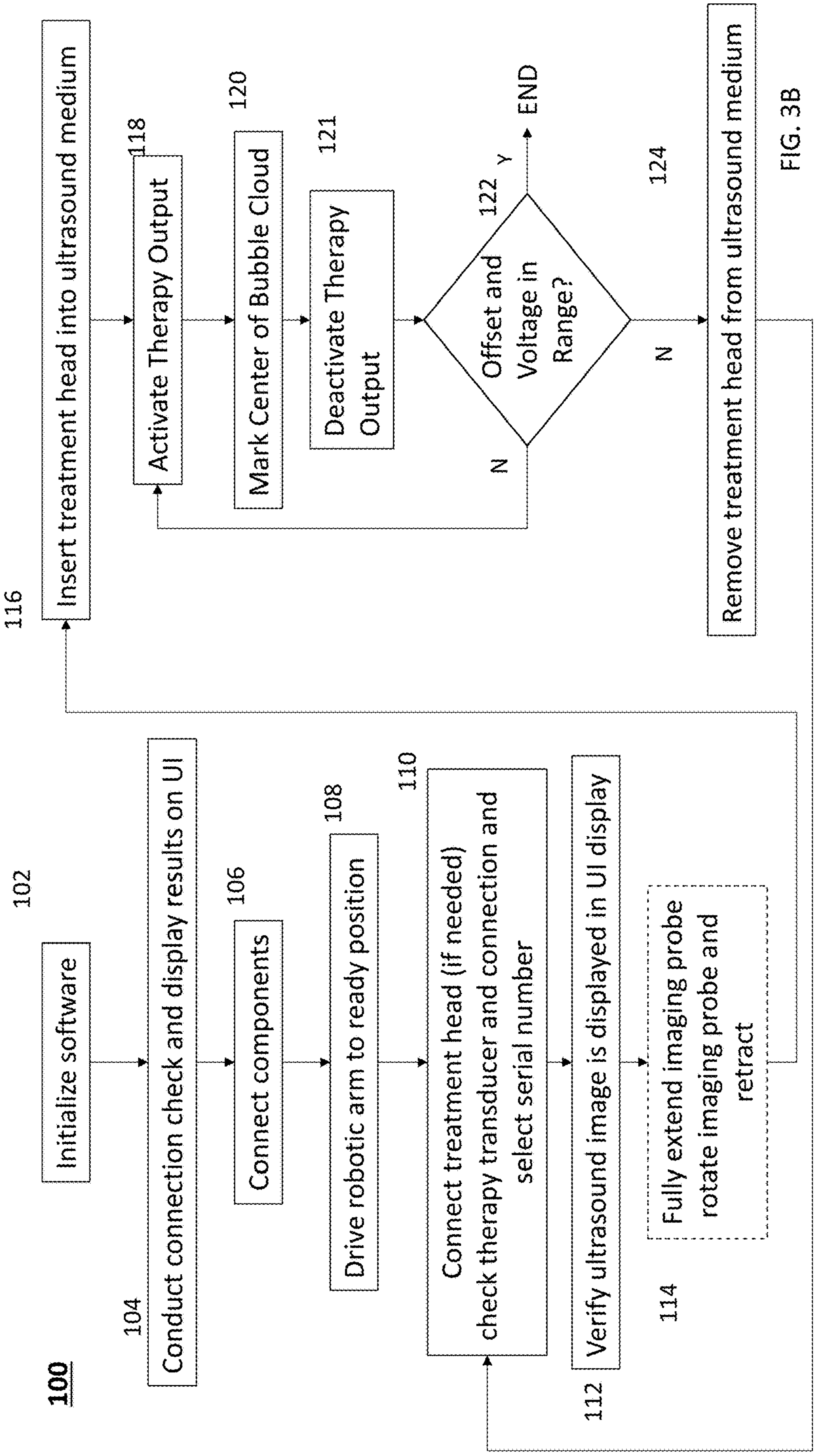
FIG. 3B is a flowchart outlining a method of initializing the histotripsy system of FIG. 1 in accordance with the disclosure.
Figure 4:
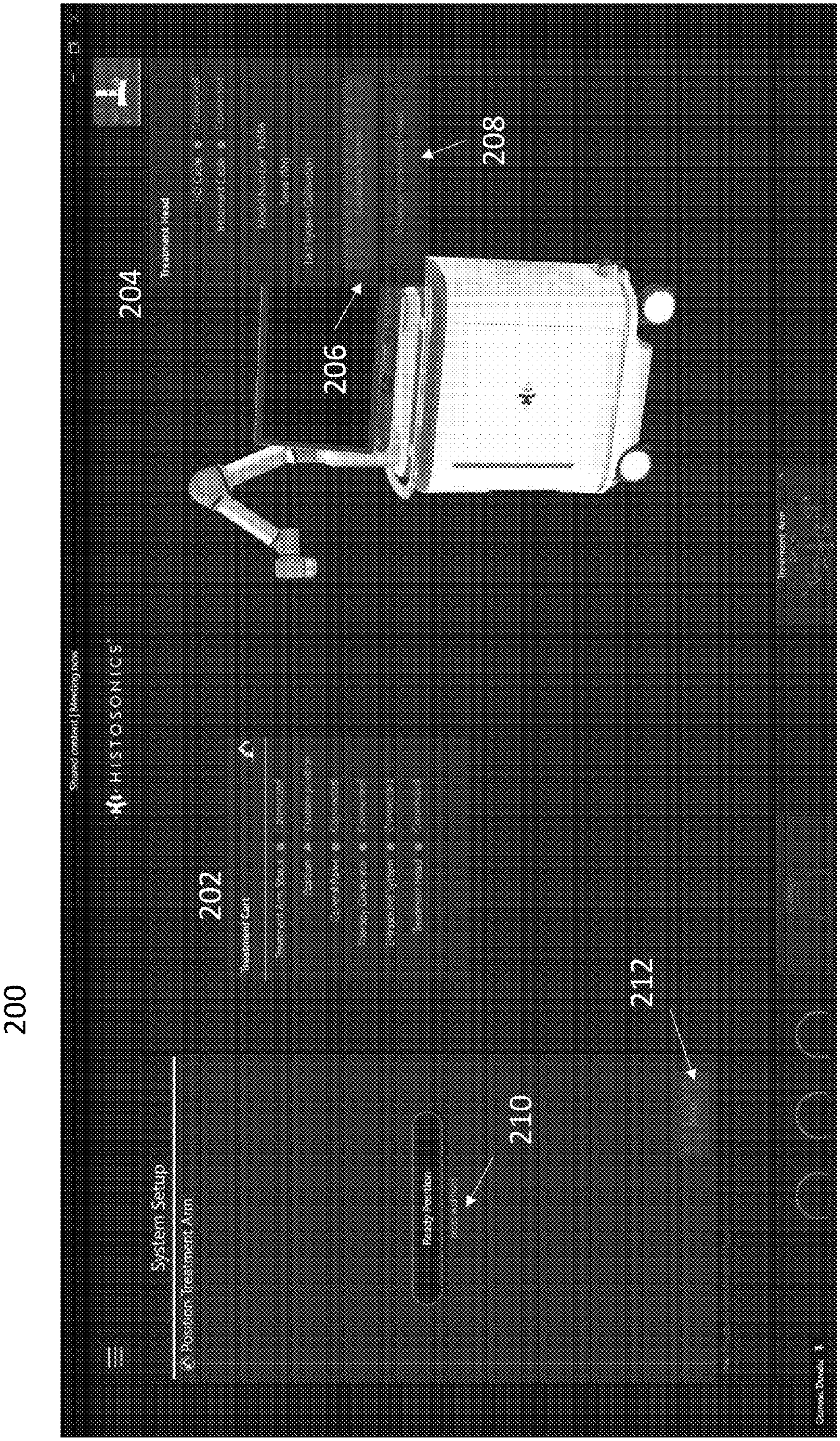
FIGS. 4-13 depict a series of user-interface images following the steps of the flowchart of FIG. 3B in accordance with the disclosure.

Having described the aspects of the workflow 50 at a high level each of these aspects will be described in greater detail starting with FIG. 3B. FIG. 3B is a flow chart outlining method 100 for initialization and set-up of the histotripsy system 10 in accordance with the disclosure. At step 102 following powering on of the histotripsy system 10, the software is initialized, which may optionally require input of log-in credentials to the computing device housed in the cart 12. Once initialized, the software conducts a connection check at step 104, the results of which are displayed on the user interface 200 in call out box 202 (FIG. 4). As can be seen in FIG. 4, the connection check looks to determine whether the robotic arm 14, the control panel (e.g., display 24 and input devices 28-36), a therapy generator (not shown but housed in the cart 12), the separate ultrasound system 26, and the treatment head 20 are connected to the computing device (not shown but housed in the cart 12). The connection check also seeks to determine if the robotic arm 14 is in the "ready position". If any of ultrasound system 26, control panel, therapy generator, or robotic arm 14 are not connected, the user connects these features as needed at step 106 and the connection check will update the status as appropriate. With respect to the treatment head 20, a record of the last calibration is displayed in call out box 204, where a button 206 allows for the initiation of a calibration, and a second button 208 enables a change of the treatment head 20.

Figure 5A:
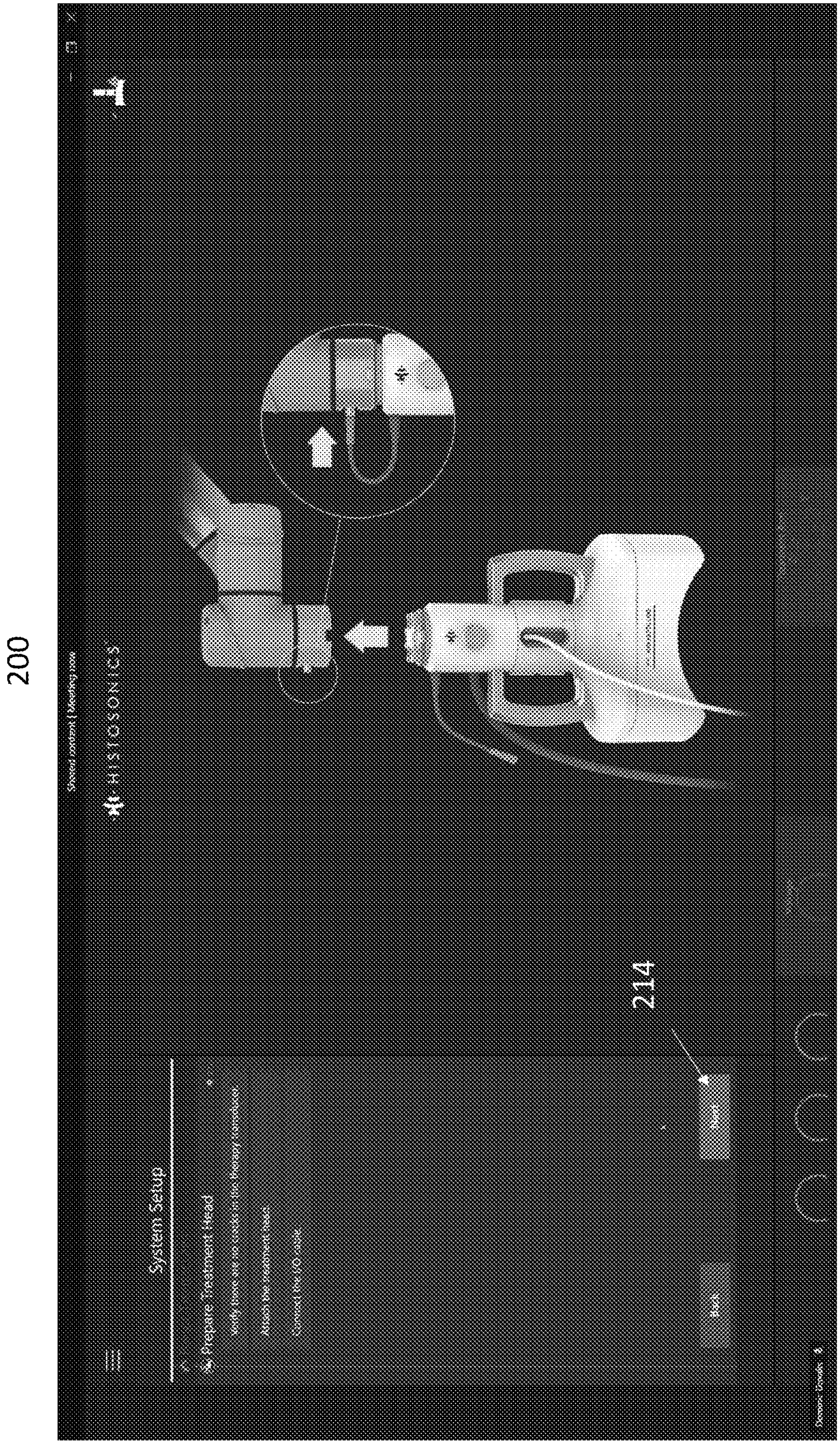

Regardless of whether the treatment head 20 is attached, the user is directed to press and hold the ready position button 210 (FIG. 4), which signals the robotic arm 14 to drive to the ready position at step 108. Once the robotic arm 14 is in the ready position a next button 212 becomes available and when selected, the user interface 200 changes to display a system set up screen on the UI 200, as seen in FIG. 5A. The system set-up screen provides instructions at step 110 for attaching the treatment head 20 (if needed), connecting an I/O cable 45 from the treatment head 20 to the robotic arm 14 that provides information regarding position and orientation of the imaging probe 22 (if needed), and checking the therapy transducer 18 for cracks or other defects.

The selected treatment head (and associated identification data) may include embedded configuration information (and files) to be relayed or as inputs into the histotripsy system via hardware/software interfaces. In particular, a memory board inside transducer ZIF connector communicates with a ZIF board inside the generator. Other cables and forms of wireless communication may be used to share information between the various system components information can be passed between the transducer and the generator. System information which may be passed between the treatment head/therapy transducer and the rest of the system (e.g., generator) may include therapy transducer specification details including but not limited to model number, serial number, number of transducer elements, focal depth/length, thermal offset coefficients, element timing calibrations; indications of use (anatomical location, organ, disease, etc.); work-flow details including software pages to recall, use case details (e.g., ultrasound guided versus CBCT guided, etc.), payload, different therapy sequences, bubble cloud location, imaging plane calibration matrix, bubble cloud expected size, expected voltage to attain bubble cloud in water performance and total run time; and/or service related data including system check calibration data (if it has been calibrated in 24 hours/past calibration data), date of mfg, and hours until service due. Connection of the treatment head may also include connection of a ZIF cable to the cart/generator and other I/O connectors to one or more robotic arm configurations, and/or imaging systems (ultrasound, X-ray, etc.).

Figure 5B:
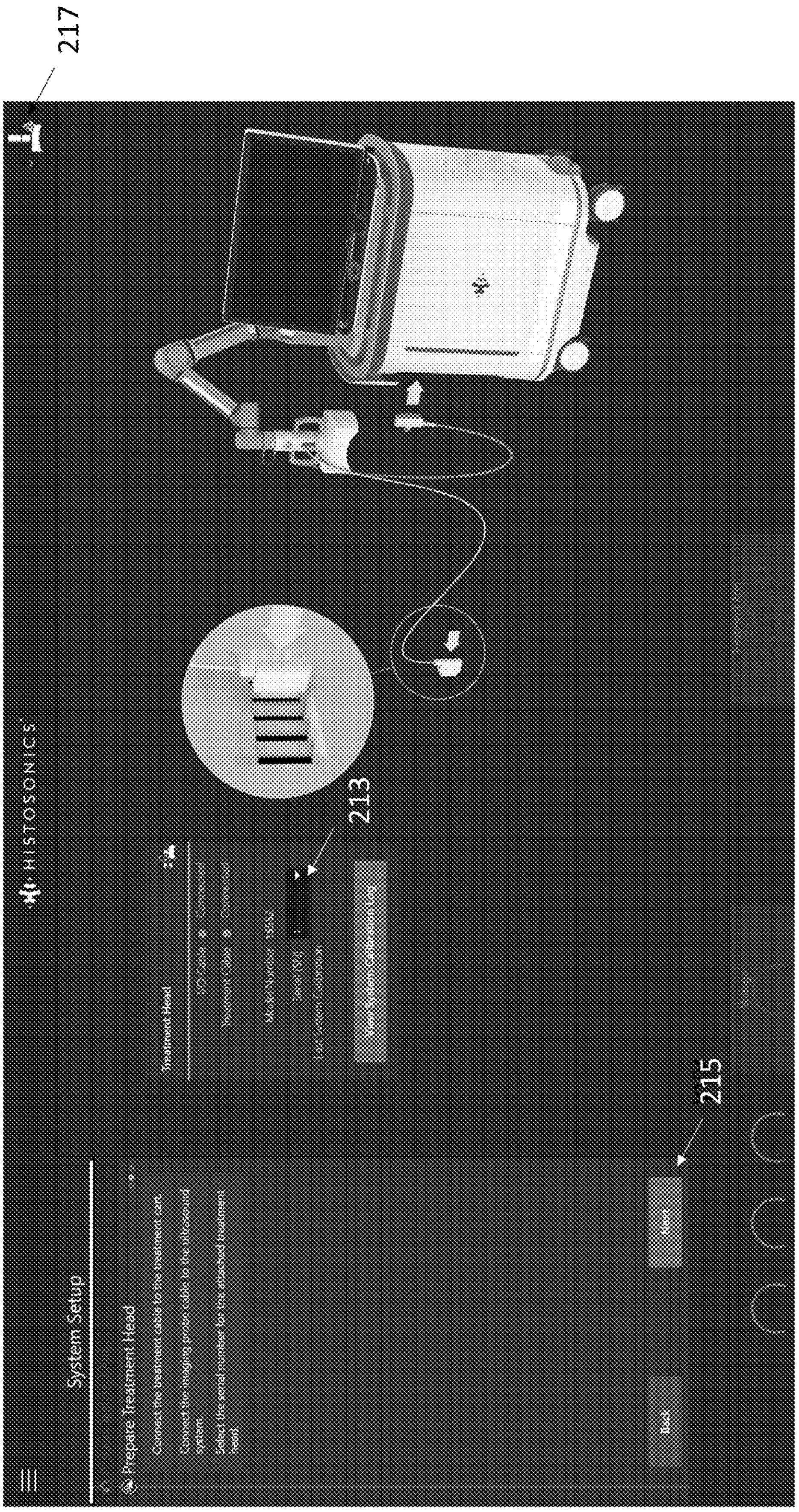
Figure 6:
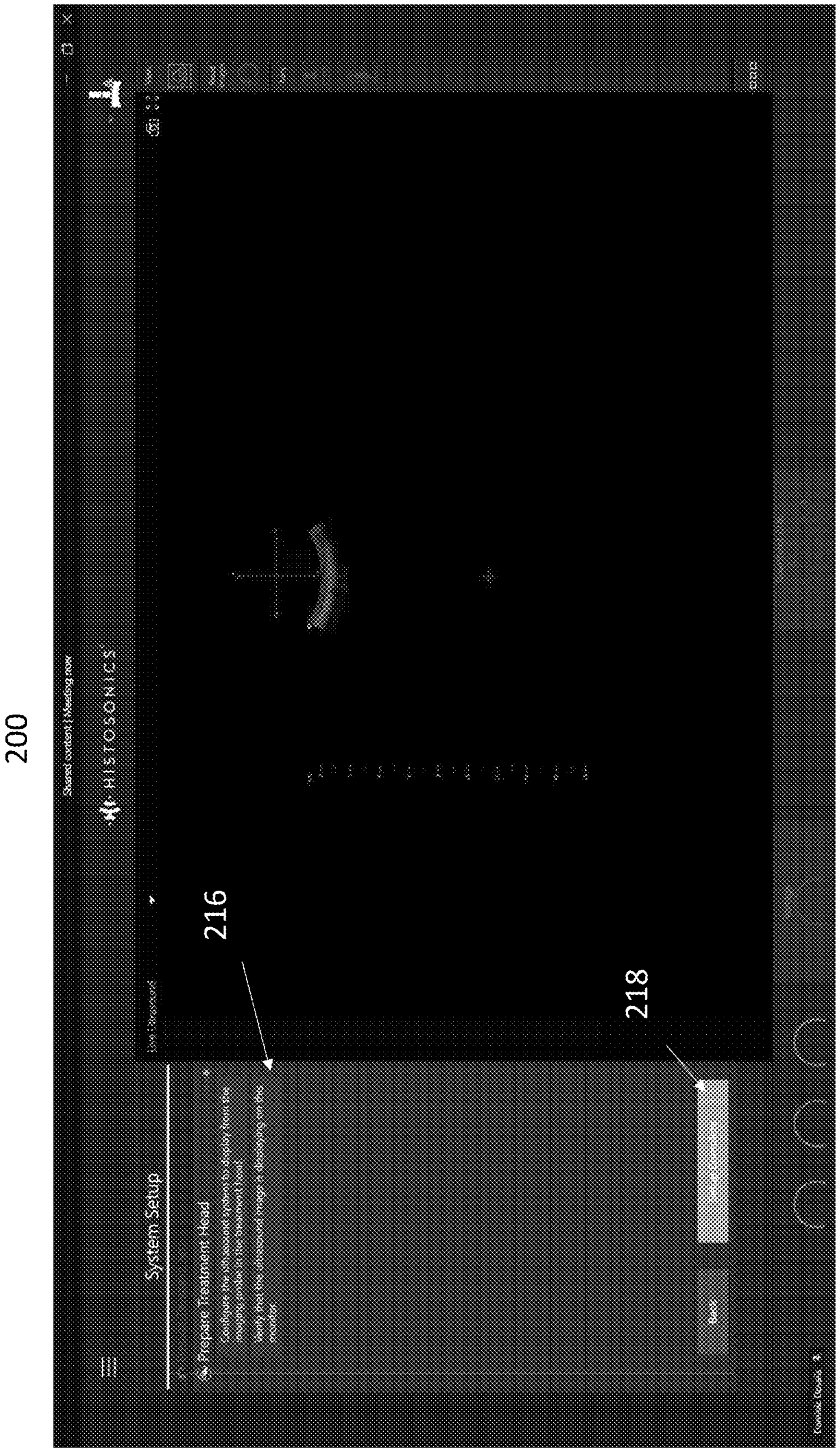

Once complete, and following selection of a next button 214, the UI 200 depicts the screen seen in FIG. 5B where the user is required to select the serial number of the connected treatment head from the drop-down list 213. Once a serial number is selected, the day and time of the last valid calibration, which is part of the system check, is displayed and the next button 215 becomes available. This information is also available in the treatment head menu 217 located in the upper right corner of the screen. Following selection of next button 215, the UI 200 shows the screen seen in FIG. 6, where confirmation is sought that the ultrasound imaging system 26 is outputting a signal to the computing device on the cart 12 so that the signal from the imaging probe 22 is displayed on the UI 200 at step 112. Text in panel 216 can be employed to instruct the user to confirm that the imaging setting of the ultrasound imaging system 26 is optimized for use in the Histotripsy system 10.

Figure 7A:
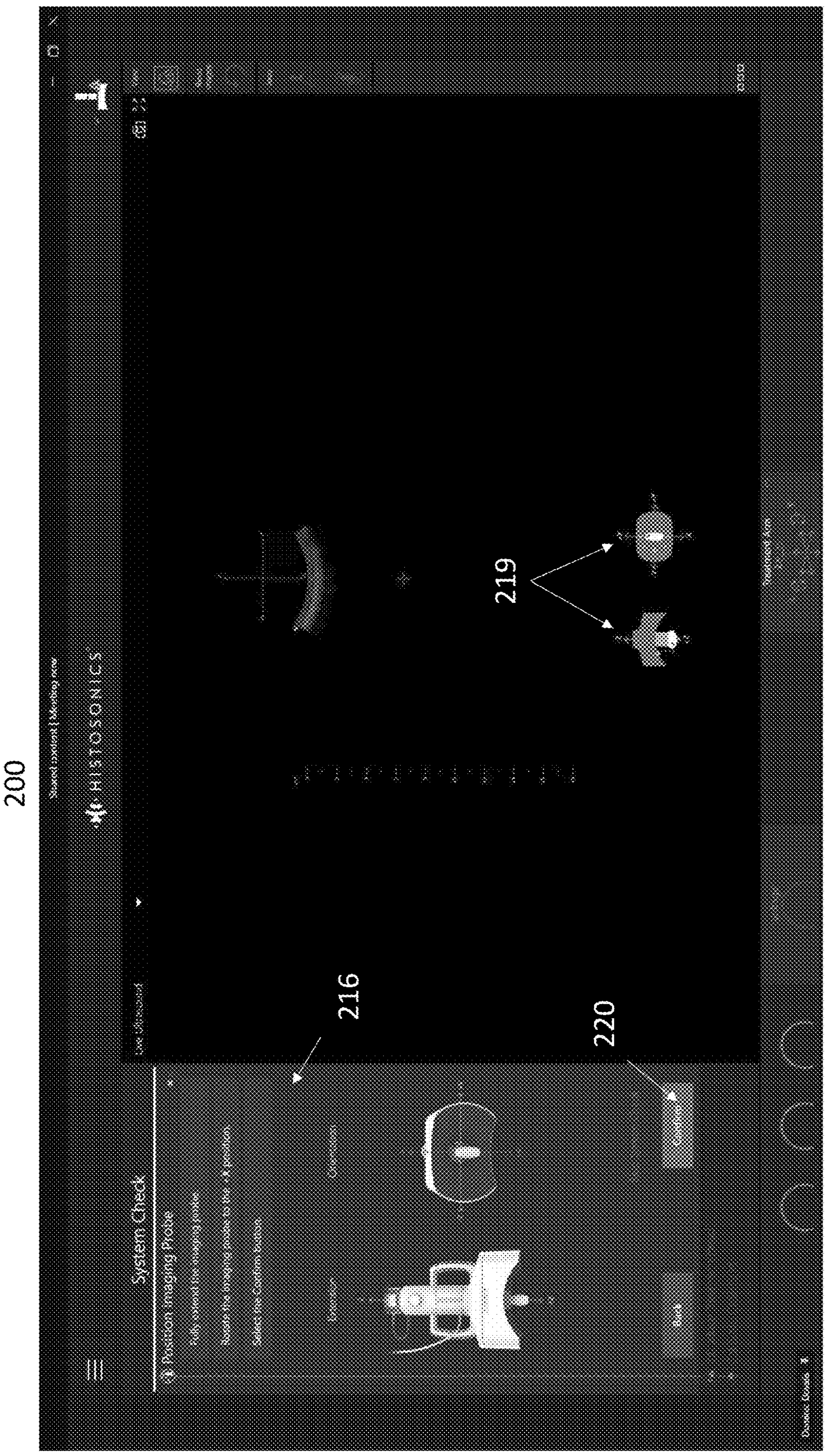

Following selection of the set-up complete button 218, the workflow moves into the system check phase (e.g., step 58 of FIG. 3) and the UI 200 displays the screen depicted in FIG. 7A. The Histotripsy system 10, and particularly the treatment head 20 requires calibration once per 24-hour period, however, often multiple procedures are planned within a given day, and the treatment head 20 may already have undergone calibration and be attached to the robotic arm 14, as indicated by the call out box 202. If a system check was performed within the last 24 hours, the result is still valid and there is an option to "skip system check" and move directly to patient registration phase (e.g., step 60 of FIG. 3). In some environments, system check may be performed at the beginning of each day, prior to any histotripsy therapy procedure. System check may also be employed when the location of the histotripsy system is physically moved to a new or different location, for example, moved from one surgical suite into a different surgical suite.

If a system check must be performed, step 114 is undertaken, where instructions are displayed in the UI 200 to fully extend the imaging probe 22 and to rotate the imaging probe 22 to the +X position. The actual position and orientation of the imaging probe 22 relative to the therapy transducer 18 is calculated continuously using signals sent via the I/O cable that can be interpreted by the software. Once the imaging probe 22 is moved to the required positions, as depicted by imaging probe orientation and position indicators 219, and the confirm button 220 is selected. When button 220 is selected, the software compares the actual signal for the position and orientation to a range of expected signals and the workflow will advance the UI 200 to the screen depicted in FIG. 7B if the actual signal is within the expected range. The workflow then requires the rotation of the imaging probe 22 back to the −Y position and retraction into the therapy transducer 18, which may be referred to herein as a "home position". Again, when a confirm button 221 is selected, the software compares the actual signal for the position and orientation to a range of expected signals and the workflow advances if the actual signal is within the expected range.

Figure 7B:
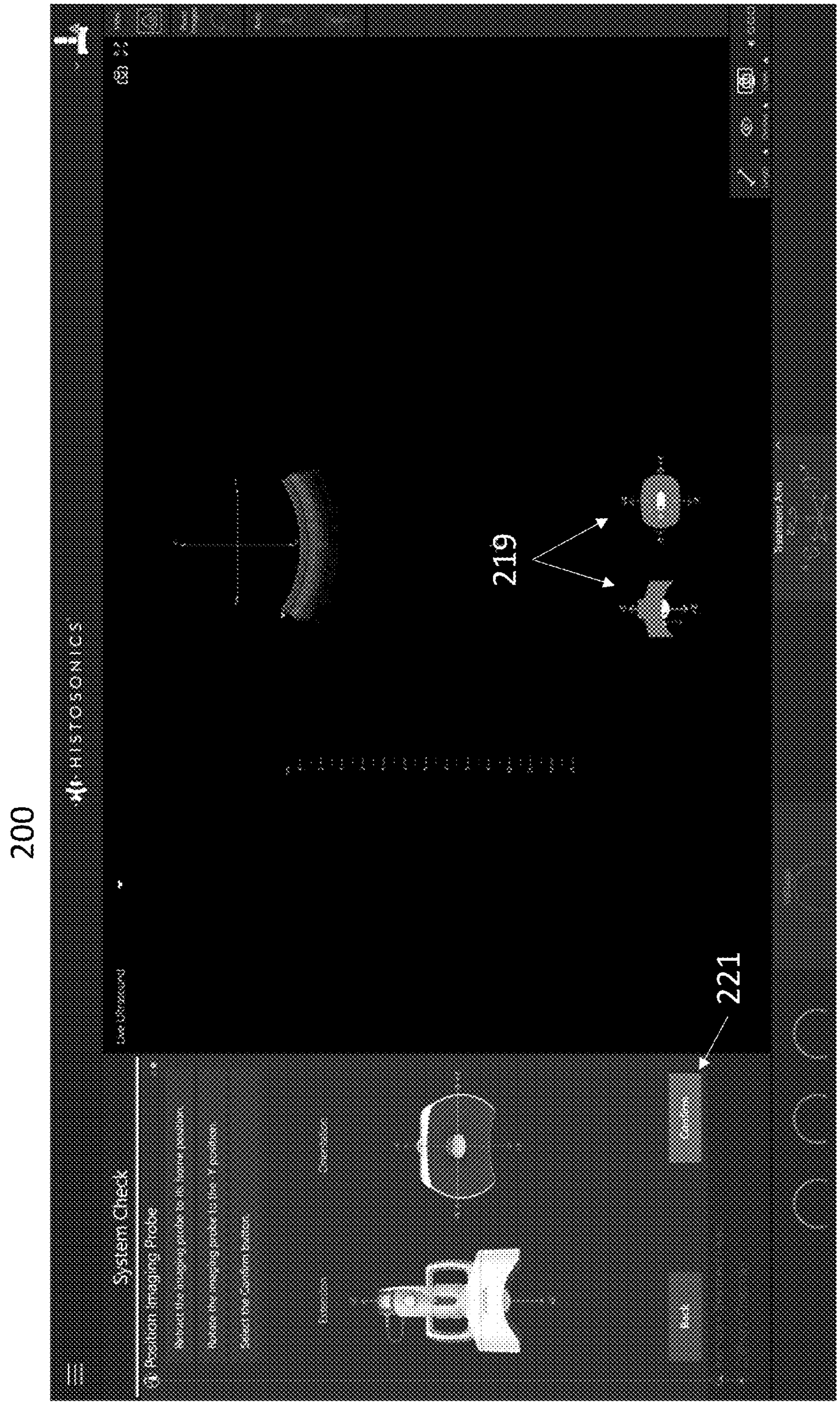
Figure 8:
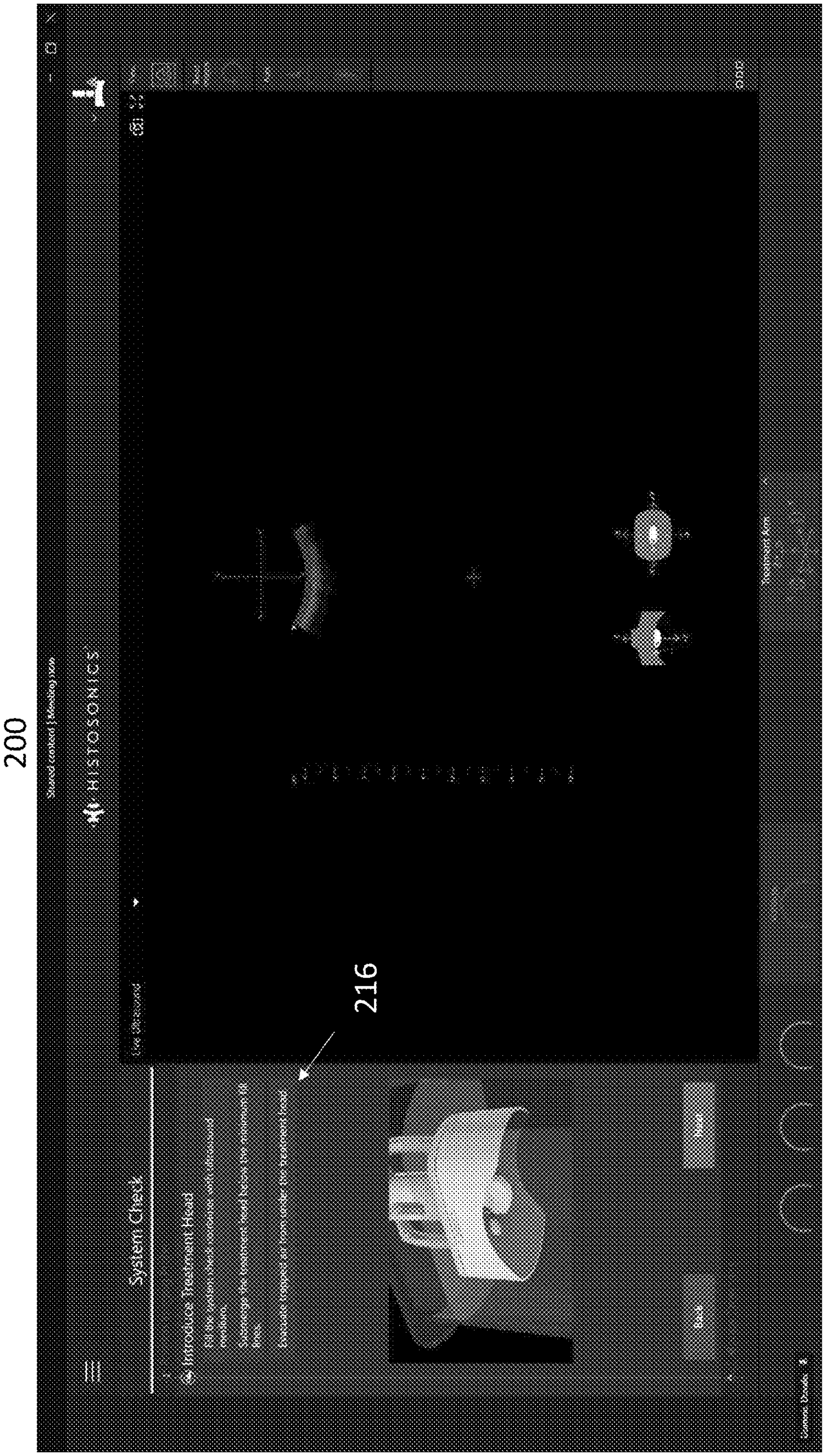
Figure 9:
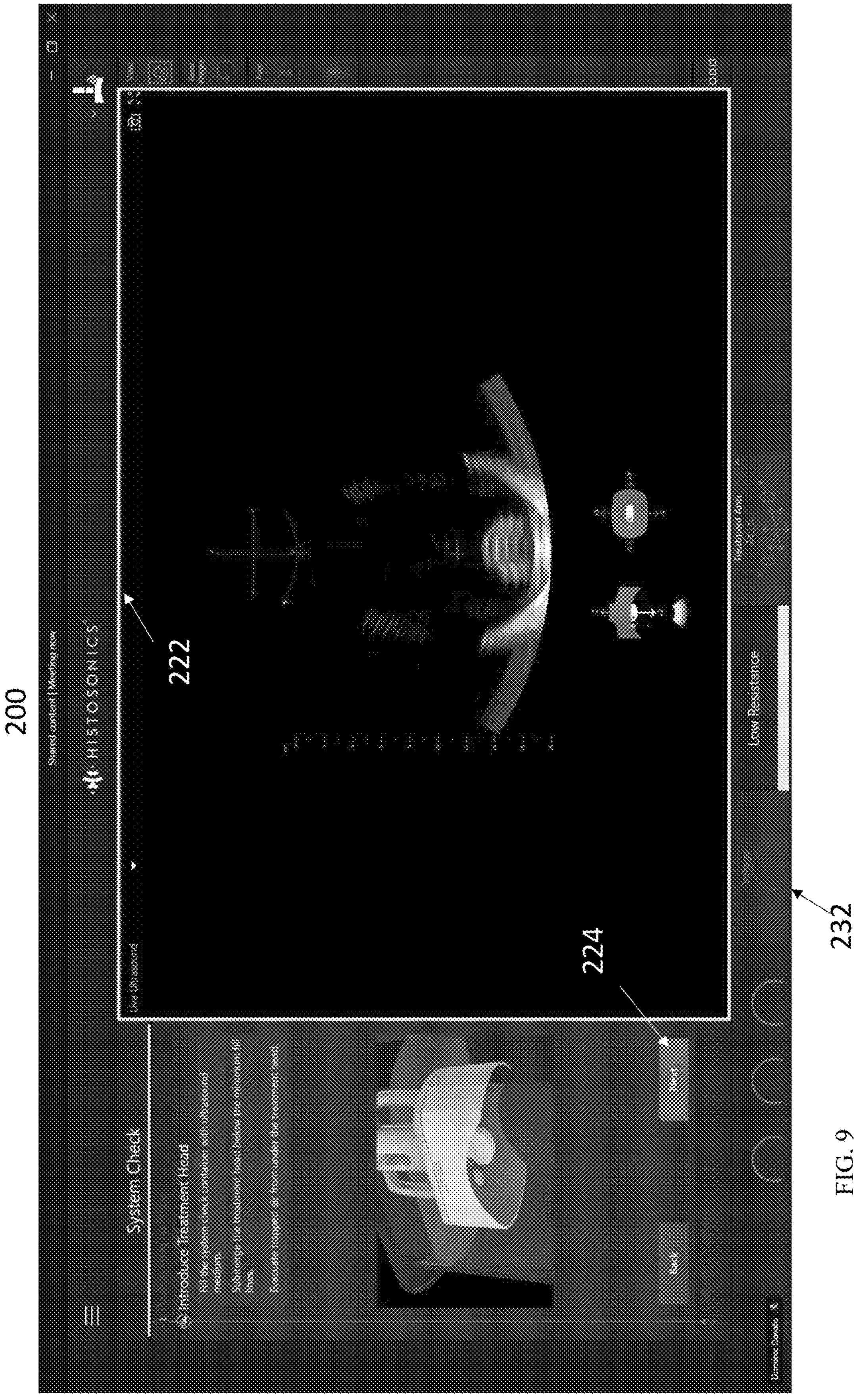

Following selection of the confirm button 221 in the UI 200 of FIG. 7B, the workflow progresses to the UI 200 depicted in FIG. 8, where instructions are provided in panel 216 to fill a fluidics container with ultrasound medium and to submerge the treatment head 20 into the fluidics container up to a minimum fill line at step 116. As the treatment head 20 is submerged in ultrasound medium, ultrasound images will appear on the UI 200 as shown in FIG. 9. The fluidics container may optionally circulate the ultrasound medium to remove/reduce gas and temperature adjust prior to submerging the treatment head.

As shown in FIG. 9 a resistance indicator 222 is depicted at the bottom of the UI 200 and as a border, this indicates the resistance to movement experienced by the treatment head 20 as it is forced into the ultrasound medium, however, at this point of the process, the resistance has not been calibrated to account for the buoyancy of the treatment head itself. Details of that calibration process, which occurs prior to treatment are detailed below. The resistance indicator 222 is a safety feature for the navigation of the treatment head 20, the accurate placement of treatment within the patient, and other aspects of the disclosure. Resistance indicator 222 may be illustrated in the UI as a color indicator, such a yellow, orange or red, corresponding to a pre-set value which may be read at "low", "medium" or "high" resistance. Other resistance indicators are within the scope of this disclosure and may be present to the user on the UI or elsewhere on the console or cart. Alternatively, resistance indicators may be audible, physical sensations, or other visual indicators to the user.

Figure 10A:
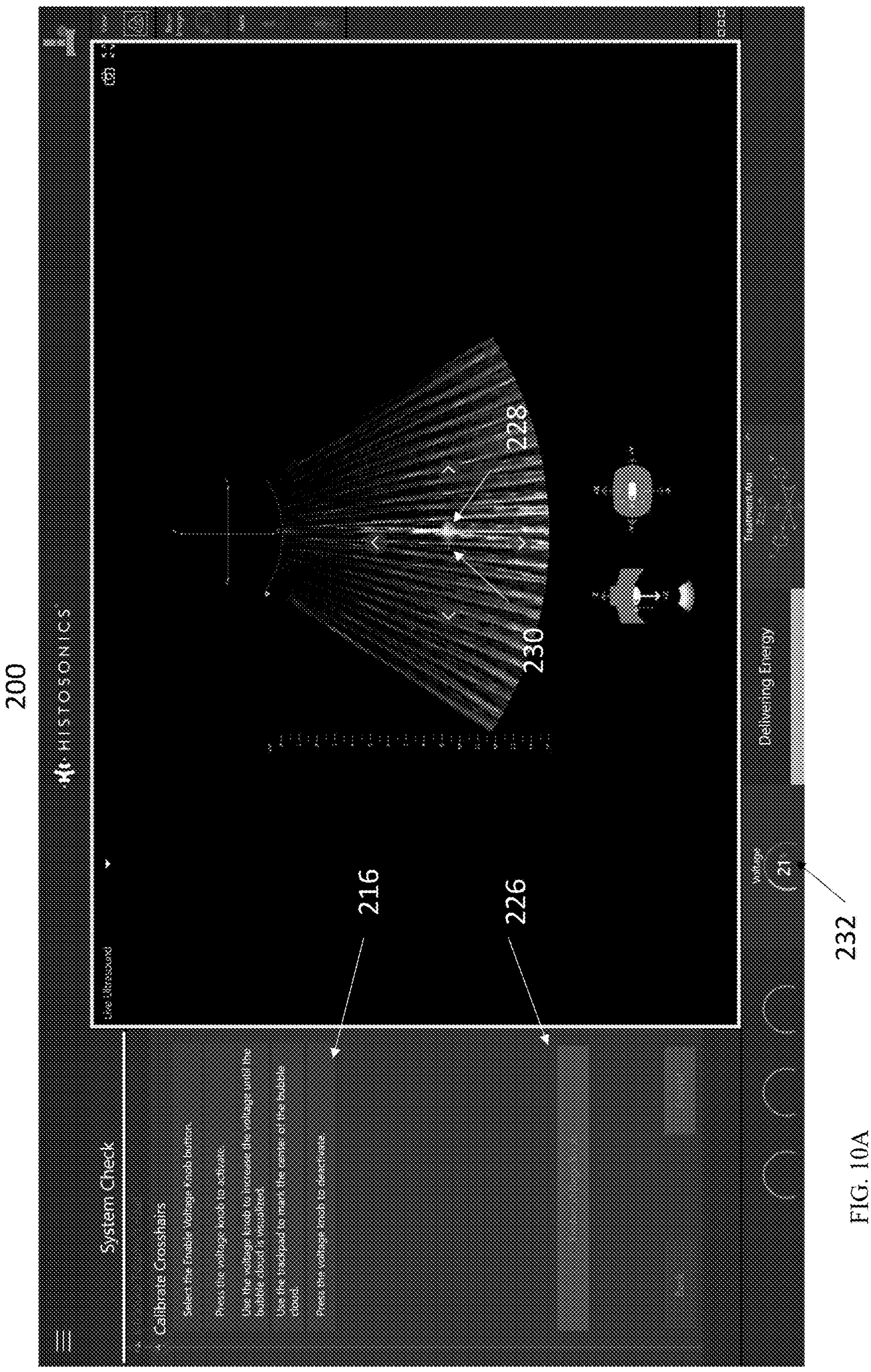
Figure 10B:
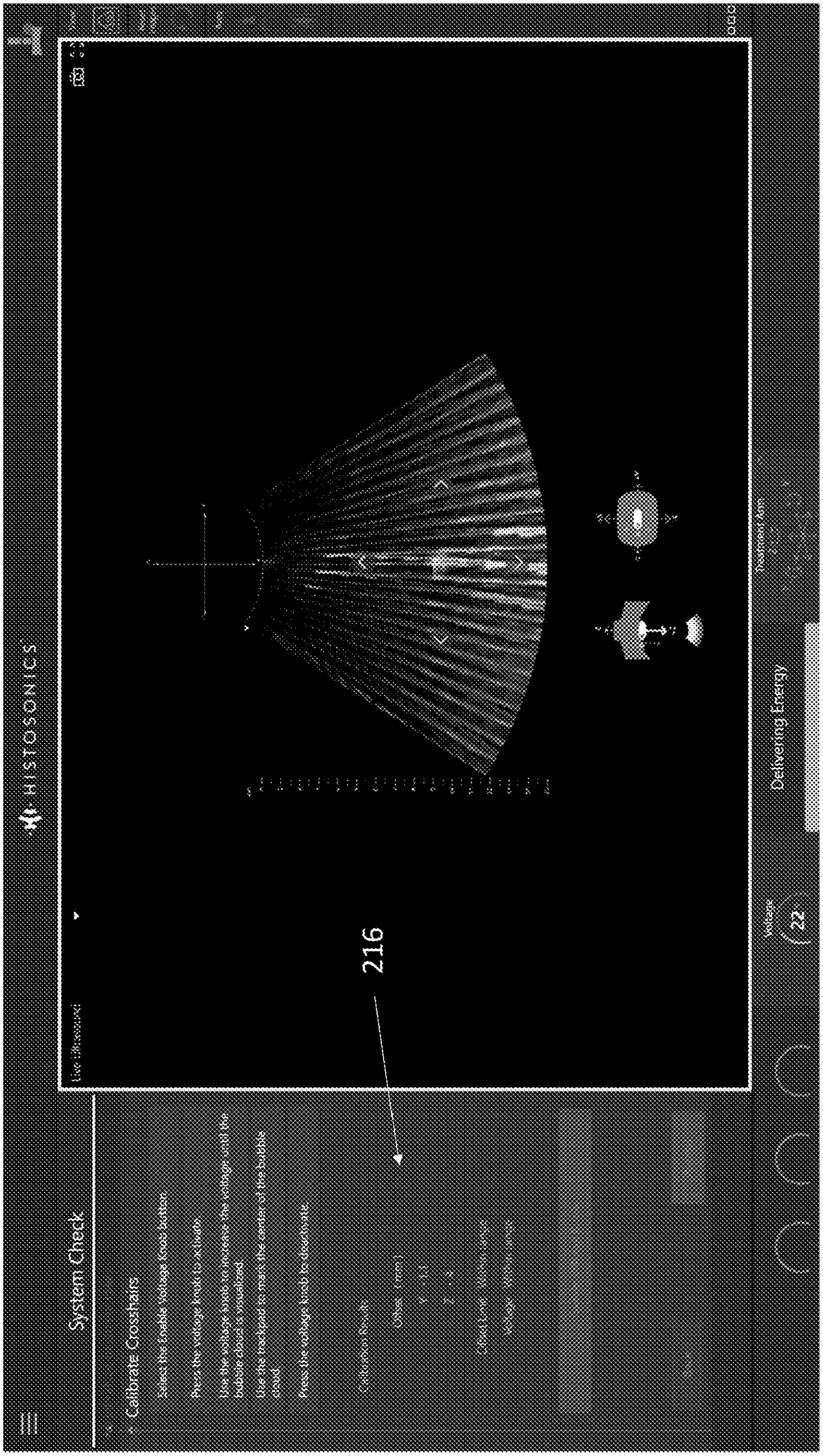
Figure 10C:
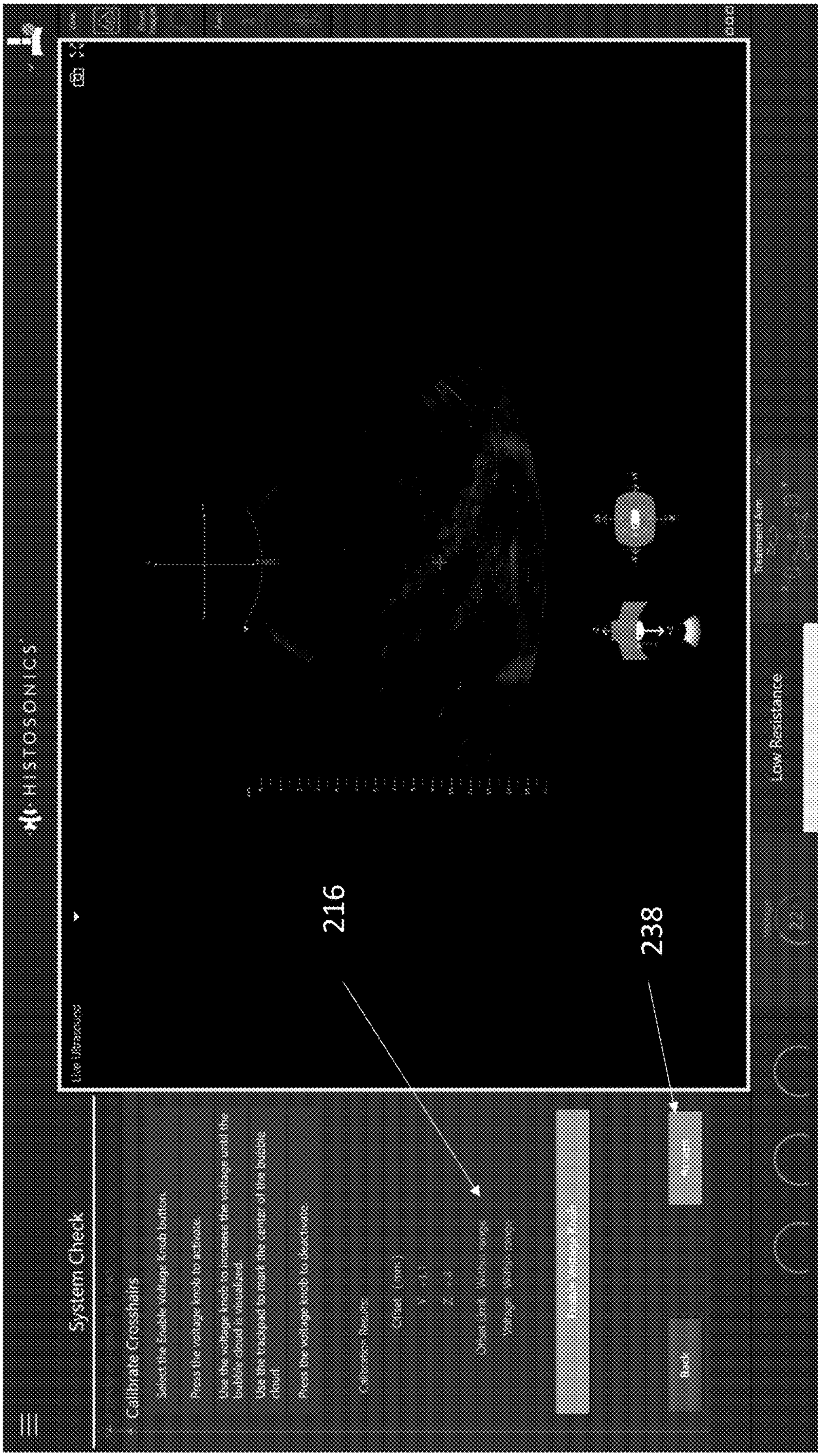

Following selection of a next button 224 in FIG. 9, the method 100 starts a calibration process for the therapy transducer 18. This calibration process is intended to align an indicator to a location of the therapy focus (e.g., the center of a bubble cloud) formed by the therapy transducer 18. As depicted in FIG. 10A, instructions are provided to activate therapy output at step 118 by selecting button 226, and then to depressing the voltage knob 32. Then therapy output is increased by turning the voltage knob 32 until a bubble cloud 228 is visualized. The bubble cloud 228 may be visualized when the voltage knob is approximately between 18-24% for degassed water (e.g., ultrasound coupling medium). The track pad 34 is used to mark the center of the bubble cloud 228 with indicator 230 at step 120. This visualization may be accompanied by the user detecting an audible signal in a given range (e.g., frequency or volume) which is indicative of formation of a bubble cloud. As can be seen by comparing FIGS. 9 and 10A-10C, the voltage indicator 232 is illuminated and been increased to read 210% and 22%. Once the bubble cloud 228 is marked with indicator 230, values of an offset distance, in particular, the distance the indicator 230 had to be moved to be centered in the bubble cloud 228, are presented in the UI 200 in panel 216 as shown in FIG. 10B. The voltage knob 32 may be depressed again to deactivate therapy output at step 121. If as shown FIG. 10C, all values are within an acceptable range and the therapy output is deactivated, the accept button 238 may be selected at step 122 the set-up and calibration workflows are complete, otherwise the method may continue to step 124 where the treatment head 20 is removed from the ultrasound medium and then back to step 110 where the therapy transducer 18 is inspected, and the method repeats. Alternatively, the method 100 may return to step 118 with the reactivation of the voltage knob 32 and a renewed attempt to mark the center of the bubble cloud 228 within the offset limits. As will be appreciated, if the calibration has been completed within the last 24 hours, one or more of the set-up and calibration steps may be eliminated without departing from the scope of the disclosure.

Patient Registration and Patient Record

Figure 11:
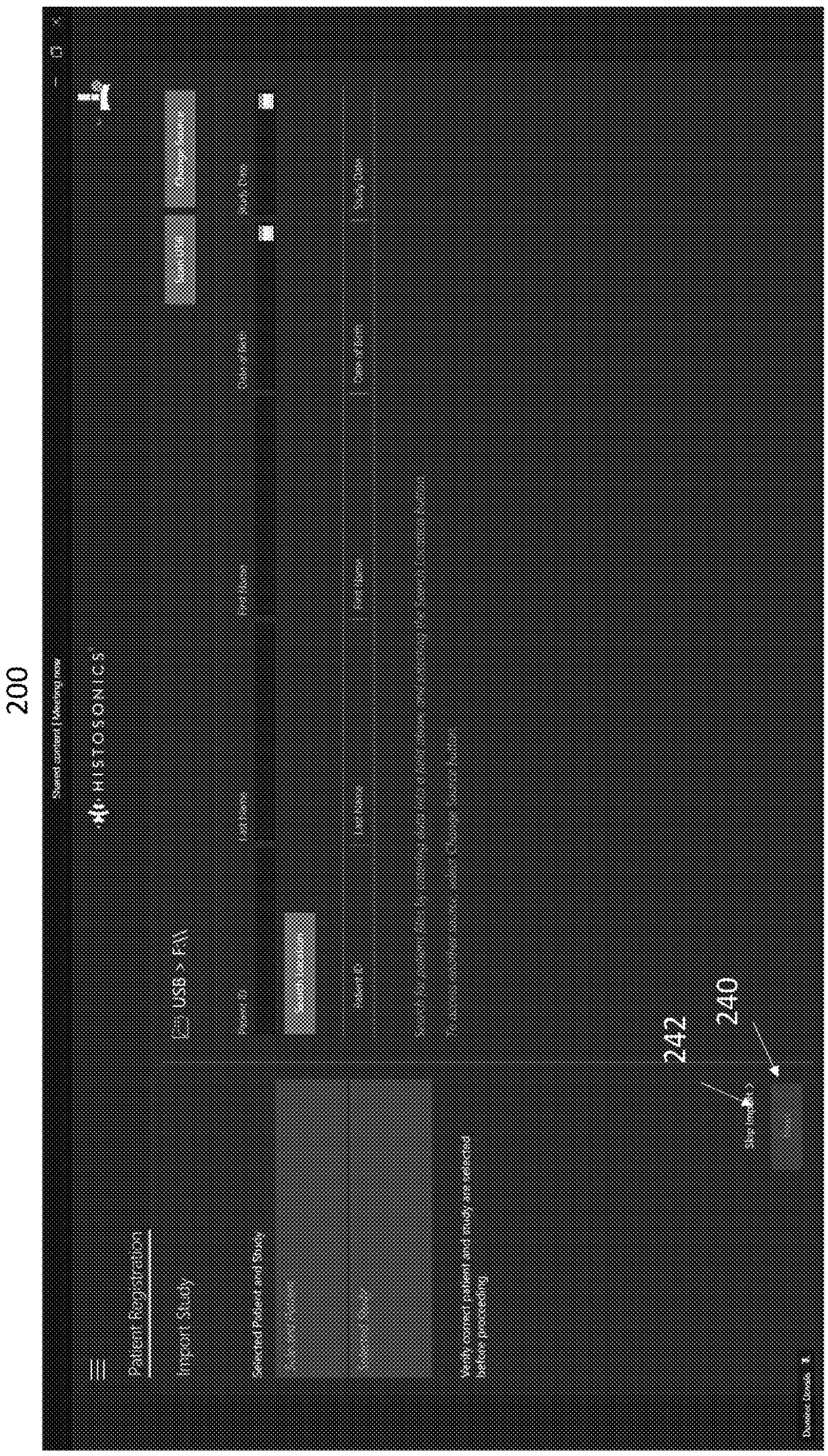
Figure 12:
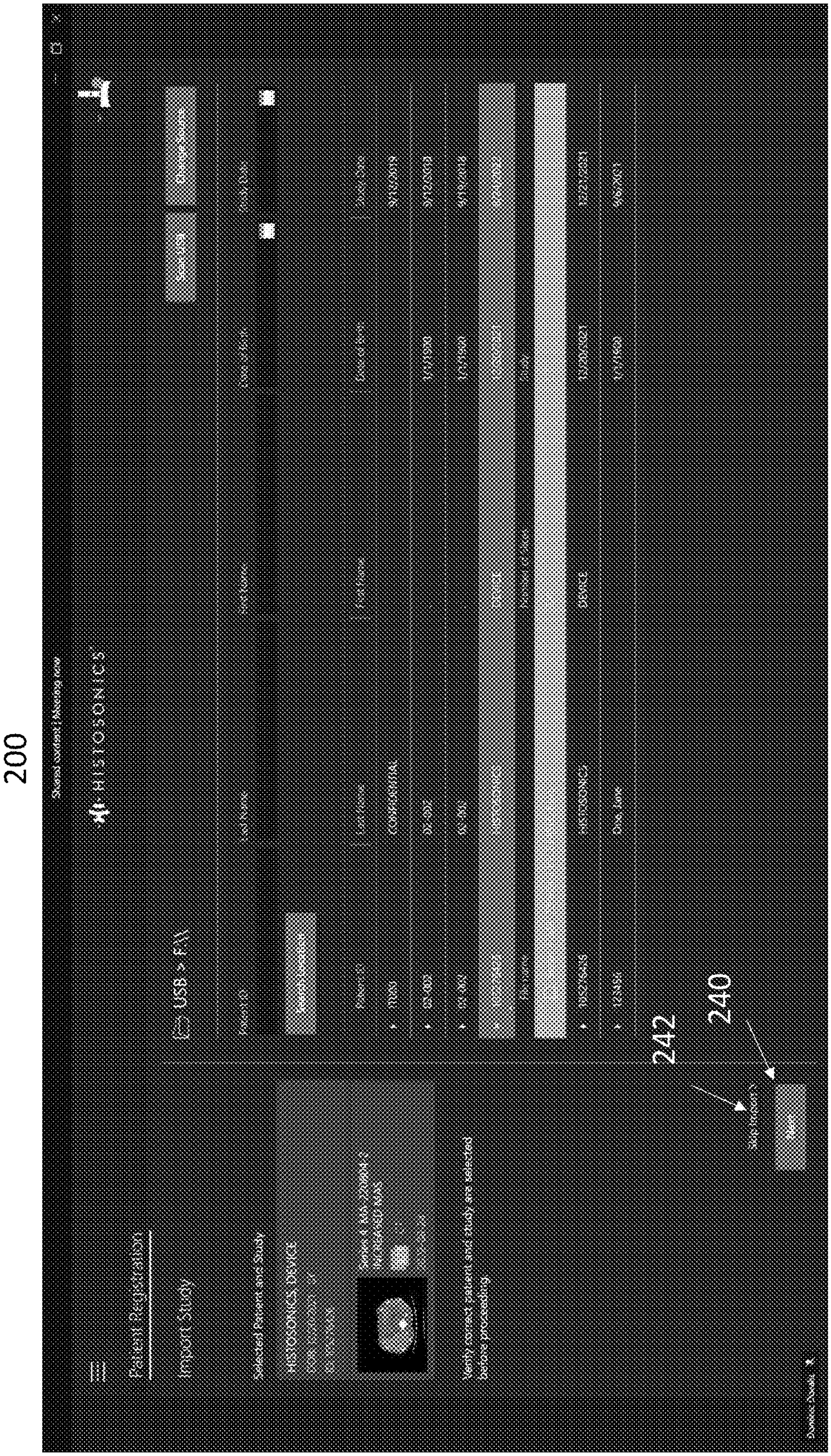
Figure 13:
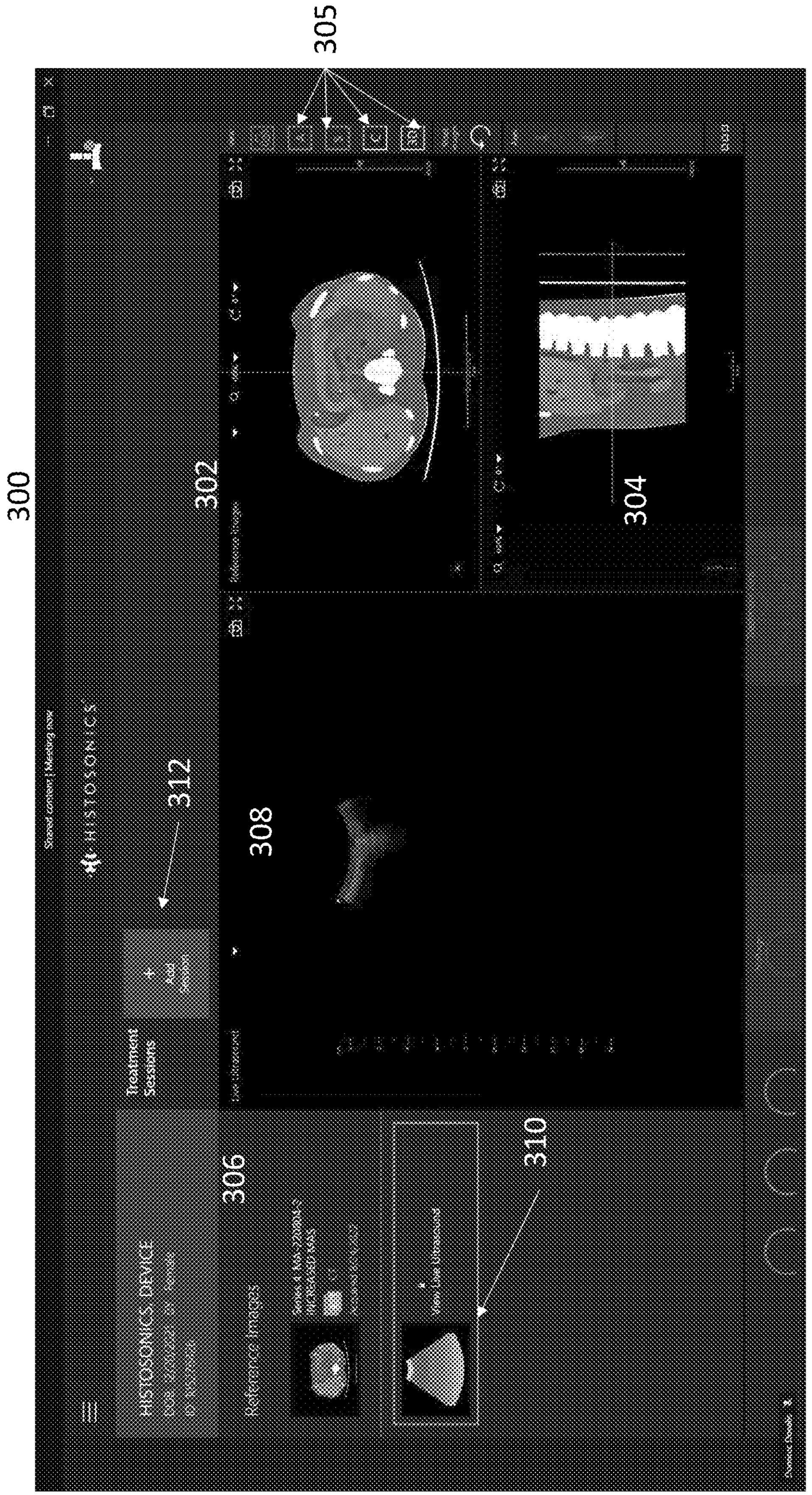

Following set-up and system check the UI 200 progresses to the screen depicted in FIGS. 11 and 12, allowing the user to select one or more image records for a patient. These image files, which may be ultrasound, magnetic resonance (MRI), computed tomographic (CT), cone beam CT (CBCT), and/or positron emission tomography-CT (PET-CT) images can be imported from an electronic medical record (EMR) database, PACS system, a USB drive, cloud-based information or storage system, or may be stored on a memory associated with the computing device in the cart 12. In some embodiments, for example for a procedure being conducted with a fixed room or mobile CBCT imaging system, the imaging system may serve as a DICOM node for the histotripsy system enabling transfer of images and data directly between both systems for use of pre, peri and post-procedure images. In some systems, these images/data may be utilized to enable multi-modal imaging localization and targeting, or conversely, peri-procedural identification of treatment locations or therapy tissue effect(s), and/or post-treatment verification of treatment effectiveness. By navigating the UI 200 and inserting a patient ID or name in FIG. 11, image files may be depicted, as shown in FIG. 12. These image files may then be utilized during the histotripsy procedure and displayed and/or used in a fusion process described herein such that they can assist in guiding the application of therapy to the patient by the therapy transducer 18, as outlined below. Even if no fusion is undertaken, the previously acquired images may be depicted in one or more sectors of the UIs described herein to assist in guiding the user to an appropriate location or the application of an appropriate therapy. As shown in FIG. 11, this importation process can be skipped entirely. In this case, the user is given the option to enter new patient details to create a new patient record or open an existing patient record. In some embodiments and system configurations, the image files displayed on the system may comprise various features including but not limited to, organ, tissue and/or disease segmentation, pre-planned treatment plan overlays, markings for simulated treatment head poses, and/or other computer vision enabled features to aid in the planning phases of a procedure.

Following selection of an image file and a next button 240 or selection of the skip import button 242 the UI 300 (FIG. 13) is displayed on the user interface display 24. If an image file has been selected, the reference images are displayed in a viewer as shown in FIG. 13 by fields 302 and 304, the reference images may be adjusted to display different imaging orientations or planes (e.g., axial, sagittal, coronal, and other projections) which are selected by buttons 305. The file name for the reference images selected and other information is displayed in a separate panel 306. The file name represents the patient record file under which any records of the therapy applied to the patient will be stored for later review and assessment. Further, live ultrasound images can be displayed in field 308 by selection of button 310. To start or add a treatment session, a button 312 can be selected.

Localize

Figure 14:
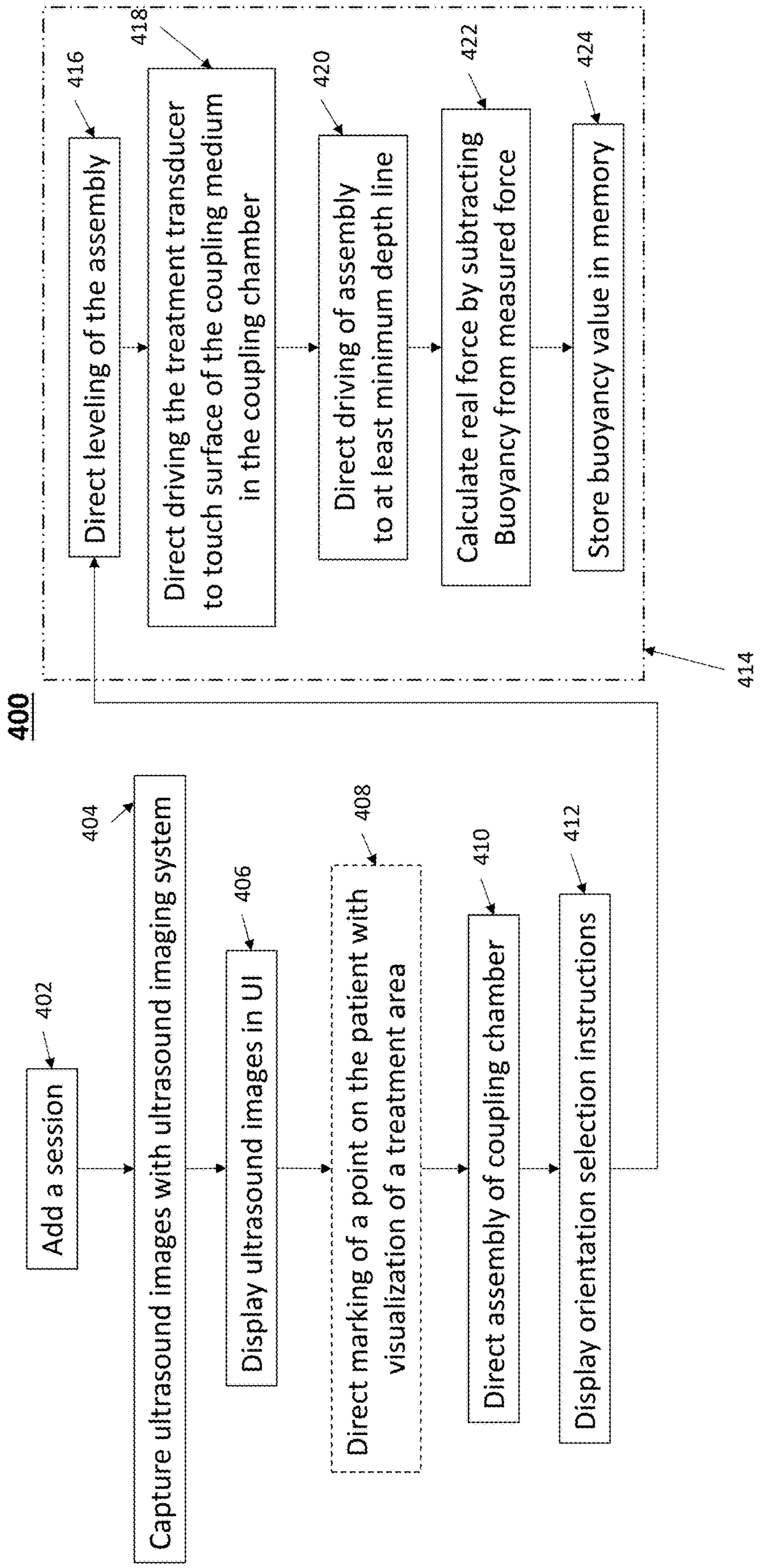
FIG. 14 depicts a flowchart outlining a method of setting up the histotripsy system of FIG. 1 and a coupling chamber in accordance with the disclosure.
Figure 15:
FIG. 15 is a user-interface detailing initial steps of the method depicted in FIG. 14 in accordance with the disclosure.

FIG. 14 shows a method 400 detailing the steps undertaken prepare the patient and the equipment of the Histotripsy system 10 for a treatment session and starts at step 402 by selection of the add a session button 312 in FIG. 13. Following selection of the add session button the UI 300 updates panel 306 to present instructions as shown in FIG. 15. Among these instructions is an instruction to utilize the ultrasound imaging system 26 (e.g., freehand) and its ultrasound imaging probe to capture ultrasound images which are displayed in field 308 at step 406. The images captured by an ultrasound imaging probe (freehand) are separate from the ultrasound imaging probe 22 incorporated into the treatment head 20 are displayed in both a display associated with the ultrasound imaging system 26 and in the UI display 24, in field 308. Imaging at step 404 and 406 ensures that treatment site, which may have been identified in pre-procedural images, is still of interest and has not changed or altered between the time of an initial diagnostic scan of the patient and the date of the procedure. The instructions further direct the user at step 408 to optionally mark a location on the patient (with a marker, sticker, or other identifying mark) at which an ultrasound probe of the ultrasound imaging system 26 is placed, or location at which the lesion or tumor of interest is interior to the patient body wall cavity so that the treatment area (e.g., lesion or tumor) can be visualized in the ultrasound images. To assist in locating and imaging of the lesion so the patient can be marked the user can reference the images displayed in fields 302 and 304. This marking additionally represents a point at which the treatment head 20 and/or coupling assembly 46 will be initially placed such that the imaging probe 22 can be used to visualize the treatment area. Thus, the positioned marked should check that an optimal path for the application of histotripsy therapy has been initially identified. It may be advantageous to reduce the application of ultrasound energy through hard tissues, areas of bowel gas, or other features that can affect the application of ultrasound energy to the treatment area. Once visualization is complete, selection of the next button 314, advances the workflow and depicts the UI 300 as shown in FIG. 17.

Figure 16:
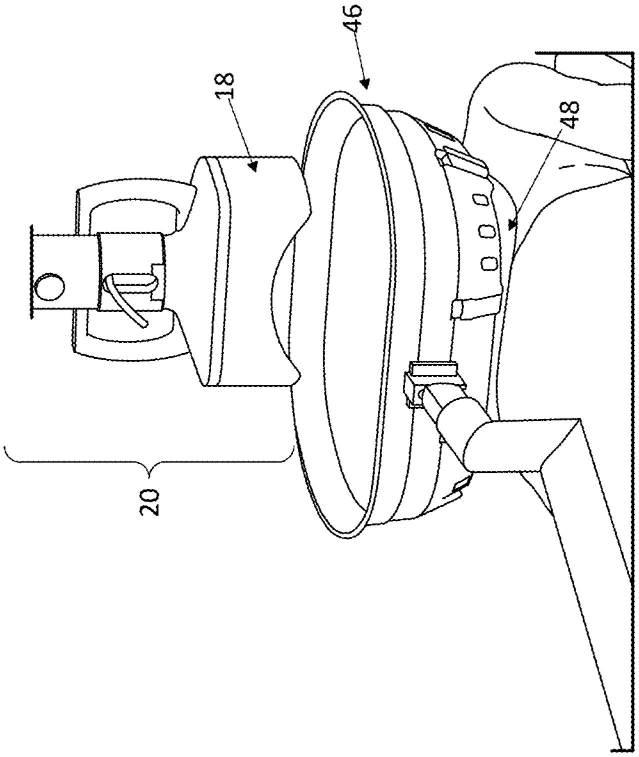
FIG. 16 depicts a coupling chamber and treatment and imaging assembly in accordance with the disclosure.

FIG. 16 depicts a treatment head 20 as it will be deployed for planning a therapy and applying therapy to a patient. The treatment head 20 is inserted into a coupling medium that is contained in a coupling assembly 46, the coupling medium enables acoustic coupling of the therapy transducer 18 to the patient. The coupling assembly 46 includes a conformal and flexible barrier film or membrane 48 that allows the coupling medium contained in the coupling assembly 46 while conforming to the shape and anatomy of the patient, and ensuring a suitable ultrasound coupling between the therapy transducer 18 (and the imaging probe 22), to the patient. A bed rail clamp (not shown) is secured to a side of a treatment bed and also supports the coupling assembly 46. As will be appreciated, when filled with between 12 and 25 liters of coupling medium, the coupling assembly will become quite heavy and require support to minimize the impact on the patient while still enabling sufficient coupling.

Figure 17:
FIGS. 17-22 depict a series of user-interface images following the steps of the flowchart of FIG. 14 in accordance with the disclosure.
Figure 18:
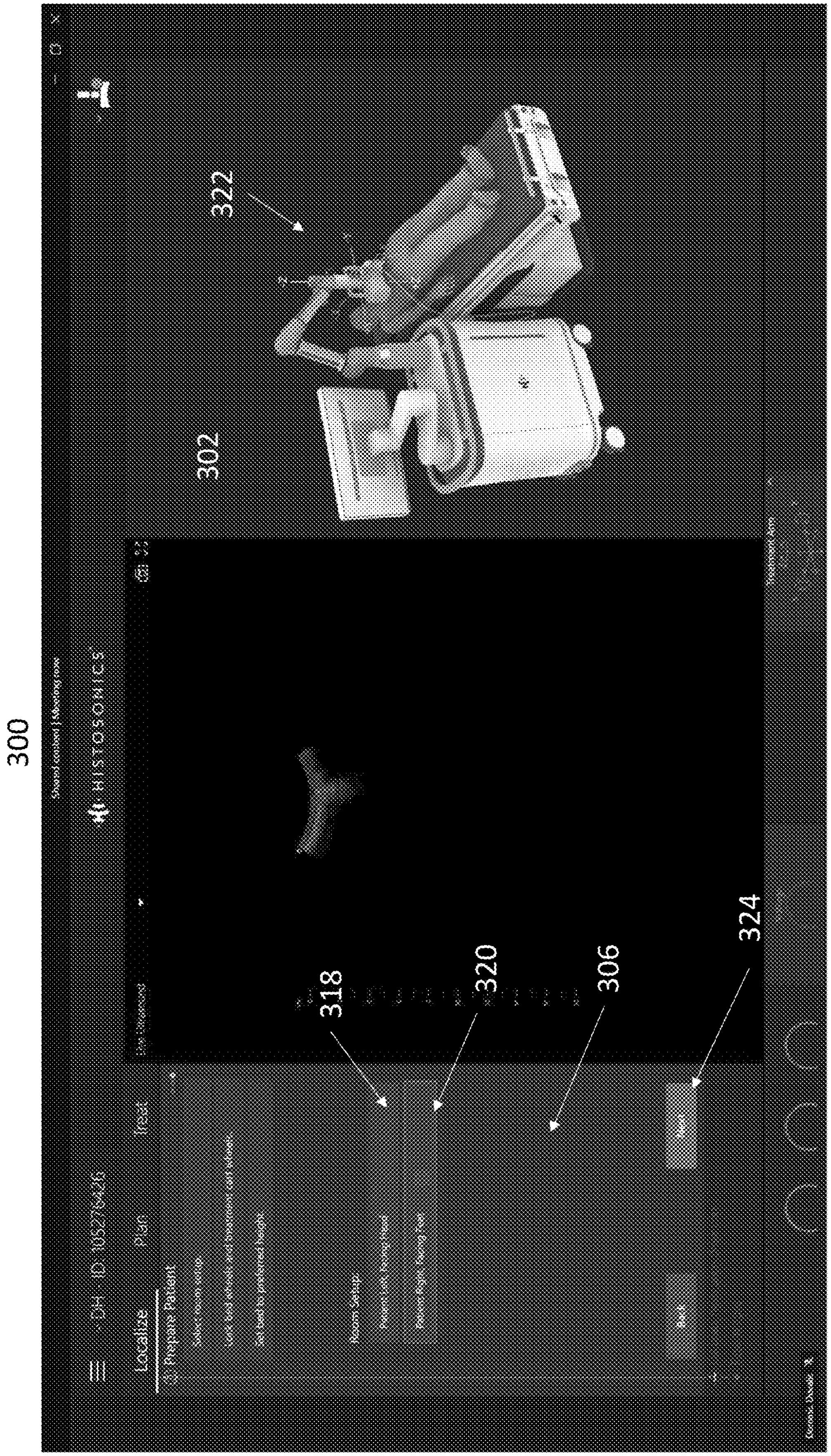
Figure 19:
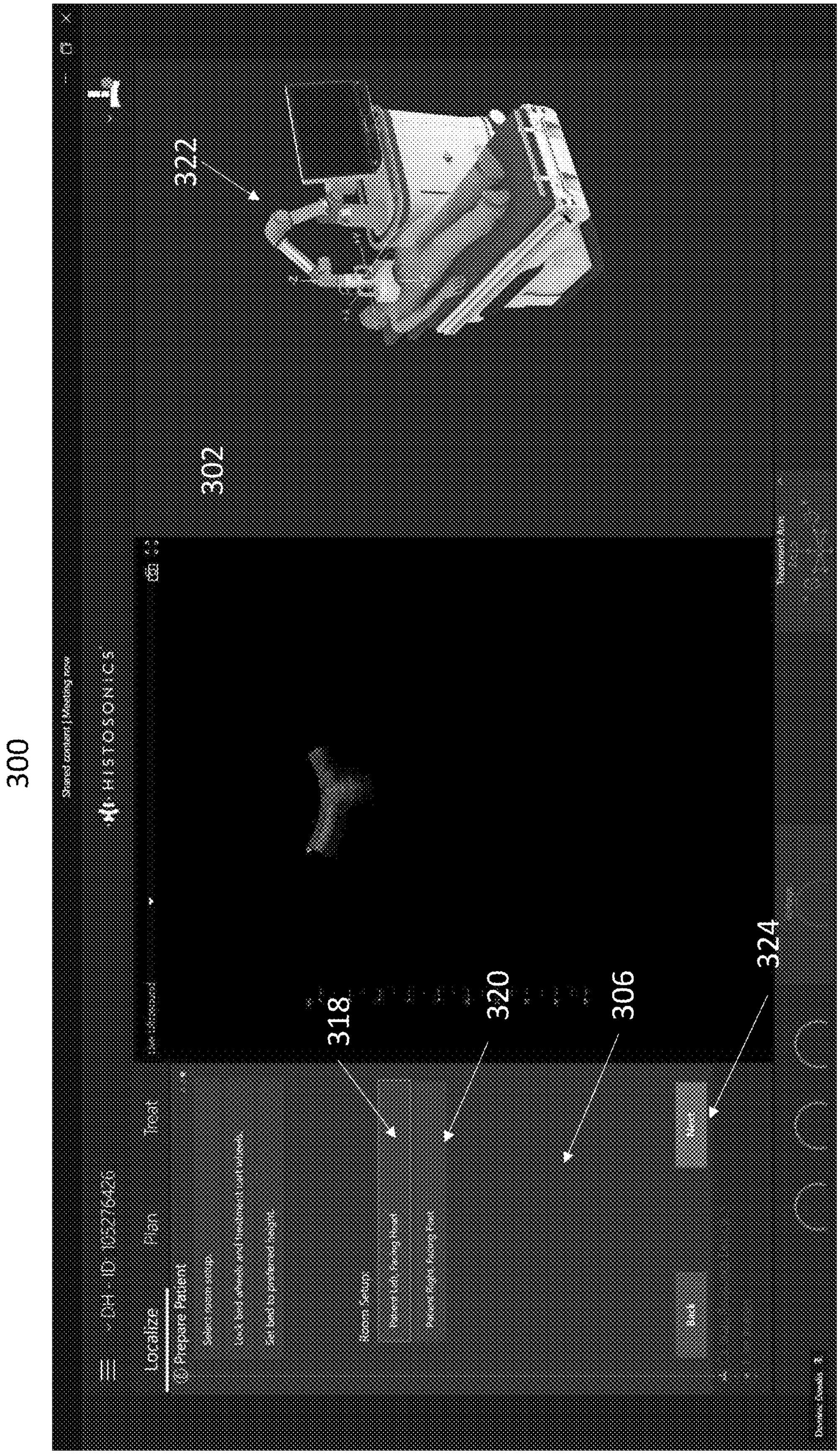

As shown in FIG. 17, the panel 306 is updated to provide instructions on assembly of the bed rail clamp and coupling assembly 46 and placement on the patient. The instructions also provide guidance on filling the coupling assembly 46 with coupling medium and to remove any air pockets between the film or membrane 48 and the patient. For example, in particular, the patient should be removed of any body hair in the intervening external tissue (e.g., abdominal area) such that air pockets adjacent hair follicles are minimized. Selection of the next button 316 advances the workflow to FIGS. 18 and 19, where buttons 318 and 320 alter the image displayed in fields 302 to depict an image 322 of the Histotripsy system 10 in one of two different patient orientations or room set-ups at step 412. This selection of orientation is employed to provide orientation information that is employed by the robotic arm 14 and the software for driving the robotic arm 14 to effectuate image capture with the imaging probe 22 and application of therapy with the therapy transducer 18. One aspect of this orientation is defining which is the Y+ and Y− direction, as can be seen by comparison of FIGS. 18 and 19. Once one of the buttons 318 or 320 is selected defining the orientation of the Histotripsy system 10, and other set-up aspects such as locking the cart 12 or the bed or setting the bed height, the next button 324 can be selected. Alternatively, patient orientation may be selected later in the localizing phase of the histotripsy set-up.

Figure 20:
Figure 21:
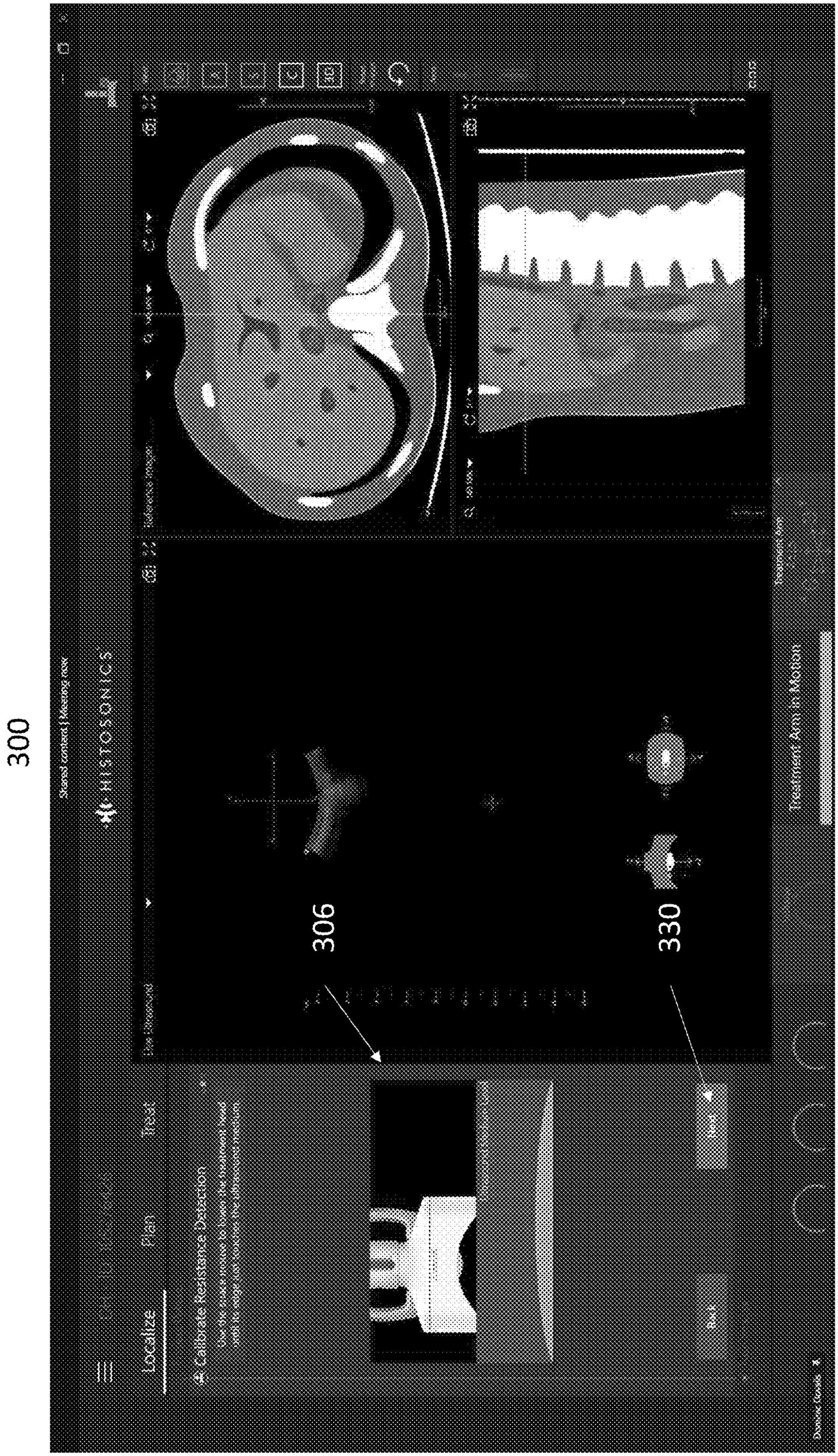

Selection of the next button 324 advances the method 400 to a calibration phase 414 as depicted in FIG. 20. At step 416 a level treatment head button 326 can be selected, whereby the robotic arm 14 will drive the treatment head 20 such that it is in a level position (e.g., parallel with the surface of the coupling medium within the coupling assembly 46). Following levelling of the treatment head 20, the next button 328 can be selected and the workflow advances to FIG. 21, where the UI 300 is updated such that panel 306 directs the movement of the treatment head until just the distal portion (distal to user) of the treatment head 20 touches the surface of the coupling medium contained in the coupling assembly 46 as shown in the instruction image in panel 306 of FIG. 21. The treatment head 20 may be moved using, for example, the space mouse 36 at step 418. During this step, the system 10 may automatically disable rotation of the robotic arm 14 so that the treatment head 20 remains level relative to the surface of the coupling medium. Once the treatment head 20 is positioned such that the distal portion or edge is just in contact with the coupling medium at step 418, the next button 330 can be selected and the workflow advances to FIG. 22.

Figure 22:

Selecting the next button 330 at the end of step 418 sets the reference point for the software application to calculate the buoyancy of the treatment head 20. Throughout the rest of the procedure, the buoyancy is subtracted from the force measured by the robotic arm in order to accurately determine real forces applied to the treatment head 20. As shown in FIG. 22, the UI 300 updates panel 306 to direct the submergence of the treatment head 20 to at least a point at which the surface of the coupling medium is above a minimum fill line (which is marked) on the treatment head 20 at step 420. As can be seen in FIG. 22, as the treatment head 20 is submerged in the coupling medium, live ultrasound images from the ultrasound probe 22 are displayed in field 308. During the driving of the treatment head 20, at step 422, the buoyancy of the treatment head 20 is detected and subtracted from measured forces applied to the treatment head 20 (e.g., by the robotic arm 14) to calculate the real force being applied to the treatment head 20. In contrast to FIG. 9, no resistance indicator illuminates when the treatment head is forced into the ultrasound medium because the buoyancy force from moving the treatment head into the coupling medium is being subtracted out of the measured force. At step 424, the buoyancy value is stored in memory associated with the computing device. The method 400 concludes following buoyancy calibration with the selection of the "accept" button 332.

The buoyancy of the treatment head 20 is used to determine force applied to the treatment head 20 as a result of contact with the patient through the film or membrane 48. As will be appreciated, by driving the robotic arm 14, force can be applied by the treatment head 20 on the patient. The buoyancy is a force that generally opposes the movement of the treatment head towards the patient and must be accounted for when calculating the force applied to the patient by the robotic arm. As will be appreciated, application of force on the patient can move or shift the soft tissues of the patient, and potentially result in movement of the treatment volume, lesion or tumor being treated leading to image fusion issues as described below. Though the ultrasound probe 22 may not necessarily contact the membrane 48 and impart force on the patient, in some instances such contact and application of force is necessary to ensure that the application of therapy from the therapy transducer 18 reaches the −Z distal-most (from the treatment head 20) portions of the lesion or tumor. As noted above, a resistance indicator 222 as depicted in FIG. 9 provides a visual signal of the resistance to movement experienced by the robotic arm, and in some instances can limit further movement of the transducer head or interrupt application of therapy when certain thresholds are experienced. Indeed, the measured values, and related calibration values and/or methods, may be further utilized during the procedure to ensure the system accounts for and can react to, various force scenarios, some of which may require pausing, terminating and/or reinitiating various steps of the procedure and/or therapy.

Fusion

Figure 23:
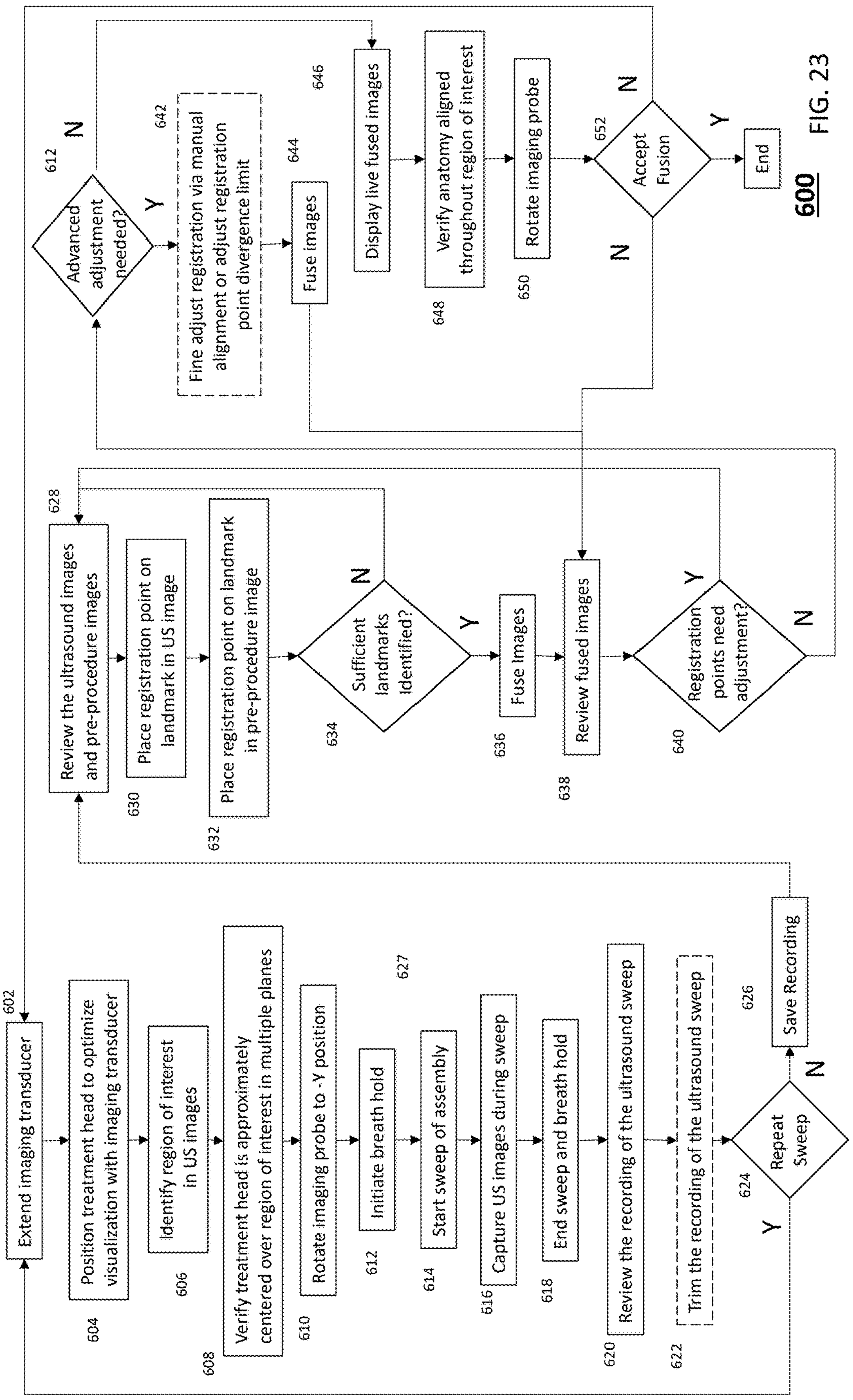
FIG. 23 depicts a flowchart outlining a method for generating a fused image data set for display in a user interface of the histotripsy system of FIG. 1 in accordance with the disclosure.
Figure 24:
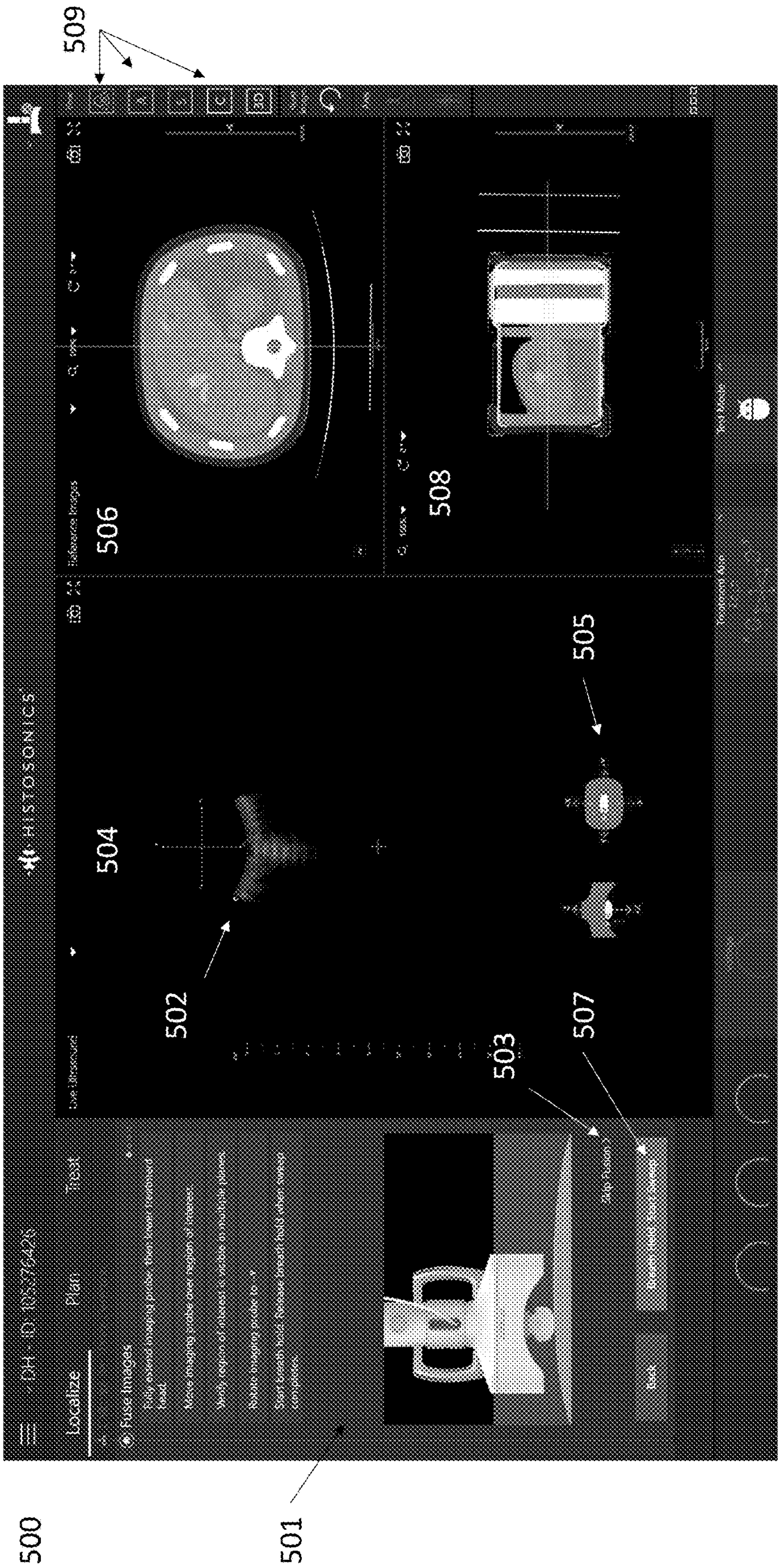
FIGS. 24-32 depict a series of user-interface images following the steps of the flowchart of FIG. 23 in accordance with the disclosure.

FIG. 23 is a flowchart describing a method 600 of forming a fused image combining ultrasound and pre- or peri-procedural images for use in planning and undertaking a treatment of a patient. Following completion of method 400, once the buoyancy is detected and real force calibration is complete (See FIG. 22), an ultrasonic 3D volume can be captured of a region of interest in which the target to be treated is visualized. That captured 3D volume can be then fused with pre- or -peri-procedural images (e.g., MRI, CT, CBCT, X-ray images, and/or any other appropriate medical imaging), and subsequently the location of the live (2D) ultrasound image can be spatially determined relative to the pre- or -peri-procedural image volume. To begin the fusion process a user-interface (UI) 500, as shown in FIG. 24, is depicted in the display 24 of the Histotripsy system 10. Note that a skip fusion button 503 may be selected before or at any point during the fusion process to skip the process described herein below entirely and proceed to a planning phase, described below, without undertaking a fusion process.

Following the instructions on the UI 500, at step 602 the imaging probe 22 is extended from the treatment head 20 such that it extends beyond the therapy transducer 18 and the user can drive the robotic arm 14 and treatment head 20 to locate a target area or region of interest using for example the space mouse 36. During the process, live ultrasound images 502 are acquired and displayed in a panel 504 of the UI 500. Reference images selected during the session (see FIGS. 12 and 13) are displayed in panels 506 and 508, and the views displayed in the panels 504, 506, or 508 can be adjusted using buttons 509. At step 604 the treatment head 20 is placed to optimize visualization of the target. At step 606, the treatment head 20 and imaging probe 22 are moved to place the region of interest and particularly the lesion, if visible, in the center of the ultrasound image (as its displayed on the UI). At step 608, the imaging probe 22 is rotated to verify the region of interest in multiple planes (e.g., sagittal and axial) using the orientation tab 40 to ensure that the visualization of the region of interest and particularly the lesion is approximately centered in the ultrasound images in multiple planes.

Figure 25:
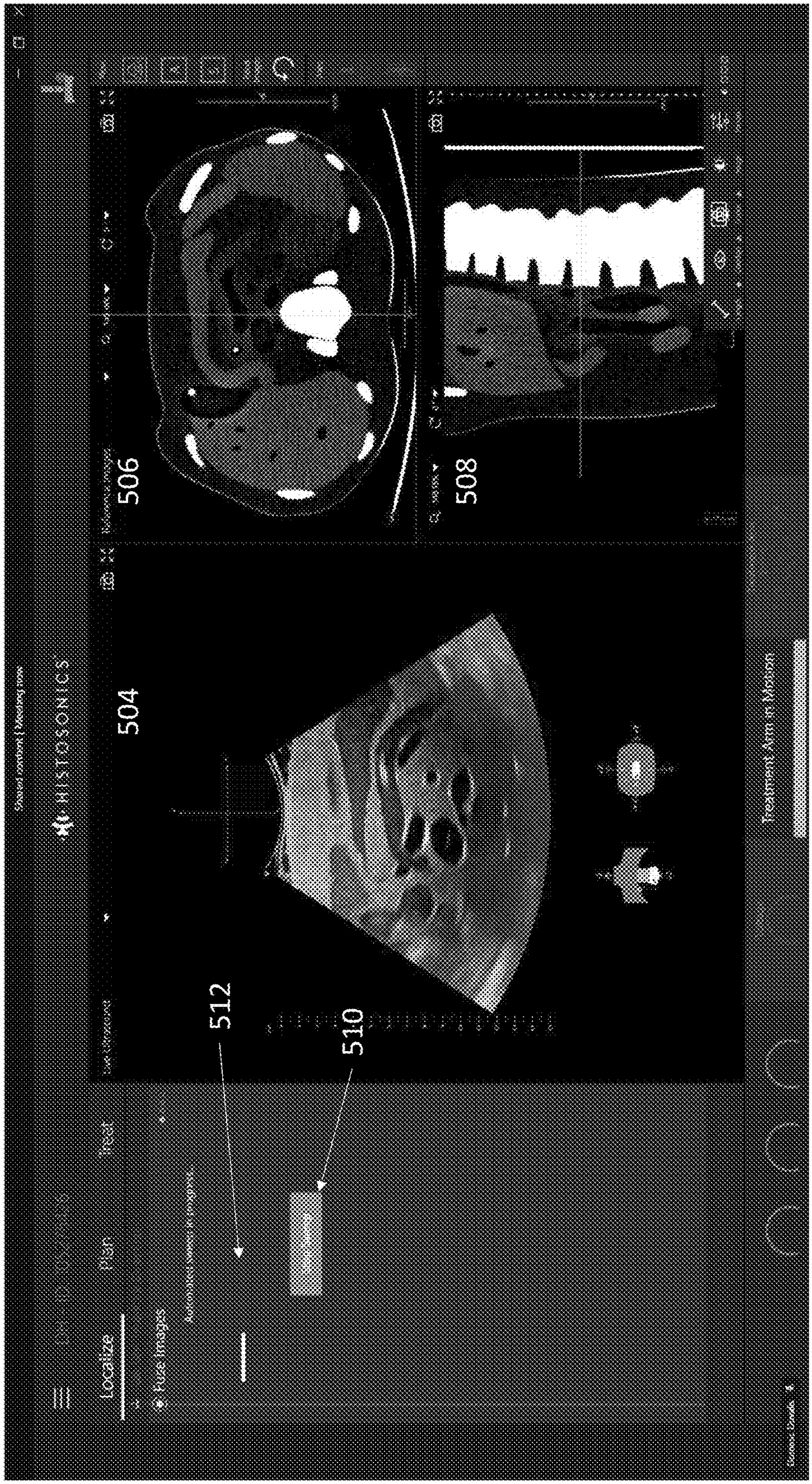

At step 610 the imaging probe is moved to the −Y position, as depicted in imaging probe position indicators 505. Once the imaging probe 22 is so positioned, a breath hold may be initiated on the patient to minimize movement of the patient caused by respiration at step 612 and an ultrasound sweep is initiated at step 614 by selection of button 507. The breath hold may be continued for the duration of the ultrasound sweep, and in some embodiments, the ultrasound sweep time is less than the breath hold. During the ultrasound sweep, as shown in FIG. 25, the treatment head 20, driven by the robotic arm 14 is moved along the X-axis, about 30 degrees in −X and about 30 degrees in the +X directions from the starting location. In other embodiments, dependent on the imaging probe, patient size and/or orientation, the ultrasound sweep could be as little as 15 degrees in both −X and +X directions or is much as 45 degrees in both −X and +X directions. A progress indicator 512 on the UI 500 shows the progress of the sweep, as noted above, movement of the treatment head 20 during the sweep is along the X-axis. Ultrasound images are captured at any point or at multiple points along the sweep at step 616. Further, more than one ultrasound image may be associated with a specific point along the sweep, however, data is typically recorded/saved for only one sweep. The sweep may be configured to motion in a specific direction (e.g., an arc or rotation of a specified distance or degree, etc.). In one configuration, the sweep moves first to the −X angle and then towards the +X angle which is typically from the direction of the patient's feet toward the patient's head, however, this is dependent upon the orientation of the patient relative to the system that was specified in step 412. This direction may be changed in different embodiments. Upon completion of the sweep at step 618, the robotic arm 16 and treatment head 20 stop motion and ultrasound imaging is stopped, as is the breath hold. During the sweep, if movement of the robotic arm 14 and the treatment head 20 exceeds a threshold force, the sweep will automatically stop motion and move in the opposite direction. For example, if the treatment head 20 came into contact with another part of the system, for example, a portion of the coupling assembly 46, while moving in the −X angle the threshold force will be triggered and the motion of the treatment head 20 will be stopped and redirected in the opposite direction (towards the +X angle). Likewise, during the sweep the user has the ability to input a command to stop motion in the current direction via the stop sweep button 510. For example, if the user wants the sweep motion to stop before reaching the −X angle they can select the stop sweep button 510 which will stop motion will in the −X direction and then start motion in the +X direction. The system may display real-time force monitoring feedback in the system UI including force notifications via text, color coded force states, graphics and overlays, and/or other features. In some embodiments, the system UI may notify/display for users the location of the location of the source feedback (e.g., transducer housing corner, translated ultrasound imaging probe, etc.).

Figure 26:
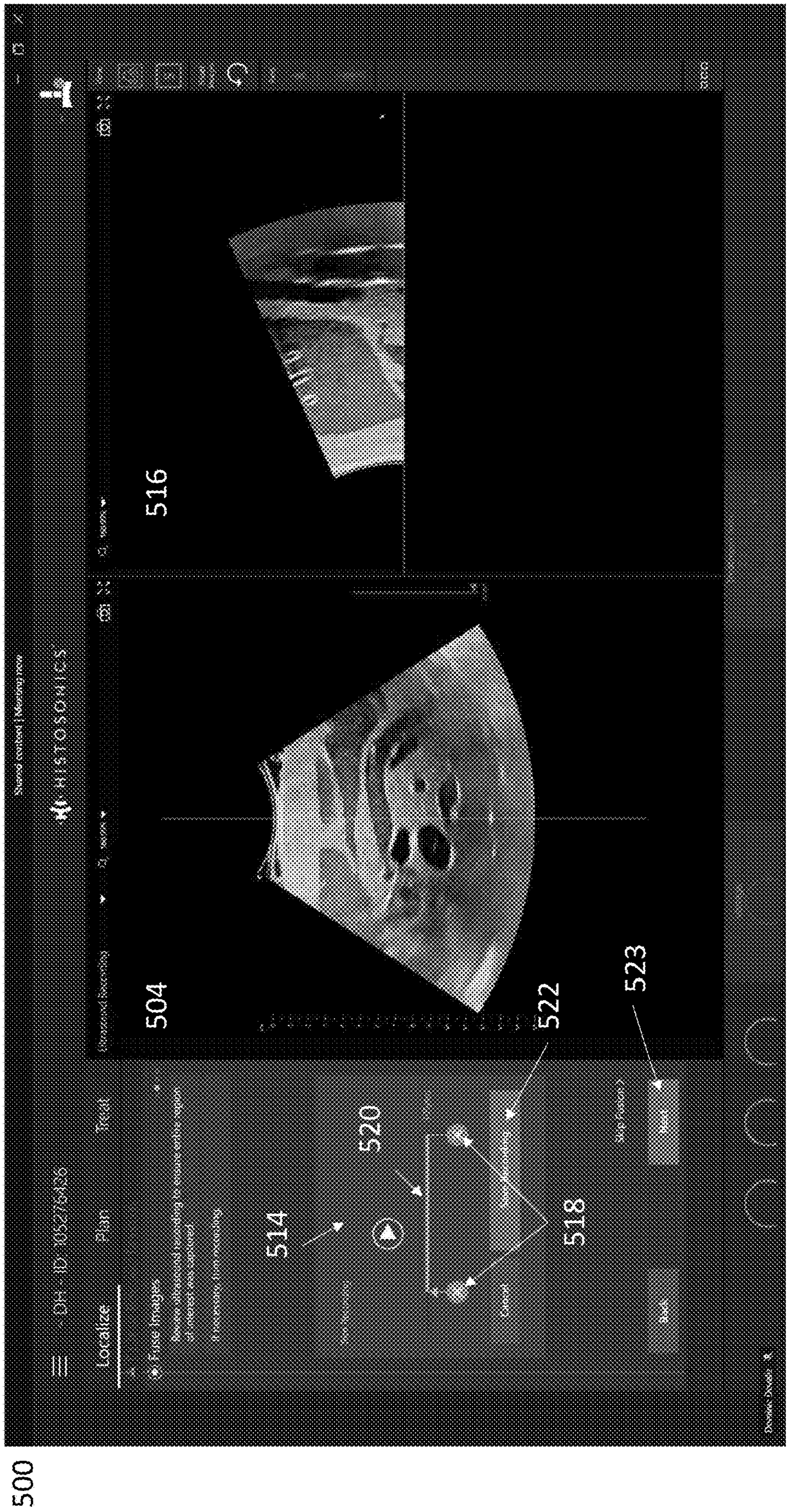

At step 620 a review images panel 514 is depicted on the UI 500 (FIG. 26). The review images window 514 allows a user to review all of the images from the sweep by playing them as a video. The goal of the reviewing of the sweep is to ensure that the region of interest (including any anatomical landmarks and structures), and particularly the lesion or target for the histotripsy was fully captured in the sweep. As shown in FIG. 26 the review images window 514 also allows portion of the ultrasound sweep to be trimmed or clipped. This may be appropriate in instances where the sweep included images that did not include the region of interest or user would like those images removed for various reasons. The trimming of the recording of the ultrasound images is an optional step 622. The review images window 514 also allows for the sweep to be repeated at step 624, by cancelling the sweep, or selecting the "back" button the user can repeat the sweep which returns the method to step 602. While panel 504 shows the ultrasound images in their standard planar view, a second panel 516 shows the ultrasound images that were collated into a 3D volume from a side view orthogonal to the direction of the sweep. The collation into a 3D volume may be achieved by associating each captured image (or frame) with a robotic position and time stamp to form the volume. As shown in FIG. 26 the sweep comprises 507 images captured during the sweep. By selecting one of the trim buttons 518 and dragging them along the recording line 520, the ultrasound images associated with that point in the sweep are displayed in the panel 504 as shown in FIG. 26. In this manner, a user can adjust the trim buttons 518 to reduce the number of ultrasound images of the sweep. The movement of the trim buttons 518 along the recording line 520 provides an indication of the portion of the sweep that the user would like to trim or remove from the sweep. The goal of trimming the sweep is to remove any ultrasound images that do not contain clear data such as images taken over bowel, lung or blocking anatomy such as rib, which could impede the image based fusion algorithm from optimally matching the ultrasound image data to the pre- or peri-procedural images. As such, in some examples, sweeps may be taken over and/or in between ribs to allow fusion using a transcostal and/or intracostal approach. As can be seen in FIG. 26, moving of the trim button 518 advances to the 105$^{th}$ image of the 507 captured images. Once the trim buttons 518 have been utilized and unnecessary ultrasound images (e.g., images 1-104) have been eliminated, the save recoding button 522 can be selected at step 626 to save the selected ultrasound images. As will be appreciated, the trim buttons 518 need not always be employed, and the save recording button 522 may be selected without any trimming. Further, trimming can be performed or displayed with other UI screen indicators, such as a progress bar, ellipse, or other visual indicators or pop-up buttons not illustrated.

Figure 27:
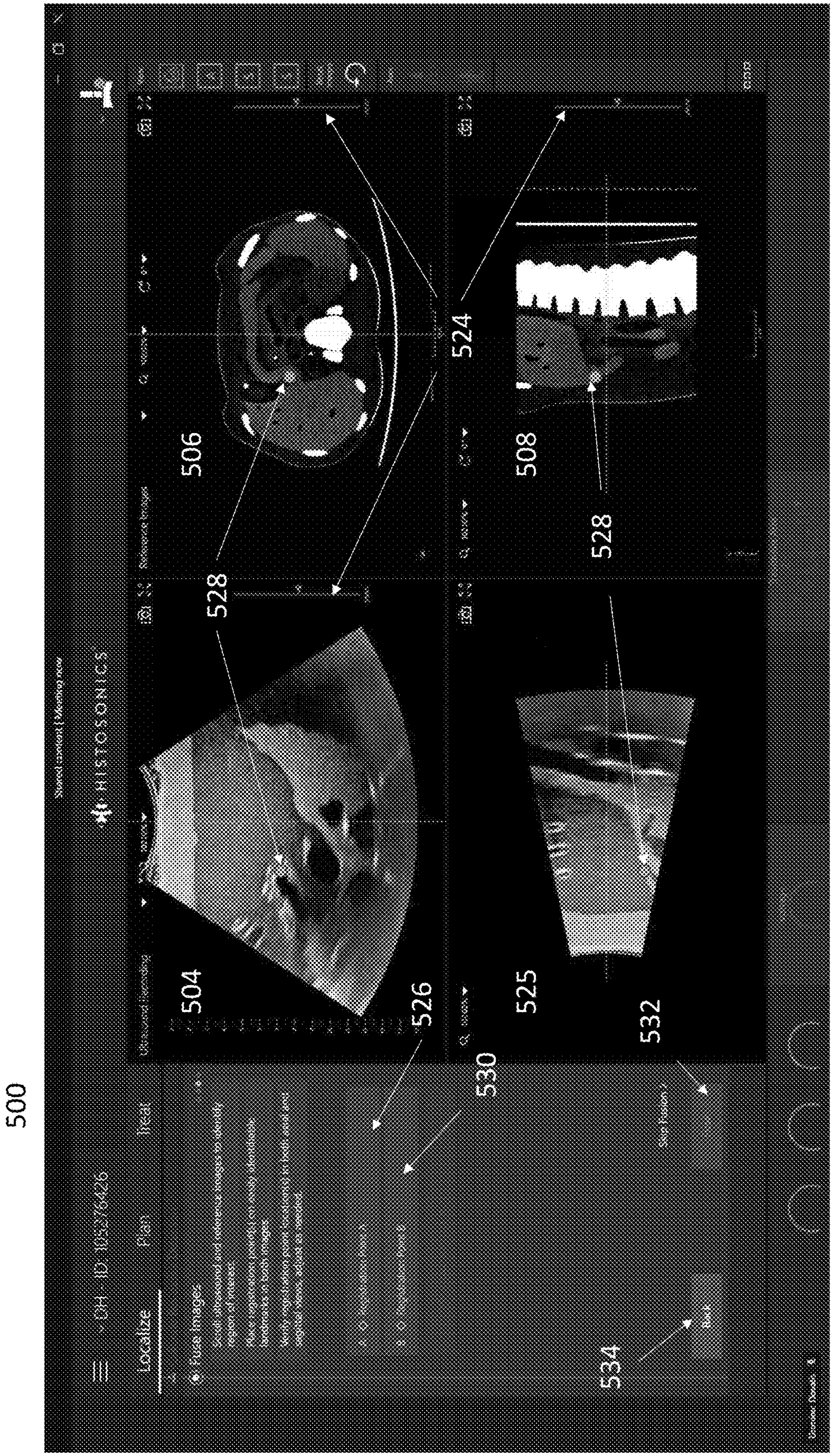

If the fusion step is not skipped, and once the recording is saved at step 626, the next button 523 is selected and the workflow progress to the UI 500 depicted in FIG. 27. In FIG. 27, registration of the ultrasound images to the pre-procedural reference images is undertaken. Panel 504 depicts the ultrasound image volumes in their standard orientation, and panel 525 shows those same ultrasound image(s) volume but in a sagittal view. Panel 506 depicts the axial view of the reference or pre-procedure image volumes, and panel 508 depicts a sagittal view of the same pre-procedure image volume. Sliders 524 allow for a user to change the image within the volume being displayed in each the panes. Though described here using the sliders on the UI 500, those of skill in the art will understand that the display 24 may be a touchscreen or the trackpad 34, or other input device may be used to effectuate the scroll or manipulation of images herein (2D and 3D). In accordance with the disclosure at step 628, the ultrasound image volume in panel 504 and the pre-procedure image volume in panel 506 can be scrolled through to identify landmarks or structures (endogenous and/or exogenous) which appear in both the ultrasound images and the pre-procedure images. These may include vessels, ducts, nerves, organ surfaces, organ/tissue structures, layers and/or components, and/or if exogenous, may include various forms of fiducial markers or devices visible under multiple forms of imaging. The user may scan through the various DICOM and ultrasound images either on the touchscreen or trackpad, to locate anatomical landmarks. Additionally, the user may zoom in or out of the image screens to assist in locating the landmarks. One or more of the screens may automatically update/zoom in or out when the user zooms in or out of other views/images. Once such a point is identified in each the "Registration Point A" button 526 can be selected, and a registration point 528 can be placed at the appropriate location on the ultrasound image in panel 504 at step 630 and in the pre-procedure image panel 506 at step 632. The user can optionally also scroll through the sagittal images in panels 508 and 525 to confirm the landmark prior to or after placing the registration points 528 in the images in panels 504 and 506. If the placement of the registration point 528 is adjusted in one of the sagittal plane views 525 or 508, the position of the registration point 528 will be updated in the axial views shown in panels 504 and 506. If sufficient landmarks for registration have not been placed at step 634, the method may return to step 628 with selection of the "Registration Point B" button 530, and another registration point 528 can be placed in the ultrasound and pre-procedural image volume. This process of identifying landmarks and placing registration points 528 may be repeated 2, 3, 4, 5, 6, or more times. In some instances, where a fine adjustment of position of the marker is desired, cardinal arrows (not shown) pointing in four orthogonal directions from the registration point 528 may appear in one or more of the panels 504, 506, 508, and 525 enabling fine adjustment of the position of registration point 528. In certain embodiments, it may be preferable to place the registration points in the same plane (e.g., axial, sagittal, coronal). In some embodiments, the UI may display the imaging planes with the overlay of the treatment head/therapy acoustic field lines/volume and transducer z-axis (coaxially aligned with the ultrasound imaging probe), to allow contextual viewing to the real-time patient setup, including with various forms of 3D patient models as well as 4D models including motion modeling of the organ, target and/or tumor in context to the treatment plan.

As will be appreciated, to improve the rigid and/or deformable registration of the ultrasound and pre-procedural images, it may be desirable to place markers as close to the tumor or lesion as possible. This could include the center of the lesion or target, if visible in the ultrasound, or at a boundary of the lesion or tumor, however, other locations away from the lesion may also be employed. In one embodiment these locations are within about 5 cm of the lesion or tumor. This proximity assists in compensating for any deformation of the soft tissues of the patient caused by the placement of the coupling assembly (and medium) on the patient's chest. The volume of the coupling medium is generally between about 10 and 20 liters of fluid, and the weight of any portion of this fluid may compress the soft tissues causing them to shift from the positions they were in during the capture of the pre-procedure images. By finding landmarks in proximity to the lesion or tumor, ultimately the target for therapy, the registration in this area is enhanced, and the effects of compression the coupling medium reduced. In some examples, peri-procedural imaging (MRI, CT, CBCT, etc.) may be acquired with patient coupling in place to allow for accounting of any body deformation due to coupling itself. In other examples, the patient baseline pre-procedural imaging may be acquired in the appropriate set up position for treatment. For example, if treatment is to be conducted in the lateral decubitis position, pre/peri-procedural images may be acquired in this position.

Figure 28:
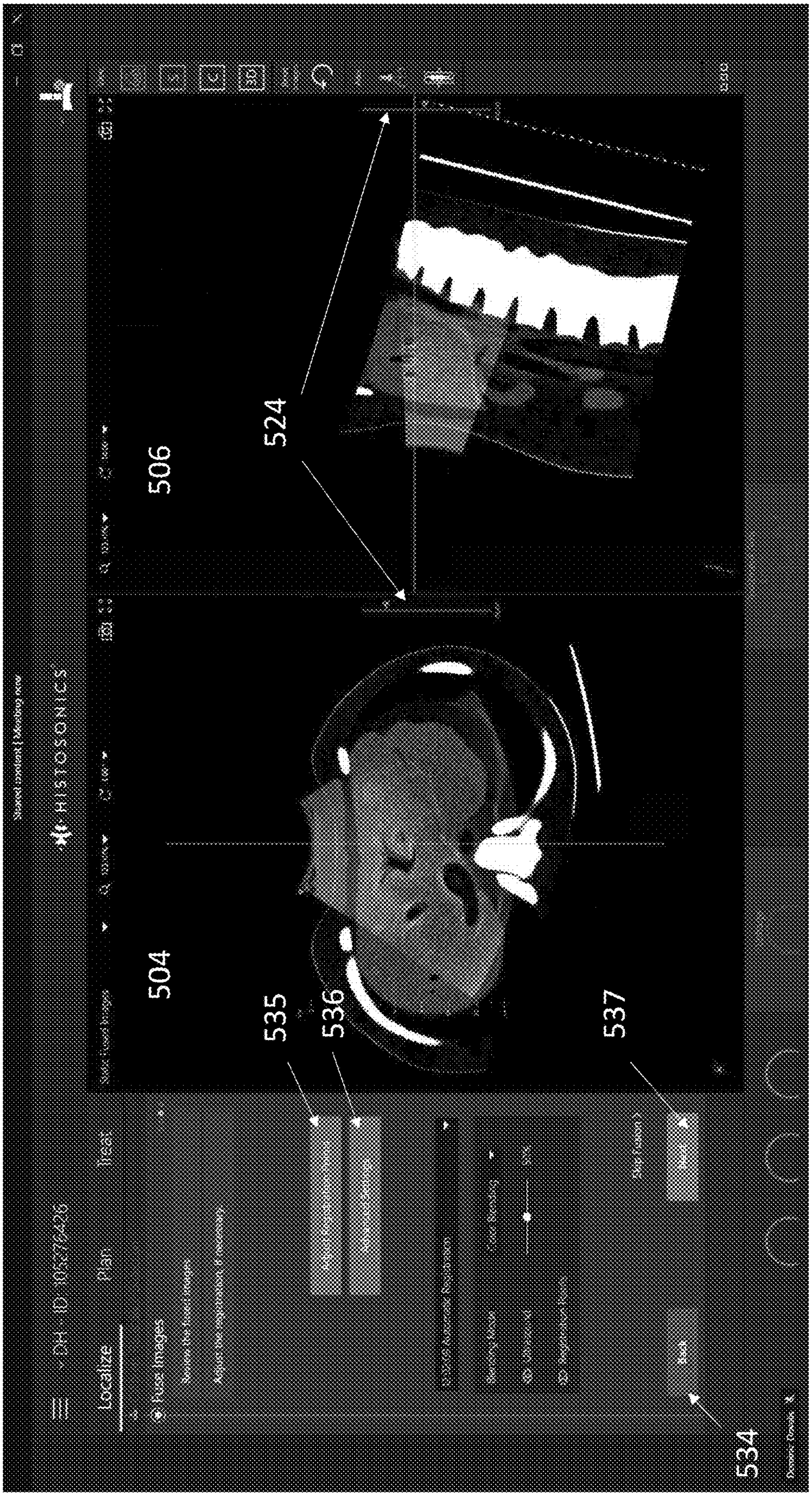

If at step 634 sufficient landmarks or structures have been identified, the fuse button 532 can be selected, and the application stored on the memory in the computing device on the cart 12 fuses the pre- or peri-procedure images with the ultrasound images to displays the axial view in panel 504 and the sagittal view in panel 506 in FIG. 28.

To perform a fusion of images a variety of different methods may be employed as is known in the art. An exemplary fusion process can include a process which involves steps such as first, grossly orienting the ultrasound and pre-procedural or peri-procedural image volumes based on the system-to-patient orientations, such as that set at 412, above. Next, the fusion process may seek to align the marked registration points in both the ultrasound images and the pre-procedural or peri-procedural images to be spatially within 10 cm of each other. Next, a deformation model can be applied to the pre-procedural or peri-procedural image volume to account for compression due to the coupling medium being placed on the patient. The ultrasound volume does not require the deformation model because the images acquired via the ultrasound sweep already reflect the deformation from the coupling medium. Finally, an image-based algorithm is engaged which seeks to match structures between the two image volumes. The result is a registration and ultimately a fusion of the ultrasound images from the ultrasound sweep and the pre-procedural or peri-procedural images as depicted in FIG. 28. In other examples, an automatic registration algorithm may be utilized as a first fusion step and further refined/updated with landmarks and/or structures as a secondary step.

The sliders 524 allow a user to scroll through the fused images in both panels 504 and 506 and view the fused images (step 638) to determine whether the fusion is sufficiently close to enable planning of a therapy volume and treatment plan (described below).

If adjustments may be required (yes at step 640) there are two options, first a back button 534 may be selected, returning the method to step 628 to move or place new markers 528 as described above. Upon selecting the fuse button 532 (FIG. 27) after adjusting registration points a new fusion is generated. Alternatively, if smaller changes are needed, an adjust registration points button 535 may be selected in FIG. 28 which returns to a screen equivalent to FIG. 27, however, following adjustments when the fuse button 532 is selected the fusion algorithm starts from the previous fusion result and modifies it based on the updated registration points.

If registration point adjustments are not sufficient to result in an acceptable fusion, advanced adjustments (yes at step 641) are available through the Advanced Settings button 536 (FIG. 28). When the Advanced Settings button 536 is selected the workflow progresses to FIG. 29 and step 642, which provides two options for manual alignment of the reference images (the pre-procedural or peri-procedural images) so that they align with the ultrasound images. By selecting the drag button 538 the pre-procedural or peri-procedural images in any plane selected can be dragged to improve the alignment with the ultrasound images. Similarly, button 540 allows the user to rotate the reference images (i.e., the pre-procedural or peri-procedural) images to improve the alignment of the fused images. To further assist in this alignment, a blending mode field 542 is provided. The blending mode field 542 includes a slider 543 for adjusting the opacity of the reference or pre-procedure images, as well as a toggle 544 for turning on and off the display of the ultrasound images and the registration points 528. As will be appreciated, turning on and off the display ultrasound images will allow for closer inspection of the pre and/or peri-procedure images, similarly changing the opacity of the pre-procedure images can assist in reducing obscuring features of one image data set as it is fused with the other. The toggle 544 allowing the toggling off the display of the registration points 528 allows for the images to be adjusted without necessarily considering the locations of the registration points on the images. As will be appreciated, the slider 543 and toggle 544 can be used in various combinations as the user observes the changes to the UI 500 in an effort to adjust the alignment of the ultrasound and the pre-procedure images. The blending, rotations, and dragging of images may be repeatedly adjusted and assessed, including re-marking of the registration points until the user has obtained an acceptable fusion.

Figure 30:
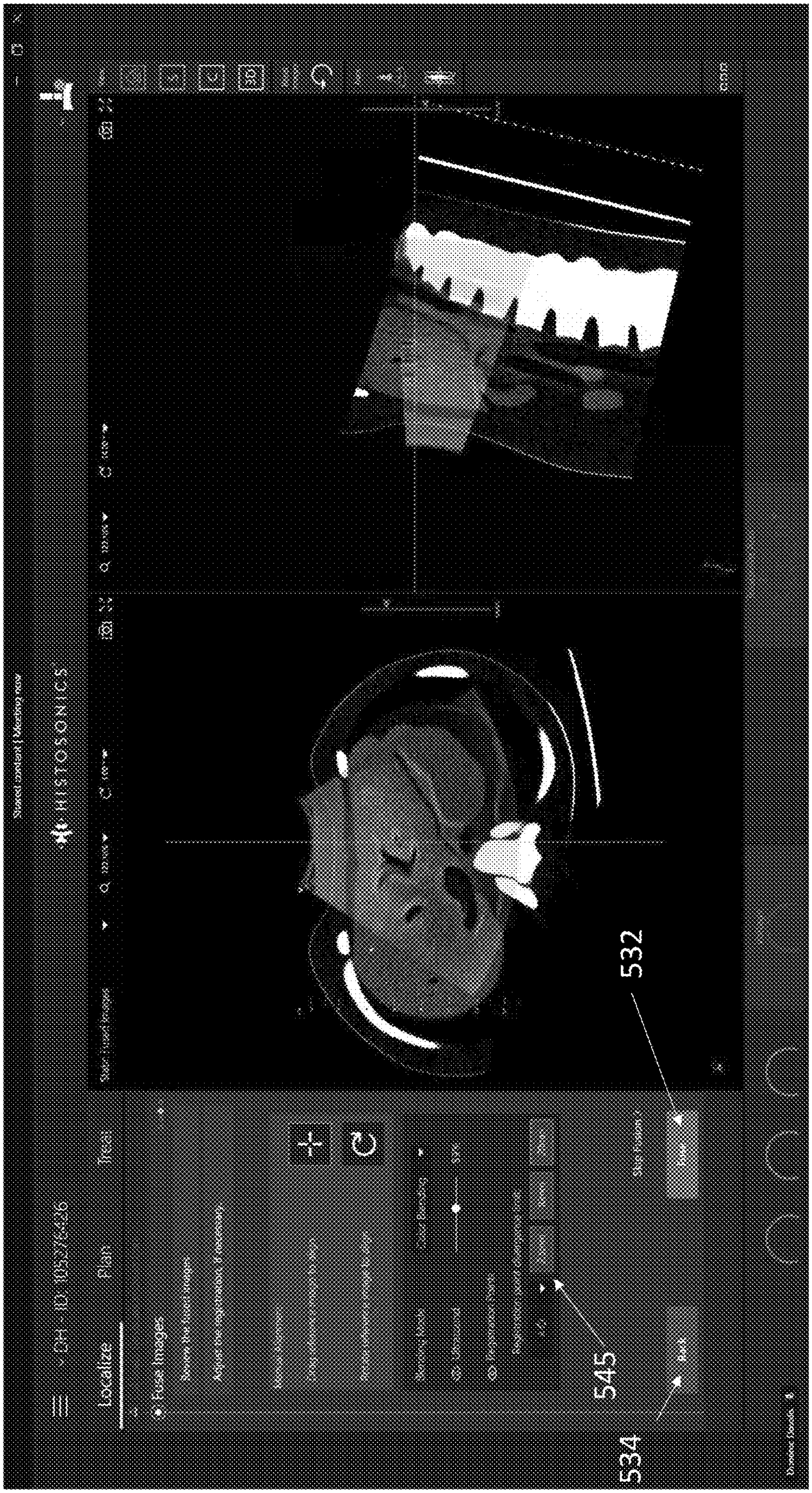

FIG. 30 shows an additional aspect of the blending mode field 542 available when display of registration points 528 are toggled on, a registration point divergence limit 545. This limit, which may be selected by the user, allows for a certain level of divergence in the location of the registration points marked in the two image data sets after fusion. The smaller the divergence, the closer the registration points 528 must appear in the final fusion of the images, and the greater the divergence, the further apart they may appear and still provide an acceptable fusion of the images. The divergence limit is most helpful when user is either very confident or not very confident in the placement of the registration points. In one aspect, by default, a mid-range (10 mm) divergence limit is set. If the clinician is very confident of the fusion, they might seek to improve the fusion by tightening the divergence limit. If the clinician is not confident of the fusion, and not confident that same landmarks/anatomical locations are actually marked in both image sets, they might seek to improve their fusion by loosening the divergence limit.

Once all desired manual alignments are completed and the desired divergence set the fuse button 532 may be selected and the application again fuses the pre-procedural or peri-procedure images with the ultrasound images, taking into account the adjustment made, and then returns to step 638 for review of the fusion where the axial view in panel 504 and the sagittal view in panel 506 are displayed as shown in per FIG. 28.

If the fusion is acceptable (no at steps 640 and 641), the live fusion can be undertaken by selecting the next button 537 (FIG. 28). At step 646 the pre-procedural or peri-procedural images are fused with the live ultrasound images from the ultrasound probe 22 and displayed in panels 504 and 506 at step 646 and shown in FIG. 31.

Figure 29:

The images appear in FIGS. 28-30 are static fused images, that is they are static fusions of the ultrasound images from the sweep and the pre-procedure images. Because these images were captured using the robotic arm 14, the position of the treatment head 20 and particularly the ultrasound probe 22 at which each image was captured in known and stored in the memory of the computing device. By registering these static images, and adjusting the registration points 528, the histotripsy system 10 is able to subsequently fuse live streaming ultrasound images the position at which they are captured with the pre-procedure images as depicted in FIG. 31.

Figure 31:

Once live fusion is available as in FIG. 31, the user can verify that the anatomy is aligned throughout the region of interest (e.g., a lesion or tumor or area of unwanted tissue). This can be done by using the space mouse 36 to move/position the robotic arm 14 with the treatment head 20 and imaging probe over the region of interest and observing the fusion through this area at step 648. Any movement of the treatment head 20 and therewith the therapy transducer 18 and the imaging probe 22, whether robotically or manually, is accurately represented in conjunction with a change in the view of the pre-procedural images. As part of this verification the imaging probe 22 may be rotated at step 650 to confirm anatomy alignment in multiple planes. As shown in FIG. 31 with reference to panel 506 the outline 546 of the original ultrasound sweep image volume is projected on the sagittal view. This enables the user to observe whether the imaging plane that is being displayed in panel 504 is within the range of input data used to generate the fusion to the pre-procedural images. The fusion is expected to remain most accurate as long as the live ultrasound remains within the range of input data. The live fusion images can be moved, rotated, as well as zoomed or panned in and out of to confirm the alignment of the anatomy. At step 652, if the anatomy is aligned in the region of interest around the tumor or lesion, then the accept button 548 can be selected and the fusion process ends, and images displayed in the UI 500 or subsequent UI's in the workflow (described below) will show the live fused images. As can be seen in FIG. 31, the registration points 528 may no longer be shown in the live fused images. If the fusion is not acceptable to the user the back button 534 may be selected which returns the method to step 638 for renewed fine adjustment, or a repeat sweep button 550 may be selected which return the method to step 602 to restart the fusion process.

A number of reasons may result in the fusion being unacceptable. First the ultrasound sweep images were acquired during a breath hold with the lungs generally inflated, which can cause some movement of the anatomy within the patient. In contrast the live ultrasound images are acquired during normal tidal breathing. Secondly, the registration points may not have been correctly identified in the separate imaging data, or they may have been selected too far from the tumor or lesion. Further, the divergence limit may have been selected to large, resulting in potential mismatches of images. Any or all of these along with other bases may be the cause of an unacceptable fusion requiring a renewed adjustment or even a re-sweep of the ultrasound probe 22.

Figure 32:
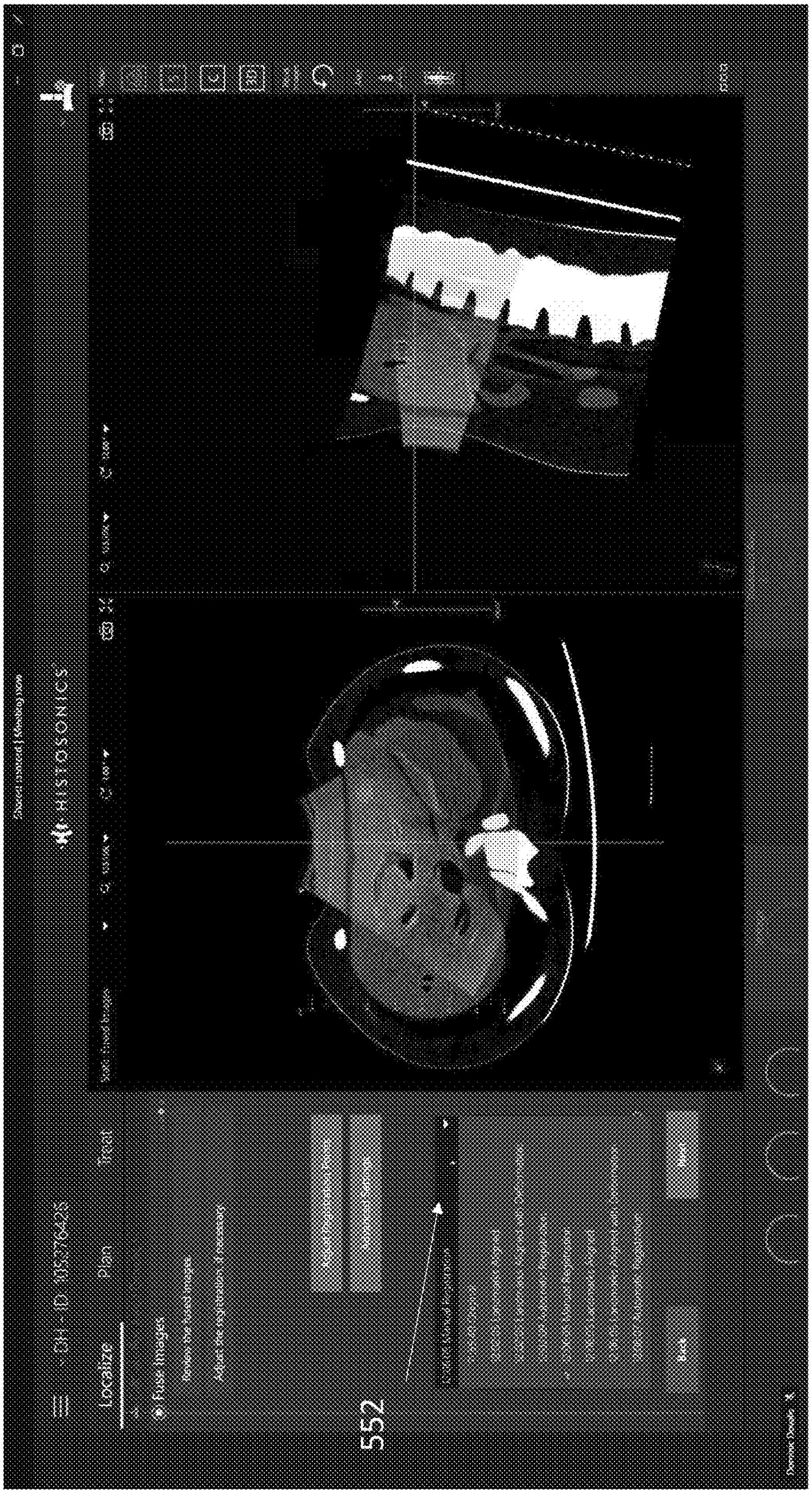
Figure 33A:
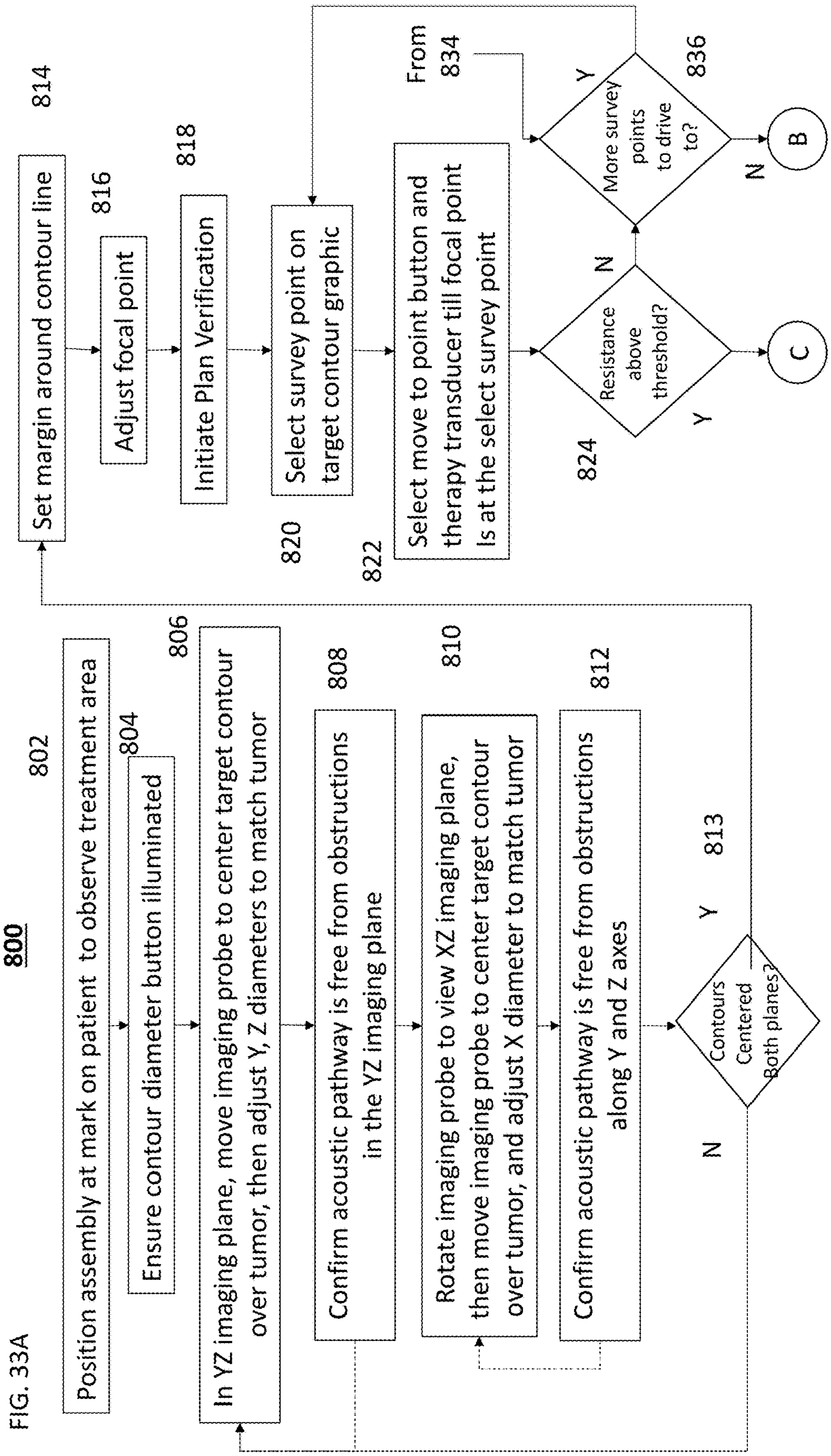
FIGS. 33A and 33B depict a flowchart outlining a method of planning a histotripsy procedure in accordance with the disclosure.
Figure 33B:
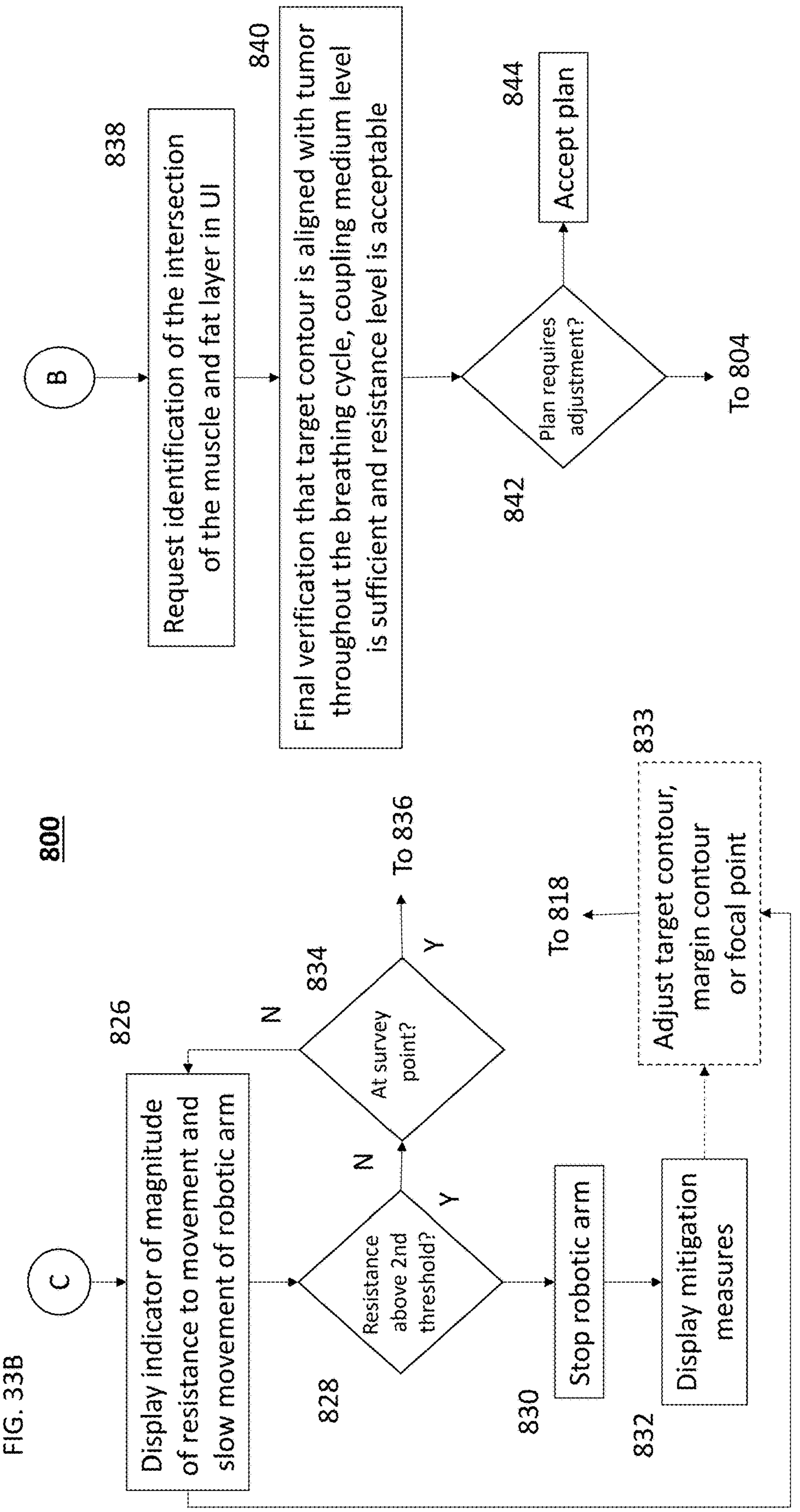

FIG. 32 depicts a further feature with drop down 552 which list of fusion results available for review at step 638. The drop down 552 allows the clinician to troubleshoot their fusion result by comparing results with different inputs (example: adjusting registration points) or gives them an option to select an earlier result with which to proceed to live fusion review. In this manner, the clinician can make multiple attempts to perfect the alignment and compare the results until achieving an acceptable fusion.

In other embodiments, the DICOM data comprising the pre-procedure imaging may also be modified in various manners, including various segmentations (organs, structures, unwanted tissue volumes, etc.), pre-plans comprising simulated contours and placement of, and/or other visualization features that may be used to inform targeting and localization and treatment planning in subsequent work-flow steps. In some examples, treatment plans may be displayed over the pre-plans, including the display of the contours (described in greater detail below) with may be distinct in their features from the pre-plan (e.g., represented as a different line type, thickness and color than the "contours").

Planning

Figure 34:
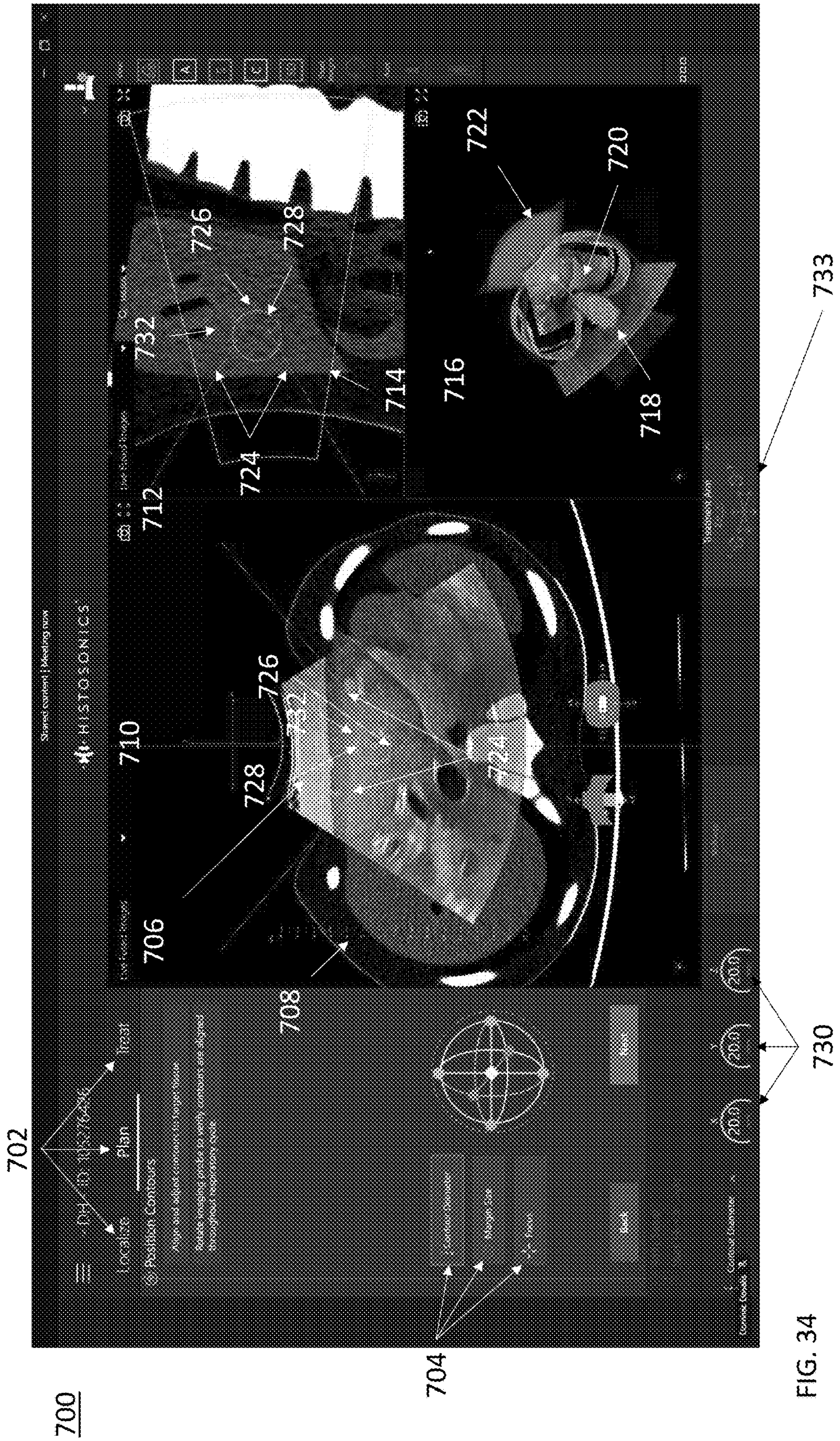
FIGS. 34-40 depict a series of user-interface images following the steps of the flowchart of FIGS. 33A and 33B in accordance with the disclosure.

Following completion of the set-up method 400 the workflow described in this disclosure and optionally the fusion process of method 600, the workflow proceeds to a planning stage. At this stage, the clinician can plan one or more histotripsy therapies for a given patient. The workflow also allows for the clinician to recall and display prior treatment therapies and/or treatment plans so that additional overlapping or non-overlapping therapies can be planned. The UI 700 switches the indicators 702 from highlighting the "Localize" tab to highlighting the "Plan" tab, after planning is completed the "Treat" tab will be highlighted. These tabs allow for a user to understand where in the workflow the user is at any point during the procedure. The planning stage is described in connection with method 800 described by the flow chart in FIGS. 33A and 33B and UI 700 depicted in FIGS. 34-40. FIG. 34 depicts a UI 700 for presentation on the display 24 used in the planning of a histotripsy procedure. Unlike most procedures, this planning occurs in situ with patient in position on the patient surface (e.g., interventional or operating table), thus there is no express need to register pre-procedure images with the live ultrasound images (e.g., the procedure may be purely ultrasound guided). However, as described above, fusion of the pre-procedure or peri-procedural CT, MRI, PET, and/or other image data sets enables display of these images in context with real-time live ultrasound images.

UI 700 includes a number of buttons 704 that allow for different aspects of the planning process that follows to be undertaken. These buttons 704 include a "Contour Diameter" button, "Margin Size" button, and a "Focus" button. In certain embodiments, these buttons 704 may display as "Contour Diameter", "Margin Diameter" and "Focal Steering". It should be understood that Contour Diameter means the contour diameter of the lesion or tumor of interest, which in some embodiments may be up to and including 3 cm. The Margin Size or Margin Diameter provides an additional 0.5 cm around each side of the contour, which for the diameter contour may be about 1 cm in total. In certain embodiments, various combinations of the contour diameter and margin size/diameter may be 4 cm in total. Selection of one of these buttons allows various parameters of the procedure to be planned or adjusted as described hereinbelow. It should be further noted that the various displays on the UI, including but not limited to contours, margins, focal points, and/or indicator/field lines may be selectively displayed or removed from UI display during specific timepoints in the user workflow, which may enable better visualization of the lesion of interest during planning or treatment.

In FIG. 34, and UI 700 the live ultrasound images 706 are displayed in a fused fashion on a corresponding slice 708 of a peri-procedural or pre-procedure image (e.g., CT, MRI, or another image) in field 710, based on the fusion method 600, described above. In field 710 the images depict an ultrasound view which corresponds in this example to an axial view of the patient. A related sagittal view of the ultrasound image 706 fused with a peri- or pre-procedure image is depicted in Field 712. In field 712, an indicator 714 the outline of the ultrasound sweep that was used to generate the fusion, with the purpose of indicating whether the image view overlaps with the original fusion data which indicates the fusion is more reliable. Field 716 depicts a 3D model 718 formed from pre-procedural or peri-procedural images (e.g., a CT or MRI image data set) fused with a live ultrasound image 720. The 3D model 718 is registered with the ultrasound image 720 and displayed as a fusion 3D model with the live ultrasound image 720. The live ultrasound image 720 is displayed in the anatomically correct location in the 3D model 718. As the treatment head 20 and particularly the ultrasound probe 22 is moved above the patient, the ultrasound image 720 and its position within the 3D model is updated accordingly. The 3D model 718 also depicts an acoustic pathway volume 722, which is the volume through which the therapeutic ultrasound emitted from the therapy transducer 18 is to pass before arriving at the focal point where the therapy occurs. Two-dimensional representations of the acoustic pathway volume 722 are displayed in fields 710 and 712 as field lines 724 which terminate at a focal point 726 denoted by a cross or other indicated. The field lines allow the user to understand/visualize potential obstruction and further allow users to minimize (or avoid it if possible) those obstructions. However, it should be understood that in many cases a target tissue volume may not be completely free from obstructions. By default, the focal point 726 is placed at the further point in the −Z direction (deepest within the body of the patient or furthest from the surface of the patient's skin) relative to the target 728 and the margin 732 contours. The positioning of the crosshairs 726 at this location, following steps described below allows the user to confirm a deepest point of therapy is clear of potential obstructions and/or the deepest point of therapy required will receive a histotripsy treatment. As will be appreciated, in the absence of a fusion, no fused images are displayed in Field 710, but rather all the planning steps as described herein below occur on the live ultrasound images, optionally with either pre-procedural or peri-procedural images being displayed in Field 712 to assist the user if they were imported during patient registration.

Upon exiting the localized portions of the workflow (e.g., method 400 followed optionally by method 600 thus either with or without fusion) UI 700 is displayed and an initial target contour 728, is automatically displayed. The target contour 728 is the initial representation of the shape of a tumor or lesion to be treated. In one embodiment, the default target contour 728 has initial dimensions of 20 mm along each of the X, Y, and Z axes, as noted by indicators 730. As described below, the value denoted in the indicators 730 can be adjusted by knobs 28, and thus the target contour 728 can be adjusted to more closely match the target contour 728 to the actual shape and size of the tumor or lesion to be treated. In addition using the space mouse 36 and X, Y and Z knobs 28 functionality the location of the target contour 728 can be moved to a more appropriate location if determined by user. A margin indicator 732 is also depicted around the target contour 728 and depicts a volume of tissue around the target contour 728 that will also receive therapy to ensure that the lesion or tumor is entirely treated. As will be described in detail below, the size of the margin indicator 732 defines a boundary around the target contour 728 that is a set value (e.g., 2, 4, 6 mm) that may also be adjusted by the user or system to increase or decrease the margin around the tumor or lesion being treated.

The method 800 starts with step 802, where the treatment head 20 is positioned using either the freedrive buttons 44 or a space mouse 36 operably connected to the robotic arm 14 such that the imaging probe 22 is located at the general area of the mark optionally placed on the patient in connection at step 408 of method 400. As noted above, the ultrasound probe 22 is capturing ultrasound images for display in field 710, and the treatment head 20 is moved such that the tumor or lesion to be treated can be observed in the live ultrasound images 706. Additionally or alternatively, the tumor or lesion to be treated may be identified using surround/adjacent anatomical landmarks. For example, this may be particularly useful when direct visualization is at least partially obscured or limited. This may require movement of the treatment head 20 around the mark to ensure that an acoustic pathway volume 722 and field lines 724 are substantially free from obstructions or blockage (e.g., ribs, cartilage, bowel, GI gas, etc.) that can impact the energy requirements to effectuate therapy of the lesion or tumor.

The UI 700 is configured to allow a user to create and display a planned treatment volume. As noted above, planned treatment volume includes a target contour 728, around the tumor or lesion and a margin contour 732, around the target contour 728. Both margin contour 732 and target contour 728 are configurable by the user. Further a default configuration, as shown in FIG. 34 may vary in size and shape based on application or organ area of intended use (e.g., liver, kidney, thyroid, breast, etc.). Further both the target contour 728 and margin contour 732 may have system imposed limits (e.g., minimum or maximum size or eccentricity, etc.).

A planned treatment volume may be displayed to users through the UI 700 in various ways, including but not limited to 2D views of fields 710 and 712 or the 3D model of field 716, and using real-time or live streaming imaging data, or previously collected pre-procedure images (CT, MRI, etc.), or peri-procedural imaging acquired during the procedure (cone beam CT, intraoperative CT, etc.) that are fused to the real-time imaging data. The planned treatment volume may be displayed as graphical features or computer-generated overlays or models, which may further display key plan features or therapy transducer related features analogous to the acoustic field lines including a geometric focus or focal points 726, default therapy focus based on predicted aberration/attenuation, and such features may change position or location dynamically based on motion of the robot or position of the imaging probe 22. Further details of generation of the treatment volume and displaying the treatment volume on the UI 700 are outlined in conjunction with method 800 below.

Upon entry into the UI 700, (e.g., following accepting the fusion at step 652) the application automatically selects the contour diameter button 704 for illumination and it is in with respect to the target contour 728 that initial planning is undertaken. The user may optionally select the margin size or the focus steering buttons, described in greater detail below. Accordingly at step 804 the user ensures the contour diameter button is highlighted. At step 806 the treatment head 20, with the imaging probe 22 viewing in the YZ plane (e.g., the axial plane of the patient), is moved by driving the robotic arm 14 using the space mouse 36 or freedrive feature until the target contour 728 is centered on the target tumor or lesion in the YZ plane. Note while moving the treatment head, resistance to movement experienced by the robotic arm 14 is observed and displayed at all times and movement is slowed if resistance exceeds predefined thresholds, as described further below. Once the target contour 728 is approximately centered over the tumor or lesion the Y and Z the dimensions of the default target contour 728 are adjusted using knobs 28, to change the dimensions of the target contour 728 in each of Y and Z dimensions, the adjustment of which is depicted graphically in indicators 730.

Along with ensuring that the target contour 728 is centered on the tumor or lesion, while moving the robotic arm 14 and imaging probe 22, the acoustic field lines 724 are displayed on the UI 700. During this movement, the user can use the field lines 724 as a guide to facilitate minimal intersections with blocking structures (e.g., bone or other tissues) that can negatively impact the performance of the therapy by increasing the energy needed to achieve therapy. Alternately, the field lines 724 can be used to confirm the histotripsy treatment window with knowledge of any intervening structures. In order to reduce intersection with blocking structures, the treatment arm menu 733 may be opened and motion type of the robotic arm 14 may be limited to rotation only. Then space mouse 36 is used to rotate the position of the treatment head 20, while the target contour position 728 is maintained over the tumor or lesion. Target contour position 728 may also be maintained over/adjacent anatomical landmarks as directed by the user when direct visualization may be obscured. Confirmation that the acoustic pathway is free from obstruction at step 808 can be performed simultaneously with step 806. Alternately, confirmation that the acoustic pathway is preferable including obstructions can be performed here as well. In particular, the 3-D volumetric view illustrated in at least field 716 may provide acoustic pathway information to the user.

Figure 35:
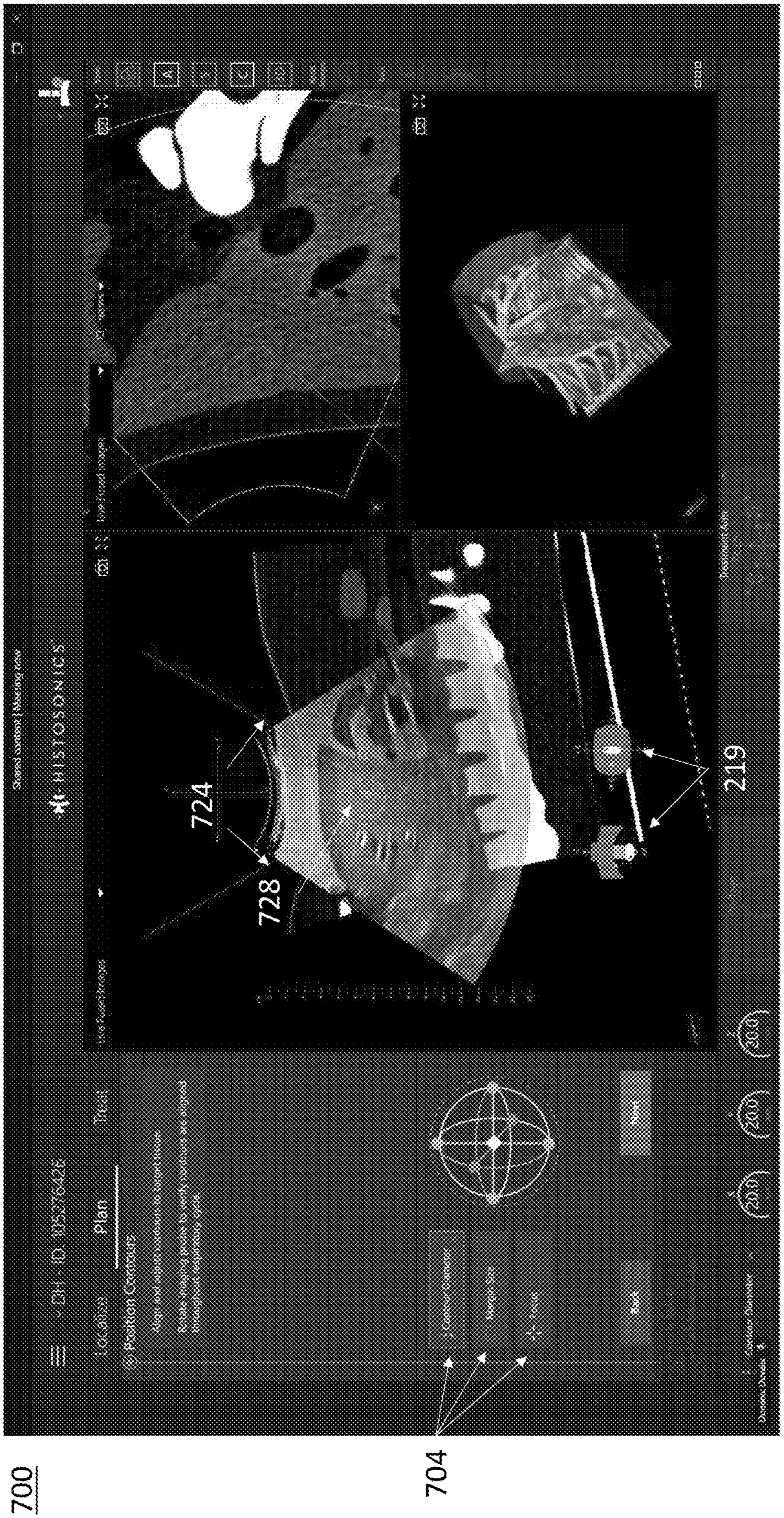

At step 810, the imaging probe 22 is rotated 90 degrees as shown with reference to position indictor 219 in FIG. 35, to view the XZ imaging plane (e.g., sagittal plane of the patient), and the treatment head 20, and particularly the imaging probe 22 are moved until the target contour 728 is centered on the target tumor or lesion in the XZ plane. In other words, target contours 728 are assessed in more than one plane. Those of skill in the art will recognize that this centering will take into account movement of the tumor or lesion through the breathing cycle of the patient, which are generally visible in the sagittal plane. The tumor or lesion is intended to remain withing the contour through movement of the breathing cycle. The X and Z dimensions of the target contour 728 are adjusted using knobs 28, to change the dimensions of the target contour 728 in the X and Z dimensions. Again, ensuring the field lines 724 are free from obstructions or field lines indicate the preferred treatment window is undertaken at step 812, which can be performed simultaneously with step 810.

Following steps 810 and 812, the imaging probe is rotated back 90 degrees to view the YZ imaging plane (e.g. axial plane of the patient) at step 813 to confirm the target contour 728 remain centered on the target tumor or lesion and the acoustic field contains the minimal amount of blocking structures. If necessary, the process is repeated from step 806 through step 812 until the contours are centered on the tumor or lesion and the acoustic field is optimized in both or more than one imaging planes.

Figure 36:

Next, using one of the knobs 28, as depicted in indicator 730 the margin size can be adjusted at step 814. As shown in FIG. 36 the margin is set at 3.4 mm, however, this value can be increased or decreased as needed to ensure a margin of sufficient volume is defined. However, the margin, which defines generally healthy tissue that will be sacrificed to ensure complete treatment is usually reduced to as small as size as appropriate so that as much healthy tissue as possible is spared from the therapy.

Figure 37:
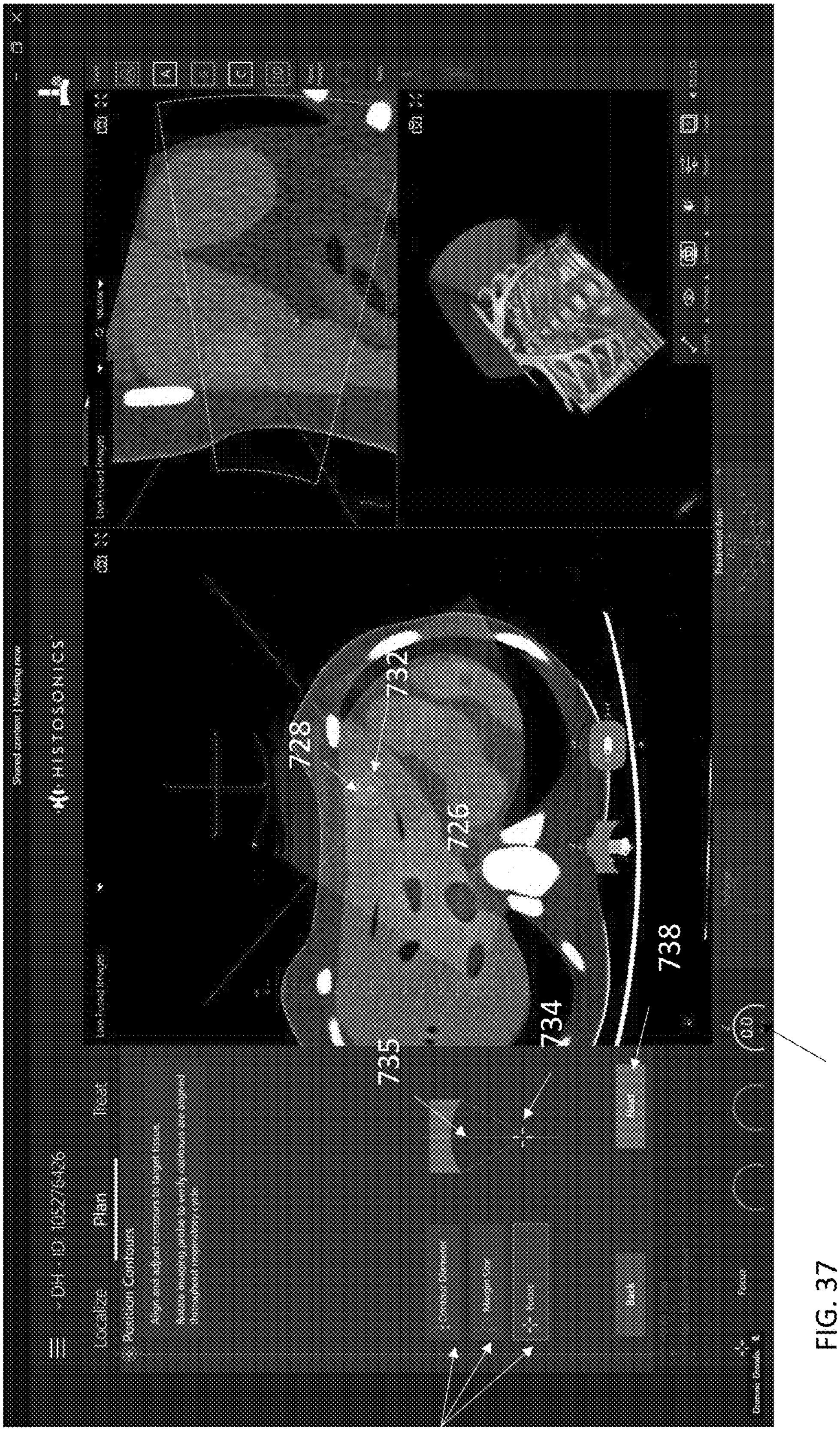

At step 816, following selection of the focus button 704 in FIG. 37, the focal point 726, depicted as crosshairs can be adjusted by moving across 734 up or down the focal axis 735 using one of the knobs 28 as and shown by indicator 730, depicted in FIG. 37. Focal steering is adjusted using one of the knobs 28, as depicted in indicator 730 at step 816 in order to reach the required depth. As shown in FIG. 34, the default focal point 726 is placed at the furthest point in the −Z direction (deepest within the body of the patient or furthest from the patient's skin) relative to the target contour 728 and the margin contour 732. Adjustment of the focal point 726 may be required if the planned treatment volume cannot encompass the distal edge of the target tumor. The planned treatment volume may not be able to encompass the distal edge of the target tumor if moving the treatment head further would impinge on the patient's abdomen. Following adjustment of the focus, steps to adjust the location and size target contour 728 and margin contour 732 may be repeated. In some embodiments, the user may opt to change treatment heads in order to obtain a different focal depth. A treatment head having more transducer elements may provide therapy deeper within the patient. In the alternative, if the targeted lesion or tumor is located in a shallow or less deep portion of the body, the user may select to down-size to a treatment head with less transducer elements to reduce energy application to the tissue.

Figure 38:

Once the user is satisfied that the target contour 728 and margin contour 732 substantially conform to the tumor or lesion over the entirety of the tumor or lesion and that the field lines 724 define a volume that is substantially free from obstructions over the entirety of the tumor or lesion (or the preferred acoustic window has been achieved including obstructions), the user may select the a next button 738 to initiate a plan verification step at step 818 and the UI 700 as shown in FIG. 38 is displayed. As the workflow advances to the plan verification, the application saves the location of the target contour 728 and the target margin 732 (i.e., the planned treatment volume) in memory, which is sometimes called 'locking' the plan to the target tumor or lesion location. Once the plan is locked, movement of the robotic arm 14 with the treatment head 20 is decoupled from the plan's location such that as the robotic arm is moved the contours displayed on the ultrasound image will be a cross-section of the planned treatment volume calculated by the application based on the current location of the robotic arm relative to the location of the saved location of the planned treatment volume. As will be appreciated, the robotic arm 14, driven by the mouse 36, adjusts the position of the ultrasound probe 22 so that a user can observe the entirety of the tumor or lesion and ensure that in the entirety of the tumor or lesion is within the target contour 728. This movement of the imaging probe 22 also helps confirm that tumor or lesion is within the target contour 728 during the respiration cycle. If at any point in moving the imaging probe 22 the tumor or lesion is outside of the target contour, the contour can be adjusted using the knobs 28.

In some examples, the user may be allowed to "lock" the contours and treatment plan in 3D space as displayed on the UI, and further allowed to robotically survey around the plan to inspect adjacent anatomical spaces/locations and/or organs and structures. This step may be used to help assess plan position for procedures using fusion wherein the ultrasound visualization of the tumor itself is challenging, but the tissue imaging is adequate. In this example, the user may use anatomical landmarks or structures in the DICOM data (e.g., MRI or CT or CBCT) to verify the tumor and plan location. In other examples, the user may simply use this feature to assess plan parameters and placement in the streaming ultrasound. In some examples, wherein sensitive organs (pancreas) and/or structures (bowel) may be close to the plan, this may enable users to assess the treatment site in greater detail and perspective. In some configurations, with the plan locked, the system may comprise return to plan or survey point features (and graphics and UI inputs) to allow the system to automatically position the plan back to the center point (and/or other plan location) per the users discretion/desire.

Once the system includes a locked plan, that locked plan may be stored or linked with a specific treatment protocol (and tumor) or a specific patient. If additional treatments are required or preferred, the locked plan may be accessible in the future such that once the patient is positioned for treatment, the histotripsy system 10 may be configured to recall the locked treatment plan such that the robot arm may be automatically driven within 3D space and the therapy transducer positioned and aligned with a center point (or an alternative identified point) within the locked plan. By aligning with a locked plan, the patient set-up including localization and specific steps of the planning steps may be omitted. In some cases, the UI may be configured to also show markings of previous user selected plan locations, including where the user has assessed the potential placement of the treatment plan, including the display of potential crosshair locations (e.g., as a plan center point), of a representative potential treatment plan. In one example, the system software may allow the user to assess multiple plan locations, wherein allowing the user to mark those locations, enabling the system software to store the position and pose of the robot, allowing the user to return to previous plan locations as desired. In another example, this functionality may be configured to allow assessing and positioning multiple treatment plans in context to one another in 3D space, including allowing the user to overlap treatment plans and/or space them apart, as defined by the user.

An interactive, representative graphic of the target contours 740 is shown on the UI 700 in FIG. 38, adjacent to the buttons 703, that allows the center point and extreme points of the plan along the X, Y, and Z axes (e.g. −X, +X, −Y, +Y, −Z, +Z) which may be called "plan or survey points" 739 to be selected. In one embodiment, this functionality may be configured to allow users to command the robot to automatically survey various points in the plan including, as an example, the plan extremes and/or center point, based on the user selected plan or survey point. In one example, at step 820, a user may select one of the survey points 739 in the target contour graphic 740 at step 820. The actual survey point locations associated with the target contour graphic 740 are defined by the target contour 728 which was generated at steps 806-812. In one aspect of the disclosure, at a minimum the −Z survey point 739 must be selected, and the move to point button 742 depressed at step 822 moving the treatment head 20 such that the focal point 726 of the therapy transducer 18 arrives at the −Z position of the target contour 728 set in the previous steps. The −Z position is the highest point (e.g., vertically from the horizontally laying patient) in the target contour 728 that will be treated by the therapy transducer 18 in subsequent aspects of the workflow. As noted on the UI in field 744, verification that the ultrasound medium is adequate (i.e., the therapy transducer 18 remains submerged and free of air bubbles) ensures that during a subsequent treatment phase, good ultrasonic coupling of the therapy transducer 18 and the patient is achieved at all times. A visual inspection of the therapy transducer 18 may confirm the therapy transducer is free or air bubbles and remains submerged. Further, in some embodiments, colored indicators on the UI may provide information about the spatial location of the treatment head. At step 824, while moving the therapy transducer 18 to a survey point 739 of the target contour graphic 740, a resistance to movement experienced by the robotic arm is observed at all times. If the resistance to movement is greater than a threshold, at step 826, an indicator may be displayed on the UI 700 (e.g., a color boundary yellow, orange, or red see FIG. 9) and the movement of the therapy transducer 18 and treatment head 20 is slowed. The resistance continues to be monitored to determine if the resistance exceeds a second threshold at step 828. If the resistance exceeds the second threshold the movement of the robotic arm 14 and the treatment head 20 may be slowed, paused and/or stopped at step 830 and mitigation measures may be displayed at step 832. Further, the UI may display the origin and/or interaction causing the force feedback (e.g., location on treatment head interacting with the patient and/or coupling frame, etc.). As will be appreciated, more thresholds may be employed without departing from the scope of the disclosure. For example, a first threshold may result in a reduction of speed to 50% normal driving speed, a second to 25% or normal driving speed, and a third threshold stopping of the drive of the robotic arm 14. If, however, at step 828 the resistance remains below the second threshold, and the user has not terminated the movement of the treatment head 20, the method continues to step 834 where a determination is made whether the survey point 739 has been reached. If not, the method returns to step 826 for continued slowed movement, however, if the survey point 739 has been reached, the method proceeds to step 836, which may also be arrived at if during step 822 the resistance to movement never exceeds the first threshold. At step 836 an inquiry is made whether additional survey points 739 need to be driven to. If yes, the method returns to step 820, however, if sufficient or all of the survey points have been driven to then the user may select the next button 746.

At any point during plan verification, (e.g., following display of mitigation measures) a user may select one of the buttons 704 and adjust the target contour 728, the margin contour 732 or the focus 726 at step 833 (as those features were described above) and then re-enter plan verification, as described above, without navigating away from the UI 700 depicted in FIG. 38. The user may feel the need to adjust the plan based, for example, observing that a portion of the tumor or lesion is not within the treatment volume or because the resistance to movement experienced by the treatment head 20 is too great for their procedure. As disclosed previously, these steps may comprise using and/or returning to a previously saved position/pose to assess alternative approaches.

In addition, as shown in FIG. 38 as plan location button 736 is now available. When plan location button 736 is selected, the knobs 28 may be used to adjust the plan location in the X, Y, and Z axes and the contour position is immediately updated accordingly on the ultrasound image in the form of one or more image overlays. This is an alternative to using the back button to return to step 804 and begin adjusting the plan location. In the case the user would like to change the angle or position of the treatment head to further optimize the acoustic field, they must select the back button and return to step 804. In some embodiments, the system software may allow the user to lock on a target location, and survey around the selected point to assess the most optimal or user preferred acoustic window to the user selected target. In some examples, this may allow users to assess tradeoff decisions where an approach may include bowel and rib obstruction, and to select a preferred approach around and/or through these structures. In some representative examples wherein a user may be able to use this feature to avoid bowel but still treat through one or more ribs. In another example, this feature may also be used to assess potential physical collisions with the patient and/or coupling set up, in addition to assessing the acoustic pathway.

As can be expected, moving the treatment head 20 such that the focal point 726 is at the +Z survey point 739 is likely to meet the most resistance, thus in accordance with one aspect of the disclosure at least the +Z and −Z survey points are driven to using steps 820-836. In another aspect all of the survey points 739 are driven to ensure that during a treatment phase, resistance exceeding the second threshold is never experienced. Further, other protocols for limiting motion when breaching one or more thresholds may be employed as described elsewhere herein.

Figure 39:
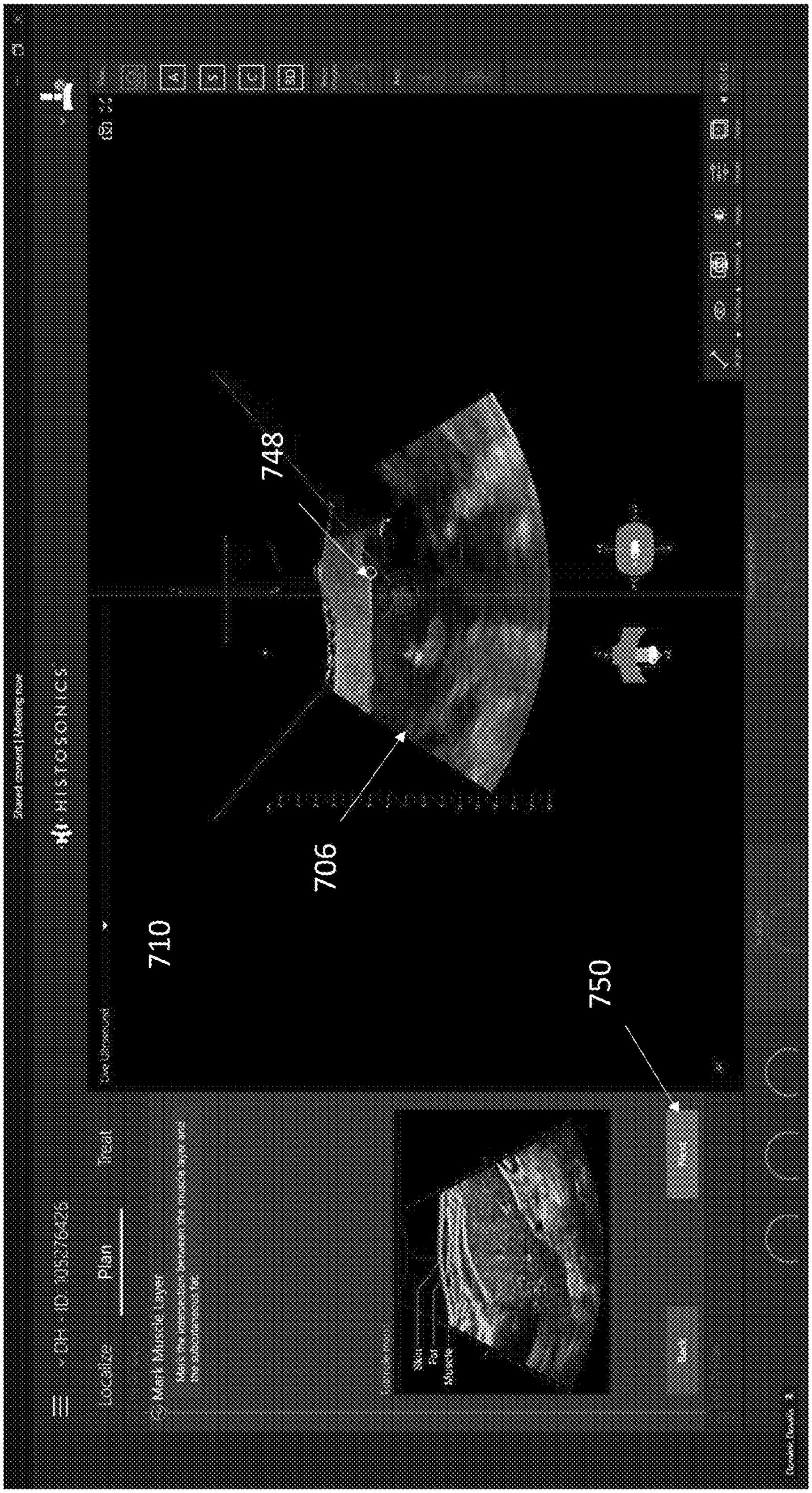

Following selection of the next button 746, the UI 700 depicts the image of FIG. 39. As shown in FIG. 39, at step 838 the user is asked to place a marker 748 in the ultrasound image 706 displayed in field 710 at the intersection between the body and another location, in this case the muscle layer and the subcutaneous fat layer of the patient and/or the plan location. Following placement of the marker 748 the user may select the next button 750 and the UI 700 displays the image of FIG. 40. At step 840 the target contour 728 margin 732 are confirmed as aligned with the tumor or lesion throughout the breathing cycle, and in multiple planes by rotation of the imaging probe 22 to display live ultrasound with the target contour 728, the margin 732, and the field lines and the position of the tumor or lesion observed relative to these plans and planes (e.g., axial and sagittal, etc.), to ensure the lesion is positioned in context to the contours per user preference and treatment intent. In one example, this includes ensuring the tumor and/or targeted tissue is fully enveloped in the contours to ensure complete tumor/tissue destruction. In a different example, a user may desire the treatment plan to partially treat the tumor/targeted tissue, including potentially and intentionally leaving remaining tumor and/or non-tumor tissue adjacent to the treatment. The work-flow may continue to include the treatment head 20 to be driven to the −Z point in the plan to again confirm the coupling medium level within the coupling assembly 46 is sufficient such that at the −Z position the treatment head remains sufficiently submerged in the coupling medium. Once the treatment head 20 has reached the −Z point the accept button 754 becomes available. Optionally the treatment head 20 may again be driven to any of the other survey or plan points 739 by selection of the survey point 739 and the move to target button 742. For example, this may serve to both ensure no force or resistance issues will be encountered in terms of physical collisions or interactions with the patient or coupling assembly (e.g., verifying that the focal point 726 can be maneuvered to the +Z position). The step of placing a marker at the intersection between the muscle layer and the subcutaneous fat layer of the patient may be repeated if, for example, the treatment head 20 changes position.

If at any point the target contour 728 or margin 732 are found not to align with the tumor or lesion through the breathing cycle, as observed on the real-time ultrasound and/or using other imaging data, the adjust plan button 752 may be selected and the method return to step 804 where the target contour 728 is redefined. However, if the plan is verified at steps 840 and 842, the accept plan button 754 may be selected to move to treatment.

Resistance Detection

At various points during the localization, planning, or treatment phases of a procedure, the robotic arm 14 and the treatment head 20 may encounter resistance to motion and/or increased force feedback. Due to said resistance, forces and potential collisions, the system may be configured to store/record the pose and position of the robotic arm and treatment plan and/or target location, to allow users to locate and/or return to the respective pose, positions and locations should the system encounter resistance and/or force requiring the treatment head to be positioned away from the patient. Further, part this resistance to motion, at least generally in the −Z direction, is the buoyancy of the treatment head 20, which may be accounted for and/or continuously calculated and removed from the resistance measurement, as described in of method 400. During motion and movement of the robotic arm 14 and the treatment head 20, the Histotripsy system 10 monitors the resistance (forces acting on the treatment head opposite the direction of motion) caused by physical interactions of the treatment head and the coupling assembly 46 or the patient. As the treatment head 20 is moved to each survey point, or otherwise moved about the patient, understanding resistance and force interactions ensure the therapy transducer 18 can deliver Histotripsy to all portion of the target contour 728 and the margin 732 without injury or damage the equipment or patient. Further, as noted elsewhere pressure applied to the patient, via the treatment head 20 can also cause the soft tissues of the patient to potentially move, shift or distort/deform. This distortion and/or deformation, may be problematic when utilizing the fusion application (described above) or the 3D fusion models 718 resulting in a potential induced image-to-body divergence. Thus, in creating the 3D fusion model, and subsequent treatment plan, the force or pressure applied to the patient by the by the treatment head 20 must be kept at and/or below a defined threshold to ensure that target contour 728 and margin 732 accurately reflect the tumor or lesion to be treated and that the areas of the patient to receive therapy are not distorted which can result in incomplete therapy, or application of therapy to tissues outside target contour 728 or margin 732. In some system embodiments, the fusion model may include various additional sensor inputs to allow tracking movement, distortion and/or deformation, and further enable a dynamic deformable registration model updated to account for such issues.

In accordance with the disclosure, indicators of the magnitude of pressure or force being applied to (or applied against) the patient or resistance to movement of the treatment head 20, may be displayed on the UI as resistance indicator 222 (See e.g., UI 200 in FIGS. 9 and 10). As shown, the UI 200 is surrounded by a different colored border or resistance indicator 222. The color of that resistance indicator, e.g., yellow for low resistance, orange for medium resistance and red for resistance in excess of a threshold, can change as the robotic arm 14 and the treatment head 20 are moved above and/or around the patient. Thus, the resistance indicator is an indicator of the magnitude of the force the robotic arm 14 must apply to drive the treatment head 20 to a location on the patient to overcome the resistance to that motion of the treatment head imparted by the patient's body. In some aspects of the disclosure, based on pre-defined thresholds or limits, the histotripsy system 10 may enable or disable certain aspects of both the treatment head positioning interface controls (e.g., use of freedrive buttons 44) of the robotic arm and/or the system user interface console, including but not limited to the space mouse 36. Further the Histotripsy system 10 may have specifically designed responses and actions upon reaching the respective resistance or force thresholds/limits. This may include have similar or distinct behaviors based on the origin of the forces (e.g., telescoped treatment head imaging probe versus a coupling collision, etc.). Though above with respect to method 800 only two such responses were described, specifically slowing the drive of the robotic arm 14 and treatment head 20 or stopping the drive, these responses are not so limited and may include slowing, pausing, reversing, movement of the robotic arm 14 and treatment head 20, or may be configured not to modify any Histotripsy system-directed automated motion or movement of the robotic arm (e.g., automated movement to plan points, etc.).

In one example, a system is configured such that when detected resistance detected is low, automated movements of the robotic arm 14 and the treatment head 20 are not limited, but user directed movements using the freedrive buttons 44 or space mouse 36 may have their speed reduced in the direction of the resistance. When a medium resistance is detected, the manual movement speed may be further reduced in the direction of the resistance and automated movements are again not slowed. When a resistance limit is reached, manual movement in the direction of the resistance is prevented and automated movements are allowed to continue unless a threshold (e.g., 50-newtons of resistance)

is reached at which point a soft emergency stop is initiated and an appropriate corrective action message is displayed on the UI. These limits to movement apply during the entire procedure and take into account pressure applied to the treatment head 20 caused by respiration of the patient and well as the buoyancy of the treatment head 20. In this manner, with the buoyancy accounted for and effectively negated, a true value of the force being applied to the treatment head 20 or the resistance caused by the patient's anatomy can be assessed and acted on accordingly.

Treatment

Once in treatment phase of the work-flow, systems may be configured with several features and steps to enable a bubble cloud detection, visualization, calibration (locating bubble cloud in 2D or 3D space in the imaging to account for any focal shift), aberration correction and threshold determination and setting. These features and steps may be implemented in various ways in effort to best enable usability and user experience. In some examples and configurations, the system may guide the user through various steps to initiate therapy to determine one or more of the listed features (e.g., locate the cloud for calibration, etc.). In other configurations, the system may automate the steps and require the user to verify/acknowledge the steps (values established by the system). In addition, various UI graphics or overlays may be used to display these features, as well as associated user-guided text to support the various steps.

Figure 40:
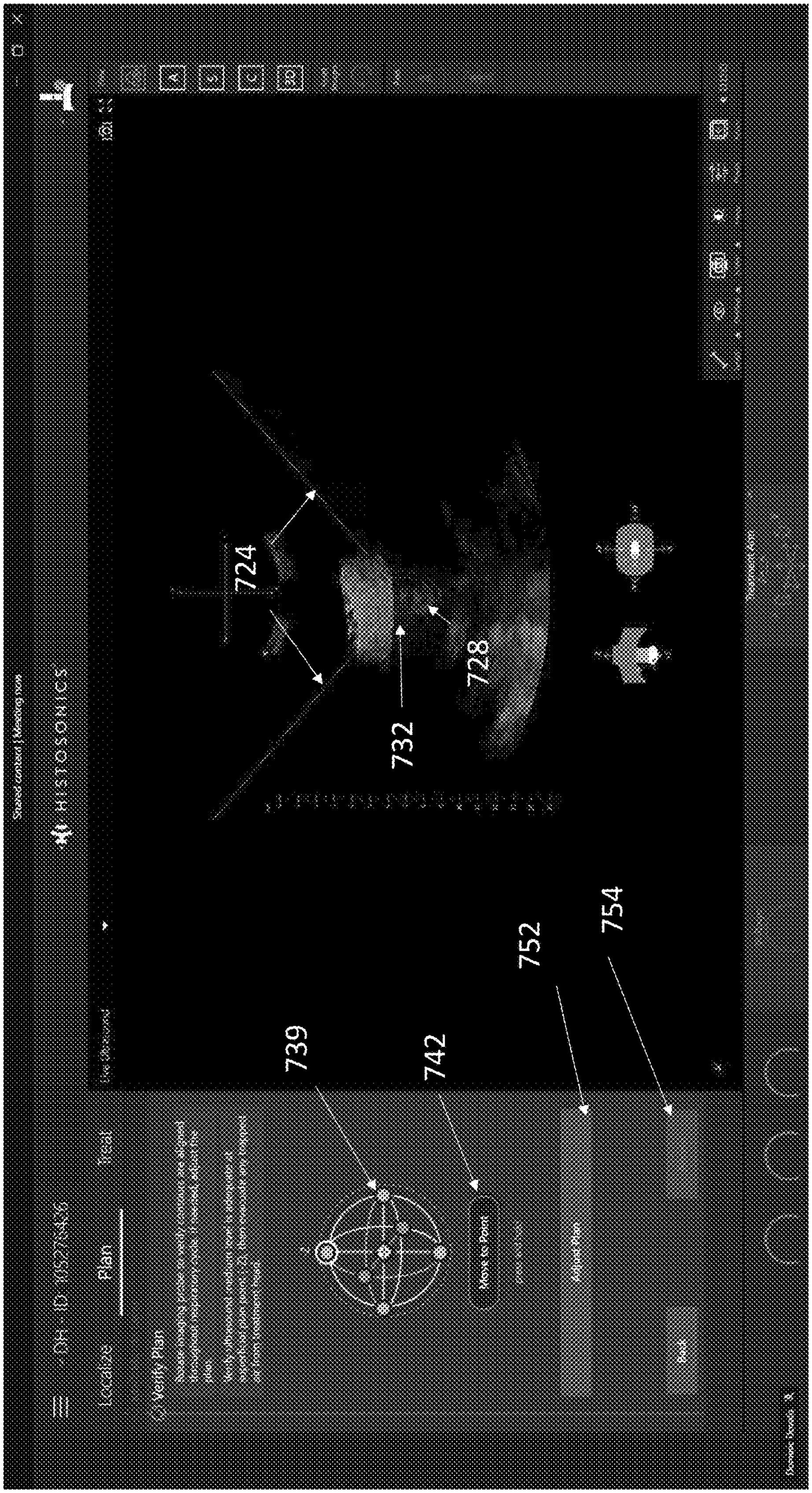
Figure 41:
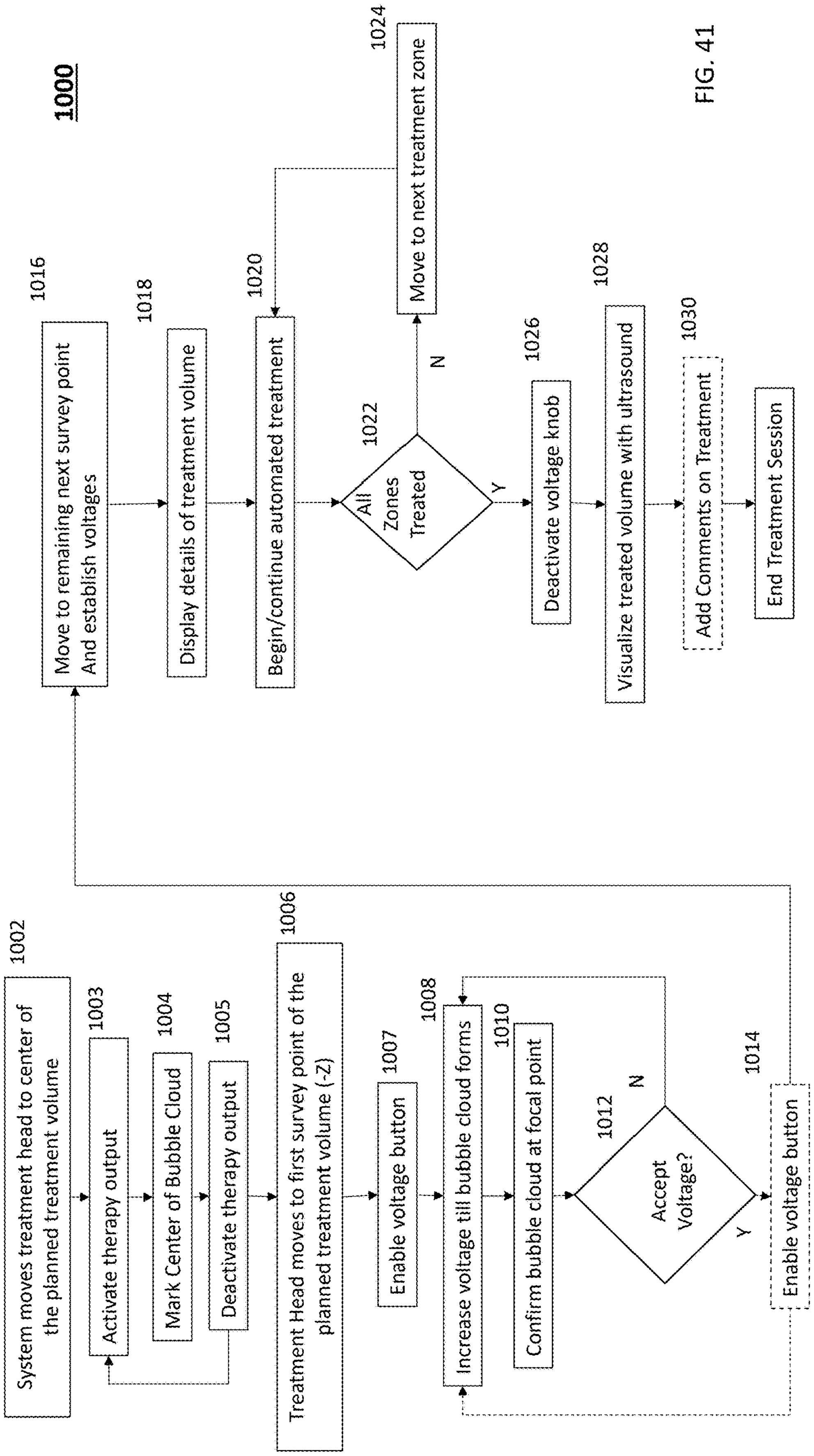
FIG. 41 depicts a flowchart outlining a method of performing a histotripsy therapy procedure in accordance with the disclosure.
Figure 42A:
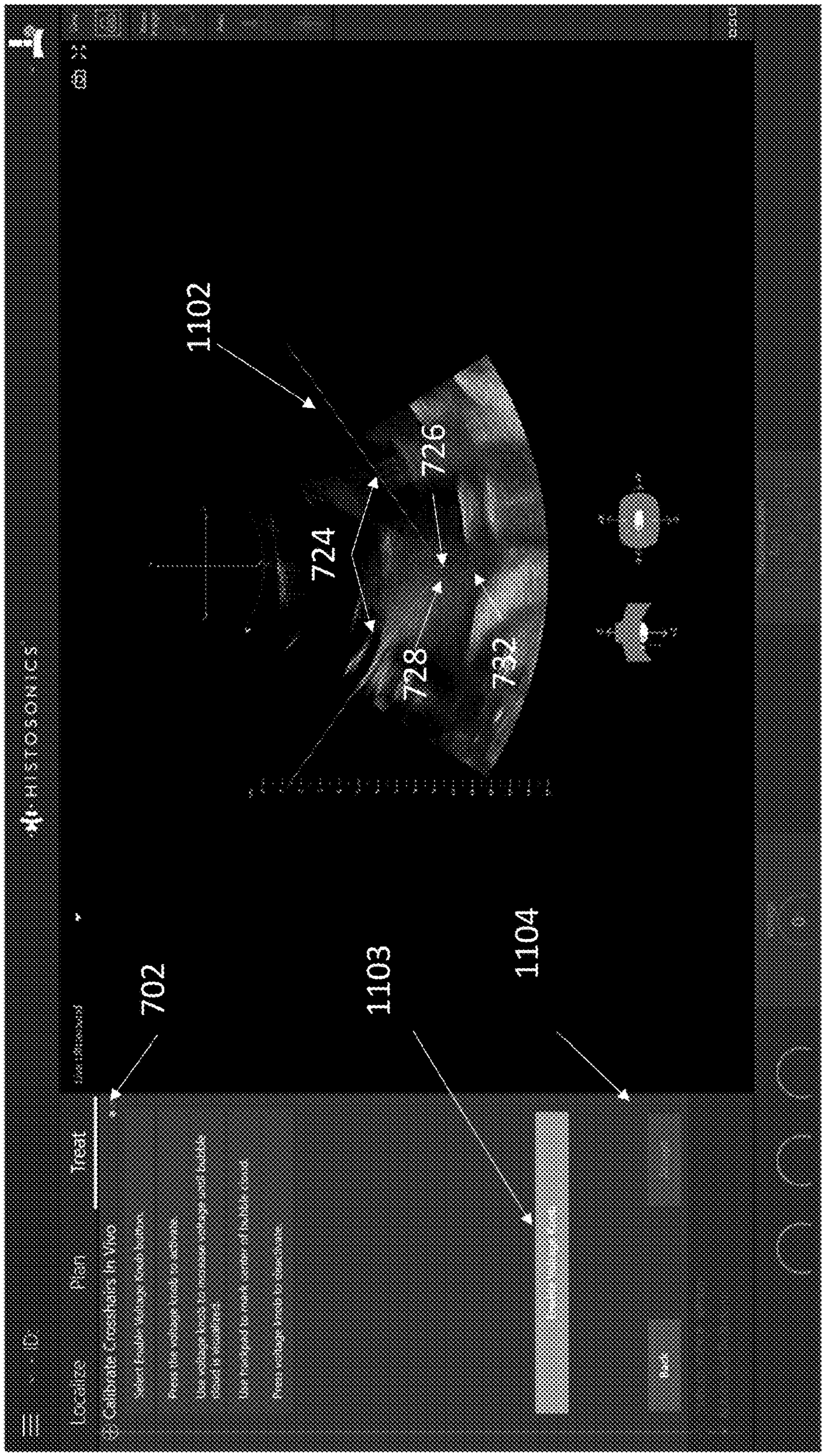
FIGS. 42A-50 depict a series of user-interface images following the steps of the flowchart of FIG. 41 in accordance with the disclosure.
Figure 42B:
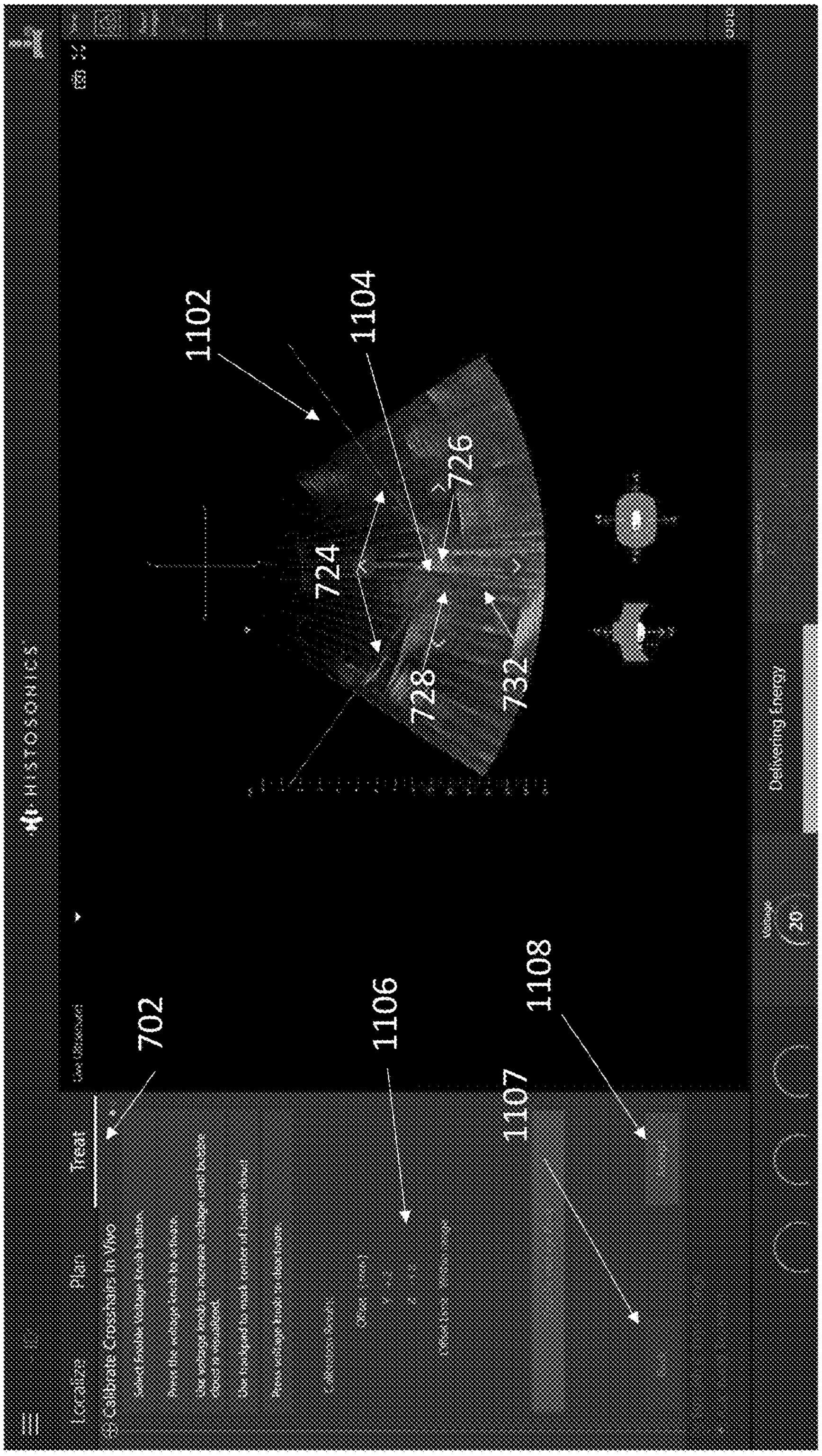

In one system configuration, once the target contour 728 and margin 732 have been established and it has been verified that the coupling medium is sufficient and the treatment head 20 may be driven to each of survey points 739 without exceeding the threshold resistance or force values and following selection of the accept button 754 in UI 700 of FIG. 40, the patient may be treated. FIG. 42A depicts a UI 1100 employed to treat a patient with an ultrasound image 1102 displayed and overlayed with the treatment contour 728, the margin 732, the field lines 724, and the focal point 726. The UI 1100 shows the indicators 702 have the "Treat" indicator illuminated. To conduct a therapy method 1000, and before engaging in application of continued therapy via the therapy transducer 18, the location of the bubble cloud in the patient (in vivo) must be calibrated and the voltage settings for driving the therapy transducer 18 must be set.

The method 1000 starts with an in vivo calibration process, intended to align the focal point indicator 726 to the location of the therapy focus, where the bubble cloud occurs. Note this in vivo calibration step is required in addition to the calibration described in method 100 because of the inherent variation in intervening tissues between treatment head 20 and the tumor which may slightly deflect the focus in different ways. The calibration in method 1000 ensures that the bubble cloud will initially occur near the focal point 726, however the final offset must be uniquely determined for each patient or tumor location by calibrating cloud location to the center of the planned treatment volume. To start, the system automatically moves the treatment head 20 such that the focal point 726 is at the center of the planned treatment volume at step 1002 as shown in FIG. 42A. As depicted in FIG. 42A, instructions are provided to enable voltage knob 32 at step 1003 by selecting button 1103, and then depressing the voltage knob 32. Then therapy output is increased until a bubble cloud 1104 (FIG. 42B) is visualized and/or audible signal heard by turning the voltage knob 32. If the bubble cloud is visualized to offset from the focal point 726, the trackpad 34 is used to mark the actual location of the center of the bubble cloud at step 1004 with the crosshairs 726. This visualization may be accompanied by the user detecting an audible signal in a given range which is indicative of formation of a bubble cloud. Then the voltage knob 32 may be depressed again to deactivate therapy output at step 1005. Once the bubble cloud location is marked (e.g., with crosshairs 726), the values of the distance the indicator is offset from the center of the planned treatment volume are displayed in field 1106 and the robotic arm 14 automatically and mechanically moves the displayed distances such that the bubble cloud occurs at the center of the planned treatment volume. In the case of large offsets in the Z-axis, a notification may be displayed to warn the user of potential impact to the acceptability of coupling medium level and resistance thresholds. If the user is concerned that the calibration offset may jeopardize the acceptability of these items, they may use the back button 1107 to return to step 840 of method 800, and from there to make adjustments as necessary to the planned treatment volume. Optionally, as referenced herein, the system may direct the user to again to mark the intersection between the muscle layer and the subcutaneous fat layer of the patient. Once therapy output has been deactivated, the accept button 1108 may be selected. Alternatively, the method 1000 may return to step 1003 with the reactivation of the voltage knob 32 and a renewed attempt to mark the center of the bubble cloud or verify the cloud appears at the center of the planned treatment volume.

Figure 42C:
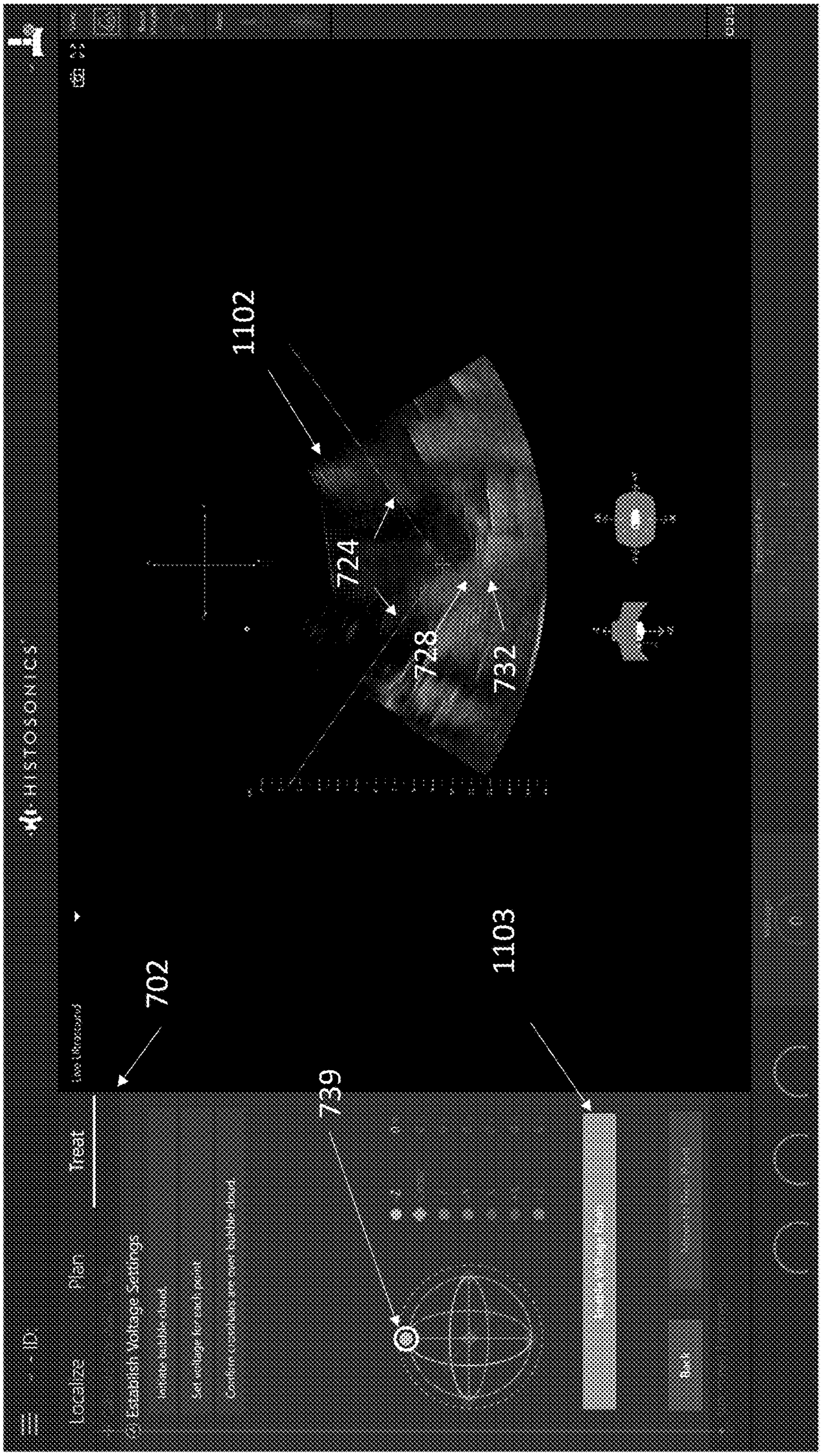
Figure 43A:
Figure 43B:
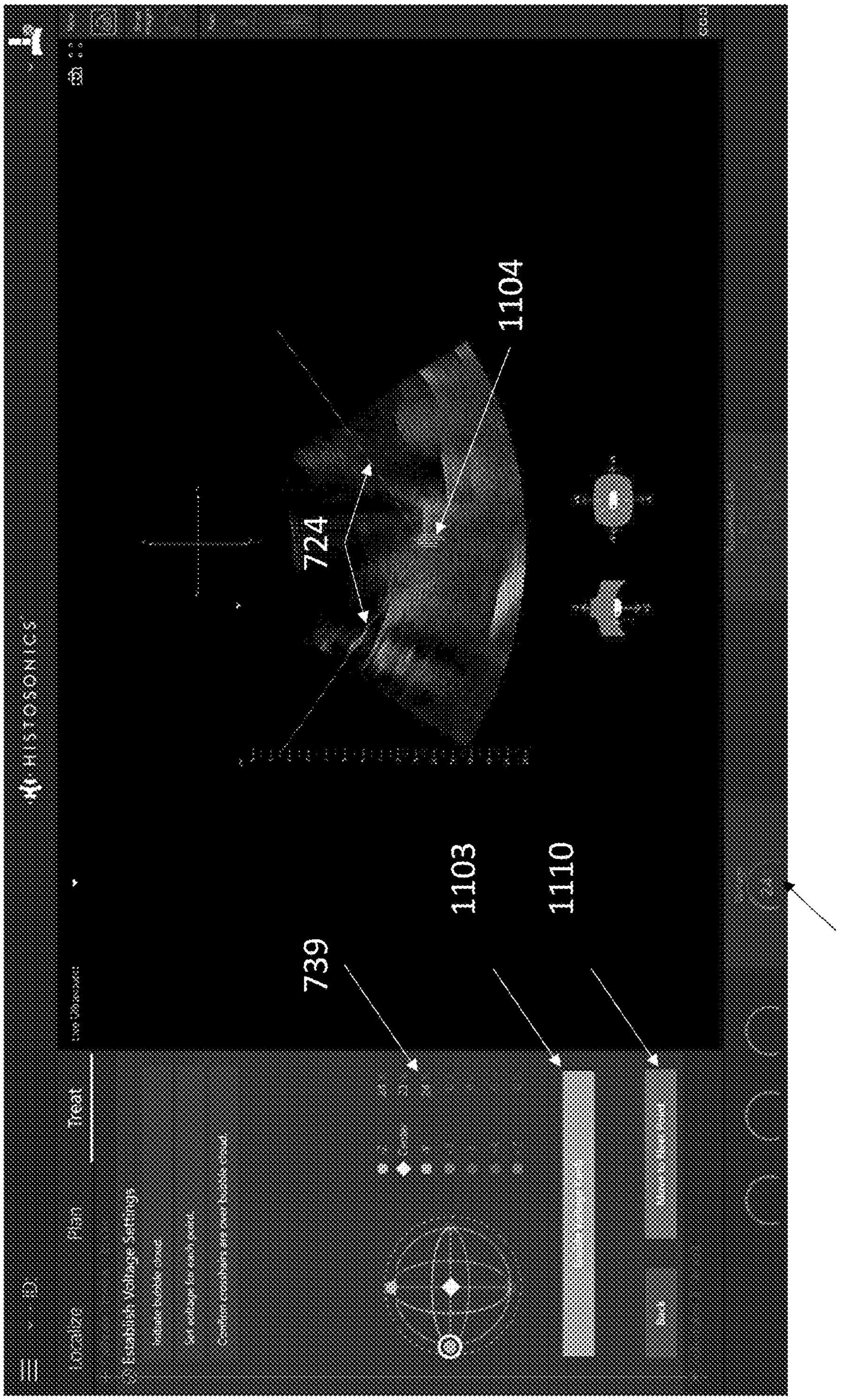

After in vivo calibration, the voltage settings necessary to generate a bubble cloud at each survey point is evaluated in an order set by the application. As shown in FIG. 42C the first of the survey points 739 (here the −Z survey point) is specified by the application and the robotic arm 14 navigates the treatment head 20 at step 1006 to position the therapy focal point at the specified survey point where, based on having completed the in vivo calibration it is believed that the focal point 726 of the therapy transducer 18 will align with the location relative to the treatment contour 728 or the margin 732, depending on settings, that is represented by the selected survey point 739. At step 1007, the enable voltage button 1103 is selected. At step 1008 voltage knob 32 is engaged and the drive voltage for the therapy transducer 18 as depicted in indicator 1109 is increased until a bubble cloud 1104 forms in the ultrasound image 1102. At step 1010 the user visually (or audibly) confirms that the center of the bubble cloud appears at the focal point 726 (depicted as crosshairs) at the intersection of the field lines 724 as shown in FIG. 43A, where the treatment head 20 has already been navigated to the −Z and survey point 739 and is now at the center survey point 739. For each survey point 739 the voltage percentage, which is increased by rotating the voltage knob 32, to achieve a bubble cloud 1104, as depicted in the voltage indicator 1109, is recorded. This process continues through all the survey points 739. FIG. 43B shows the recorded voltage percentage required to achieve a suitable bubble cloud at the +Y survey point. In one aspect of the disclosure the last position to which the robotic arm 14 and treatment head 20 are navigated is the +Z position, however, any position may be selected without departing from the scope of the disclosure. Alternatively, the application may have a specific order in which the positions are navigated to and through which complete interrogation of the treatment volume is undertaken prior to therapy starting.

Figure 44:
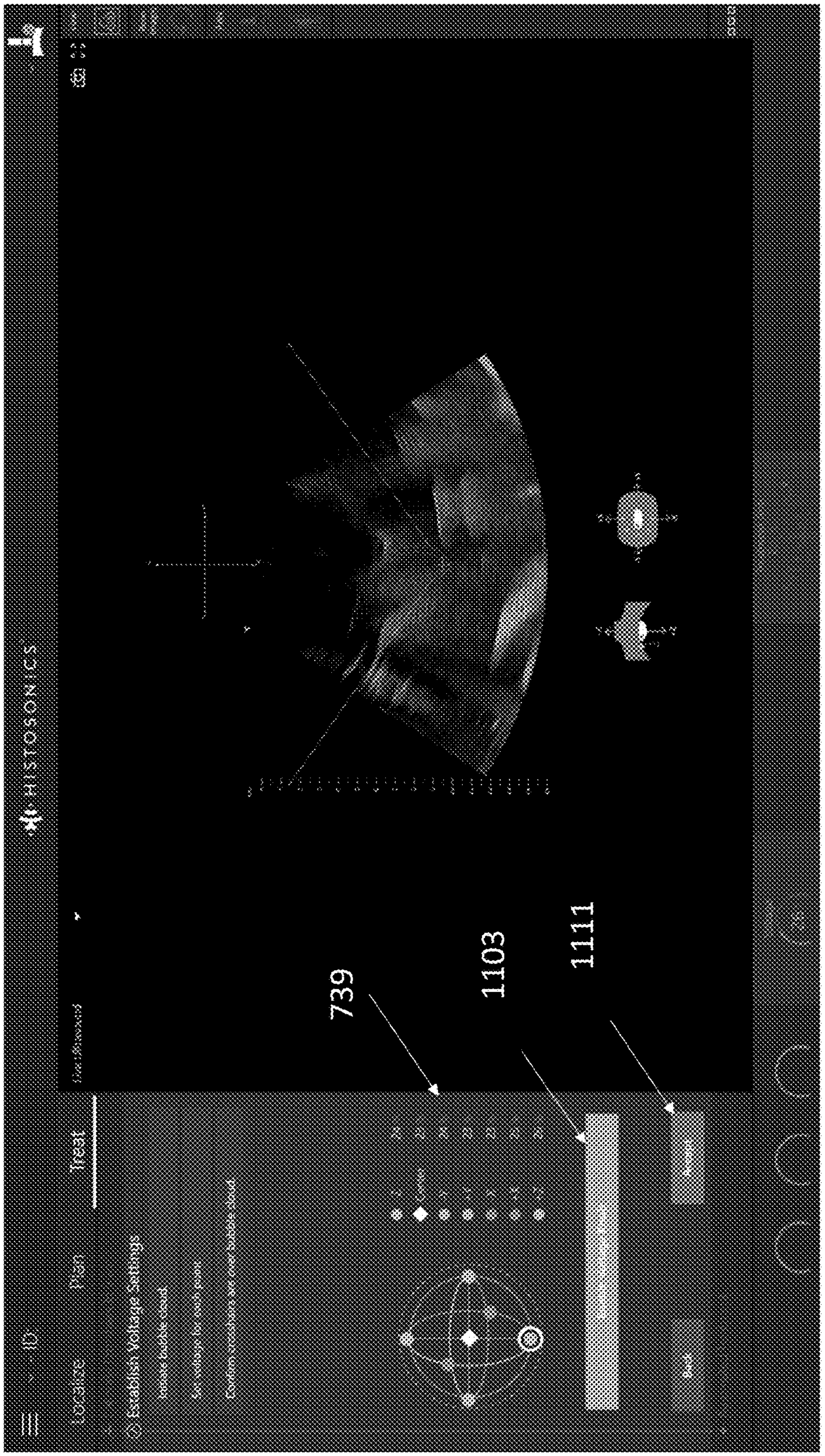

Once a voltage on the indicator 1109 has been increased by rotating the voltage knob 32 such that an acceptable bubble cloud 1104 has been generated at step 1010, which may be accompanied by recognizing a distinct audible tone, generated by the therapy transducer 18 and there has been visual confirmation at step 1012 that the bubble cloud 1104 is centered on the focal point 726 and that the voltage is acceptable at step 1013, the move to next button 1110 may be selected at step 1016. If the user is unsure of the voltage selected, the enable voltage button 1103 may again be selected at optional step 1014 and the voltage changed. This process is repeated until all of the survey points 739 including a center point are navigated to and a voltage applied to the tissue until an acceptable bubble cloud 1104 is generated and the voltages recorded as shown in FIG. 44. In one embodiment, 7 survey points 739 are included, which may be +Z, −Z, +Y, −Y, +X, −X and the centerpoint of the treatment volume. These 7 survey points represent outermost boundaries or extremes for the treatment volume, which is illustrated as a sphere. If the treatment volume comprises other geometric shapes, it should be understood that a set or specified number or survey points as test pulses may be required which include the outermost extremes of the treatment volume. The voltages for each survey point 739 and the center point are stored in memory. These recorded voltage values are used to interpolate a voltage value to be used at each survey point in the treatment volume, as described above. As will be described in greater detail below, the treatment volume is comprised of a plurality of individual treatment zones, each one of which neighbors one or more treatment zones. By interpolating the needed voltages for formation of a bubble cloud 1004, adequate voltage can be applied at all points within the volume without requiring testing of the formation of a bubble cloud 1104 for each treatment zone. This system process is also referred to hereinabove as threshold testing.

Figure 45:
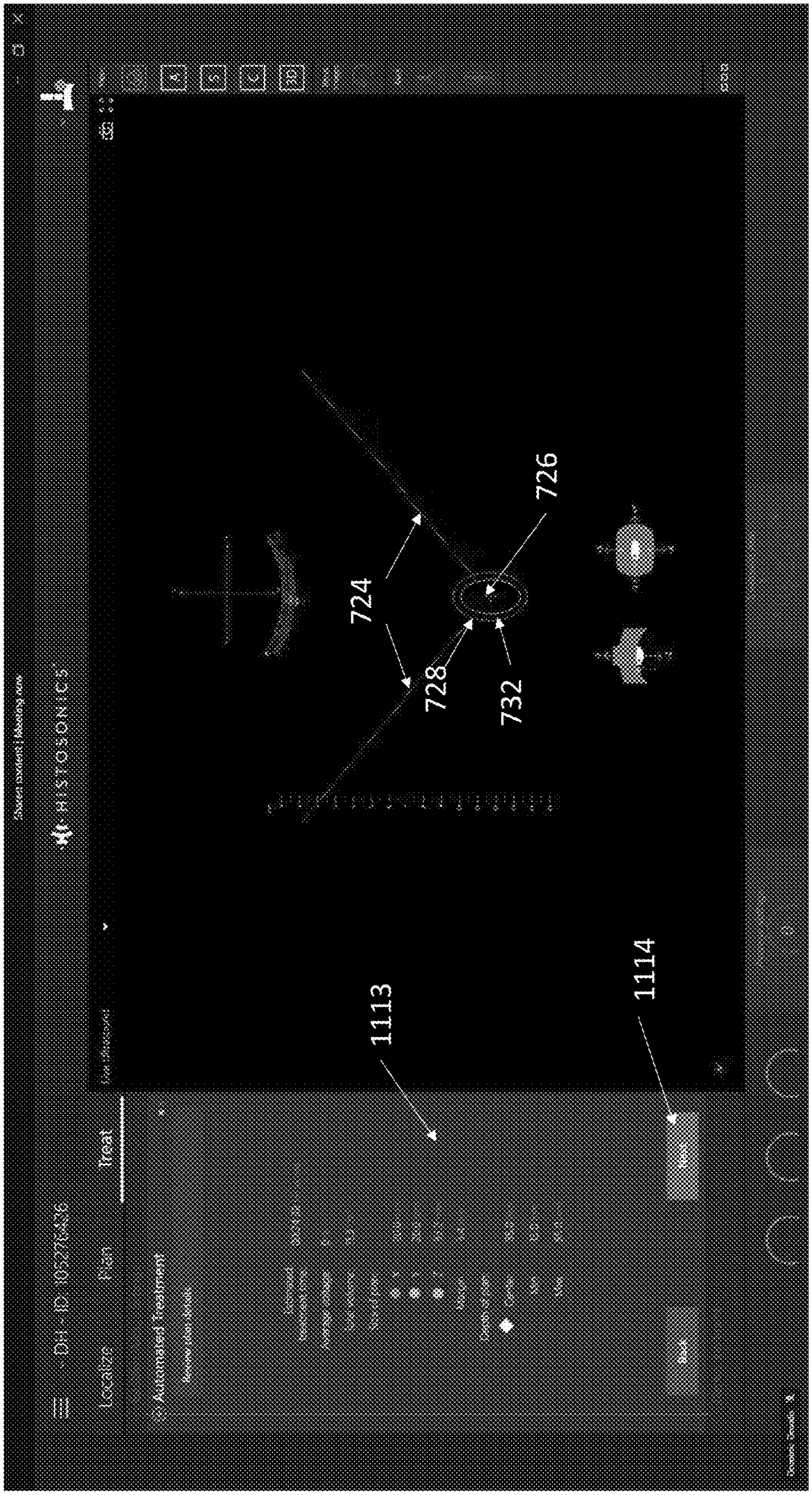
Figure 46:

Once all of the survey points 739 and the center of the volume defined by the survey points 739 have been navigated to and a voltage recorded for each location, the accept button 1111 becomes available and when selected the UI 1100 updates to that shown in FIG. 45 where details of the treatment volume 1113 are outlined. These include the dimensions along each axis, the total volume, a minimum depth of plan, a maximum depth of plan, and a center point depth of plan. Further, an estimated treatment time for the treatment volume is also provided/displayed to the user. The estimated treatment time is calculated by the histotripsy system based on parameters including but not limited to treatment volume, voltage, cooling time(s), focal location overlap. After review, a next button 1114 is selected at step 1020 and treatment begins. As shown in FIG. 46, the ultrasound images 1102 may be replaced by a live fused image 1115 (e.g., live ultrasound fused with pre- or peri-procedural images), if fusion has been employed and desired by the user. If not, then treatment proceeds on just the live ultrasound images. Treatment begins at the +Z survey point, which is deepest within the patient. The panel 1116 includes a volumetric progress indicator 1118. The volumetric progress indicator 1118 shows the entire volume to be treated 1120 (e.g., a volume defined by the margin 732) as well as the individual treatment zones/focal locations 1122.

Each focal location is a volume of tissue which receives histotripsy pulses from the therapy transducer 18 for a given duration. The energy or histotripsy pulses from the therapy transducer 18 causes the cells to burst due to cavitation of the tissue when the focal point is at the focal location 1122 which is evidenced by the bubble cloud 1108, rendering the cells acellular debris that will be reabsorbed by the body. By monitoring the amount of energy directed at a given focal location 1122, and by cycling the energy application on and off at specific durations (as described herein above), a non-thermal ablation of the volume to be treated 1120 is achieved. As will be appreciated, the focal locations 11122 may have some overlap in volume to ensure that complete treatment of the tissue.

At step 1022 an inquiry is made whether all focal locations have received treatment, if not the method progresses to step 1024, where the robotic arm 14 and therapy transducer 18 advance in a stepwise fashion, and in the example provided here a spiral form starting the +Z survey point 739 advancing to each successive focal location 1122. As noted above a variety of different treatment patterns may be employed without departing from the scope of the disclosure. In this way steps 1020 through 1024 are repeated until all focal locations 1122 have received treatment, resulting in the entire volume to be treated 1120 having received treatment. The movement of the robotic arm 14 and therapy transducer 18 is controlled by an application stored on the computing device such that for each successive focal location 1122 the therapy transducer 18 is positioned at a location on the patient where-by the focal point 726 is centered in the focal location 1122 and the bubble cloud 1104 will be generated for that specific focal location 1122. The duration of the application of energy, and period of no energy application before movement to the next focal location 1122 are also controlled by the application, as described herein above.

Figure 47:
Figure 48:
Figure 49A:
Figure 49B:
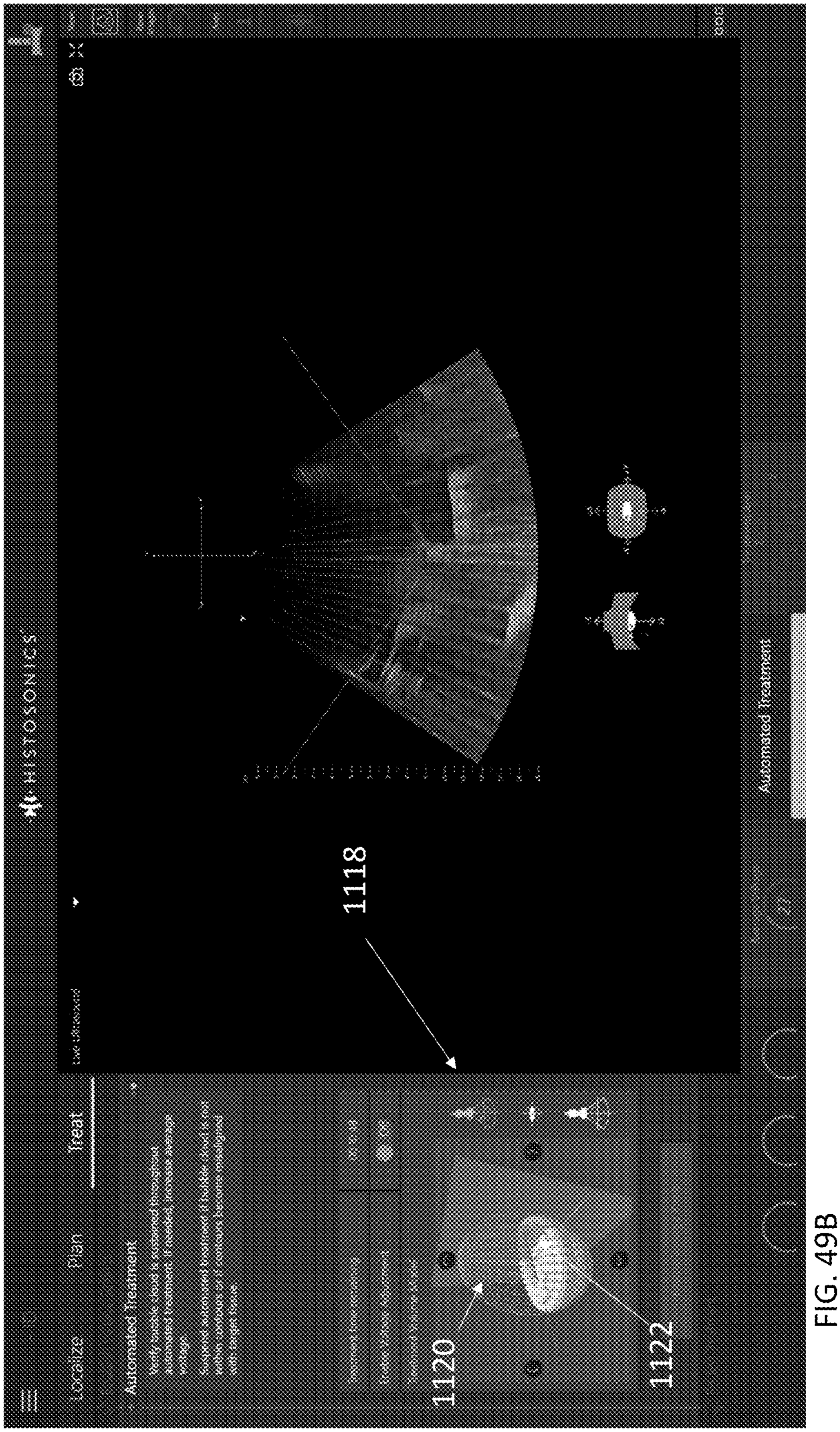
Figure 49C:
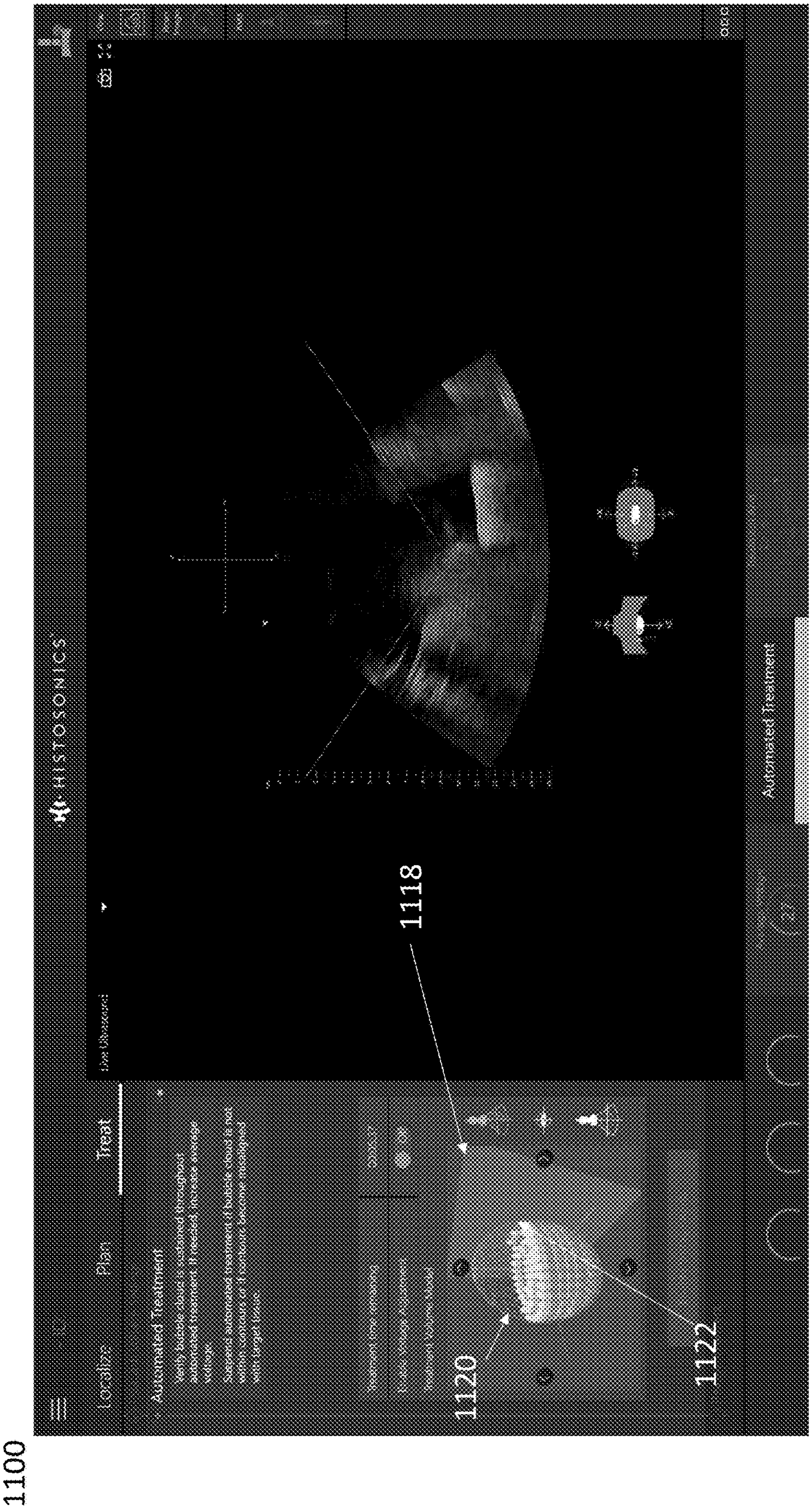
Figure 49D:
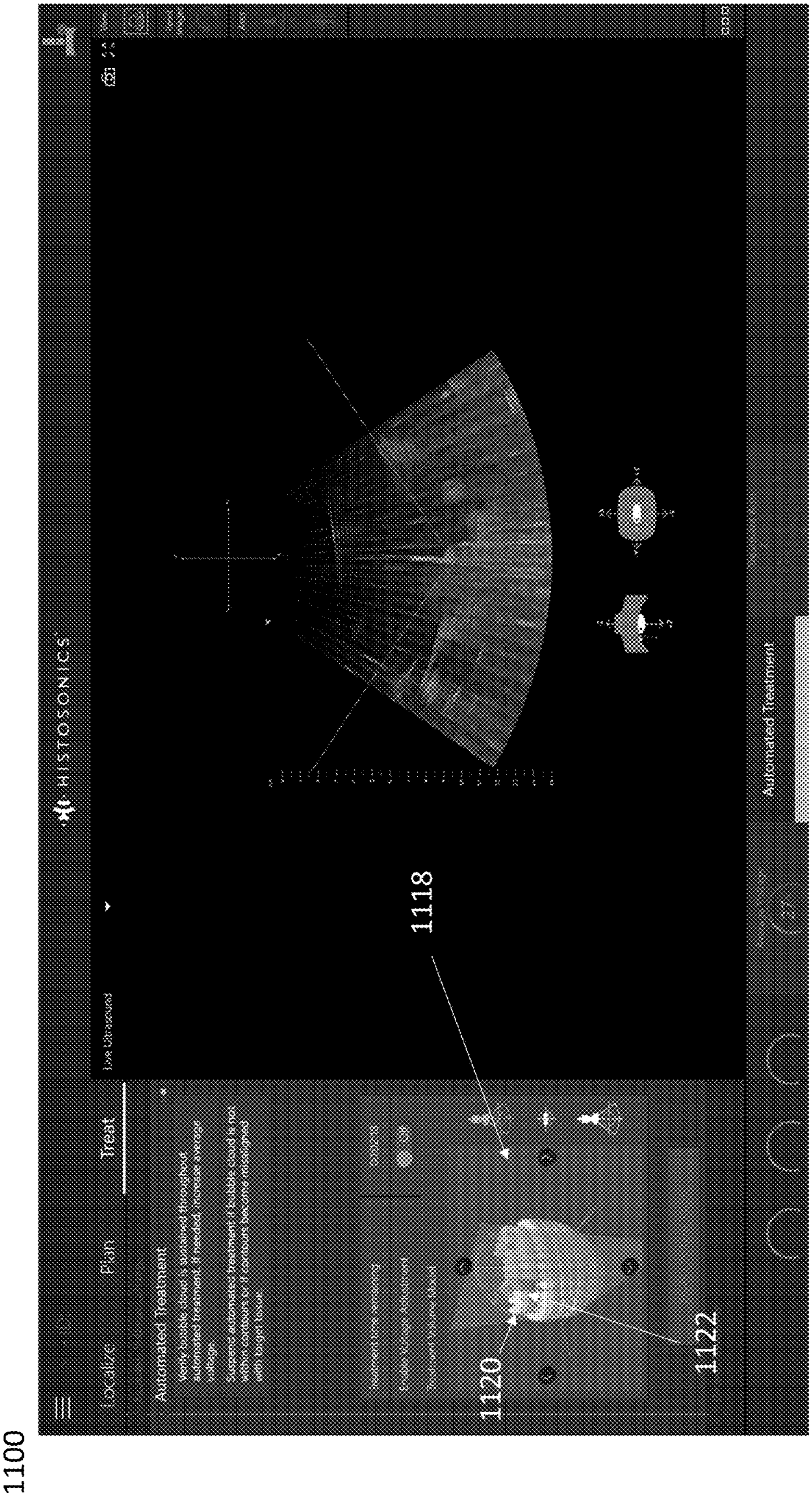
Figure 49E:
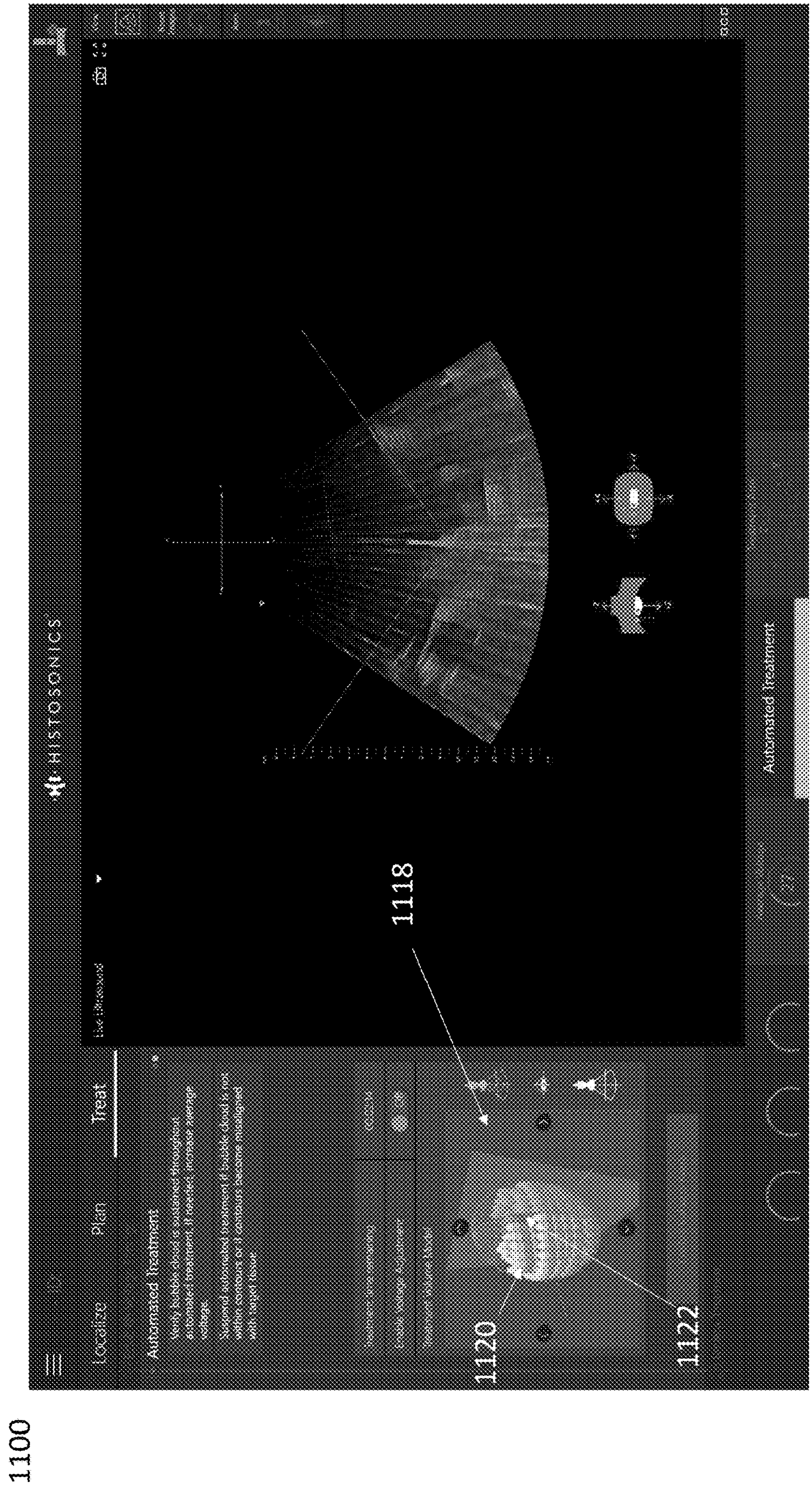
Figure 49F:
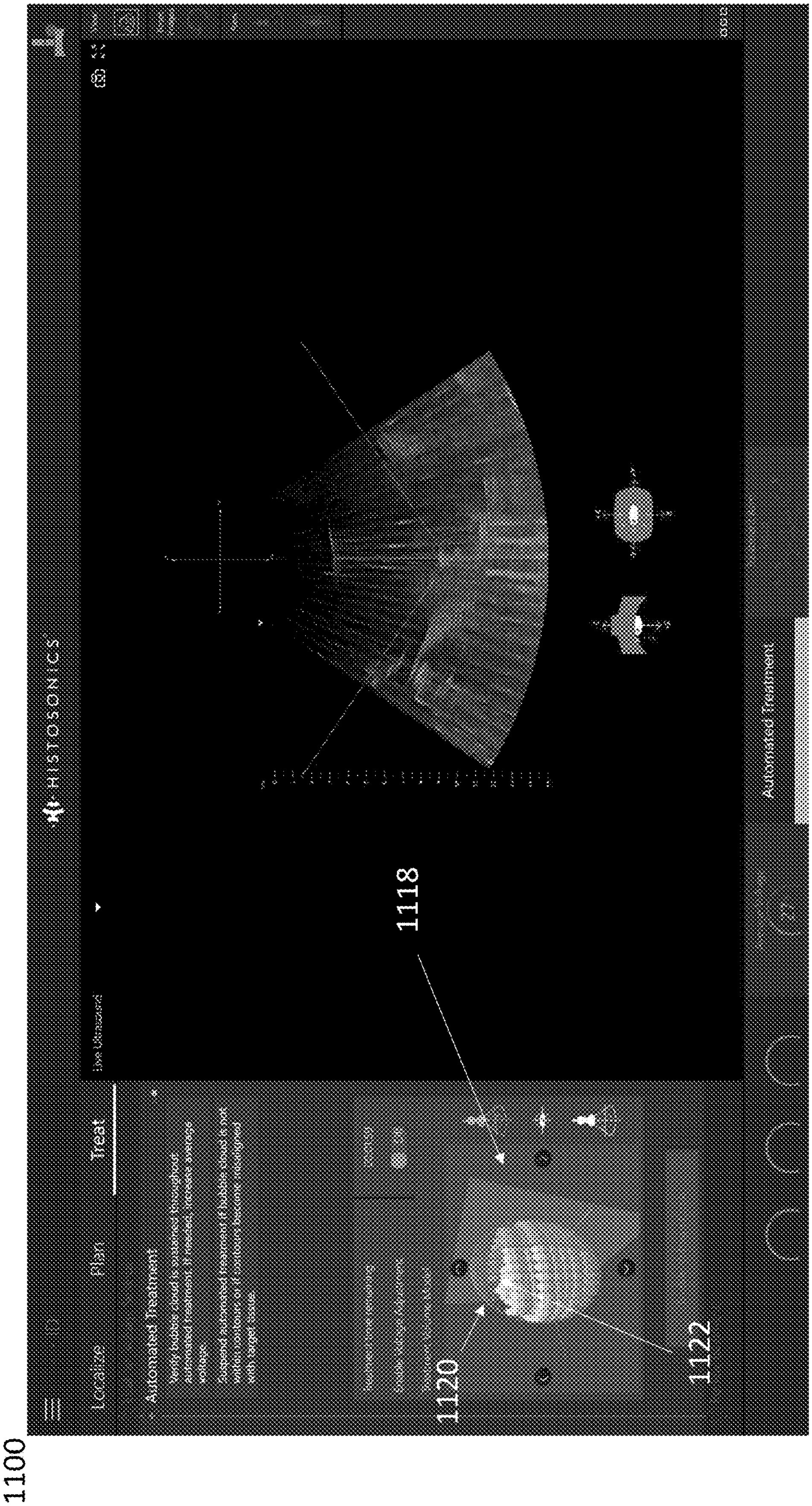
Figure 49G:
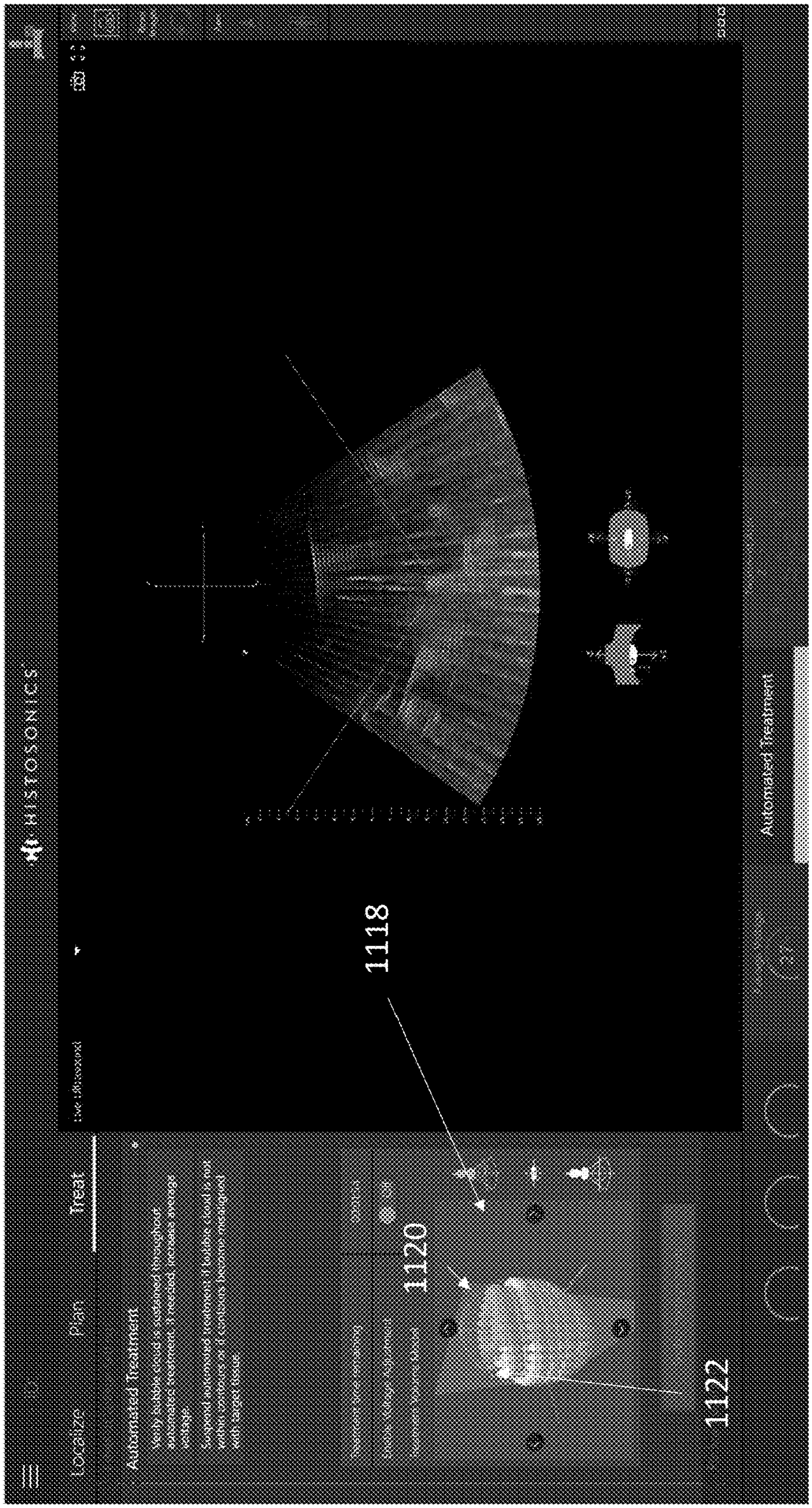

FIG. 46 shows a perspective view of the volume to be treated 1120. FIG. 47 shows a top view of the volume to be treated 1120 while FIG. 48 shows a profile view of the volume to be treated. The displayed view of the volume to be treated can be changed by selection of one of the view selector buttons 1124. FIG. 49A shows a perspective view of the progress of the treatment as energy is applied to successive focal locations. 1122 FIGS. 49B-49G, depict the continuation of the progress of the treatment as sequential focal locations 1122 are treated until each focal location 1122 of the entire volume to be treated 1120 is receives its therapy. Note that for FIGS. 49B-G the live fused image 1115 is not displayed, as application of therapy would appear if the image fusion process, described above, is skipped.

Figure 50:

When all focal locations 1122 have received treatment a yes at step 1022, the UI 1100 advances to the display seen in FIG. 50. At this point, the user is directed at step 1026 to deactivate the voltage knob 32. After deactivation of the voltage knob 32, the user is directed at step 1028 to utilize robotic arm 14 to move the ultrasound probe 22, and to visualize the entire volume to be treated in ultrasound images. This may be accomplished using the freehand buttons 44 and manually moving the treatment head 20 or by using the space mouse 36. The user may optionally add comments in the comment field 1126, at step 1030 or simply select the end treatment session button 1130 at step 1132 and remove the treatment head 20 from the coupling medium at step 1132.

The treatment is now complete, but a record of the steps undertaken, the ultrasound images acquired during the procedure, as well as the fusion achieved are stored in memory for future analysis.

If future treatments are planned, the system may be configured such that treatment parameters may be recalled including, but not limited to robotic arm pose, position and treatment head and therapy transducer focus location, bubble cloud offset, voltage thresholds/requirements, target depth and plan/treatment location and parameters. These parameters may be useful, for example, when additional treatments are performed within the same tumor or lesion and/or a one or more additional treatment plans are intended overlapping and/or in proximity to the first plan/treatment.

As an example, when an adjacent treatment may be performed, the Histotripsy system can be configured to recall recent treatment/plan parameters and be automatically positioned (treatment head and robotic arm pose) at the start, endpoint or in any treatment point (focal location or time-based) therebetween.

In another example, the histotripsy system is configured to allow the users to recall/move-to the robot pose used in the previous treatment(s). This will position the treatment head in the same position as before assuming the patient and therapy cart didn't move after the prior treatment(s). The user would need to recall the specifics of the previous treatment plan(s) (XYZ diameter and margin) though, and then decide how to size and position the subsequent treatment plan(s). As previously disclosed, in some configurations, the system may store this information for recall.

In yet another example, the histotripsy system may be configured to display the previous treatment(s) plan contours and plan overlays. Having the previous treatment plan contours shown on the screen along with recall/move-to functionality (Option 1) will give the user a visual aid to plan for overlapping their next treatment. This option again relies on the user to determine the best next treatment plan considering overlap of the previous treatment plan(s) as well as tumor coverage considerations.

In an alternate example, the histotripsy system may be configured to plan all overlapping treatments prior to first therapy delivery. If the user can identify and mark tumors to be treated in 3D space, then the histotripsy system may create and display a recommended multi-treatment plan for the user to review. In some versions of this example, pre and peri-procedural CBCT may be used to enable this capability.

Figure 52:
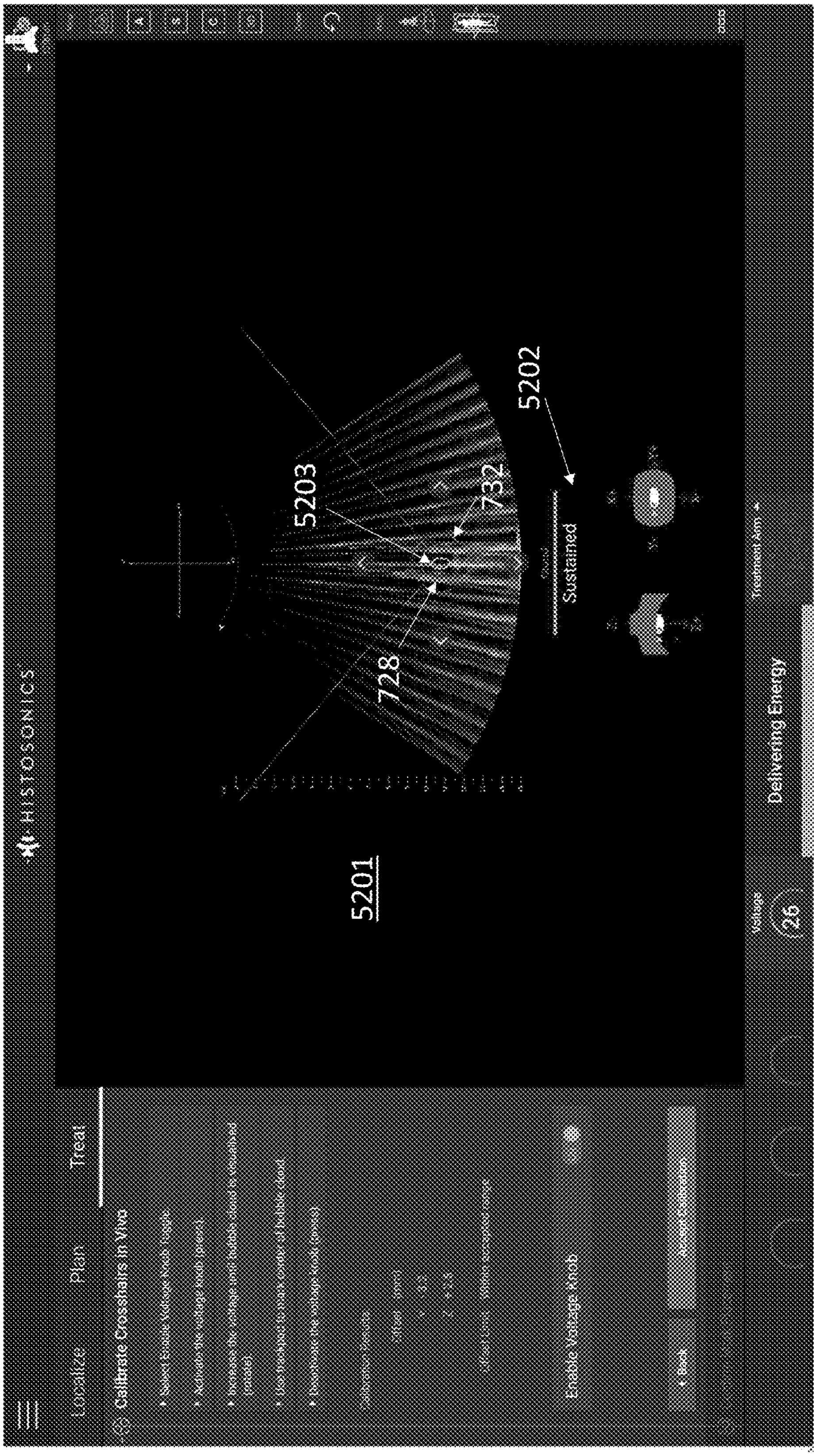
FIG. 52 is a UI and workflow specific to detecting sustained cavitation.

In another embodiment, shown in FIG. 52, the UI 1100 may include graphics 5201 denoting the detection of cavitation for the user, in addition to "seeing or hearing" the bubble cloud. This may be presented to the user in various ways and locations on the display or UI. In one example, the UI may display a cloud or cavitation status 5202 which can include words such as "cavitation detected" or "cloud detected" to convey the cloud or cavitation status to the user. In a different example, the graphics may show an indicator 5203 for cavitation detection ("cloud") and display a colored indicator for different statuses of cavitation including when the cavitation is "detected" or "sustained". In the example of FIG. 52, the indicator 5203 is color coded to show "sustained" cavitation with matches the color coding of cavitation status 5202 on the graphics of the UI. The indicator 5203 can comprise, for example, an oval or round shape configured to outline or highlight the extent of the cavitation, and can be presented alongside the treatment contour 728 and the margin 732. In some embodiments, the color coding and/or indicator can be different for "detected" cavitation vs. "sustained" cavitation. In another example, the indicator may show real-time feedback (total and/or by transducer channel if displaying a graphic of transducer face and pulsing channels). In these examples, the system and UI may enable this feature for users across all work-flow steps (system check through treatment) and/or in alternative configurations, may selectively disable cavitation detection in the use case that it's preferred for users to visually detect the cloud (as an example, during bubble cloud calibration).

Figure 53:
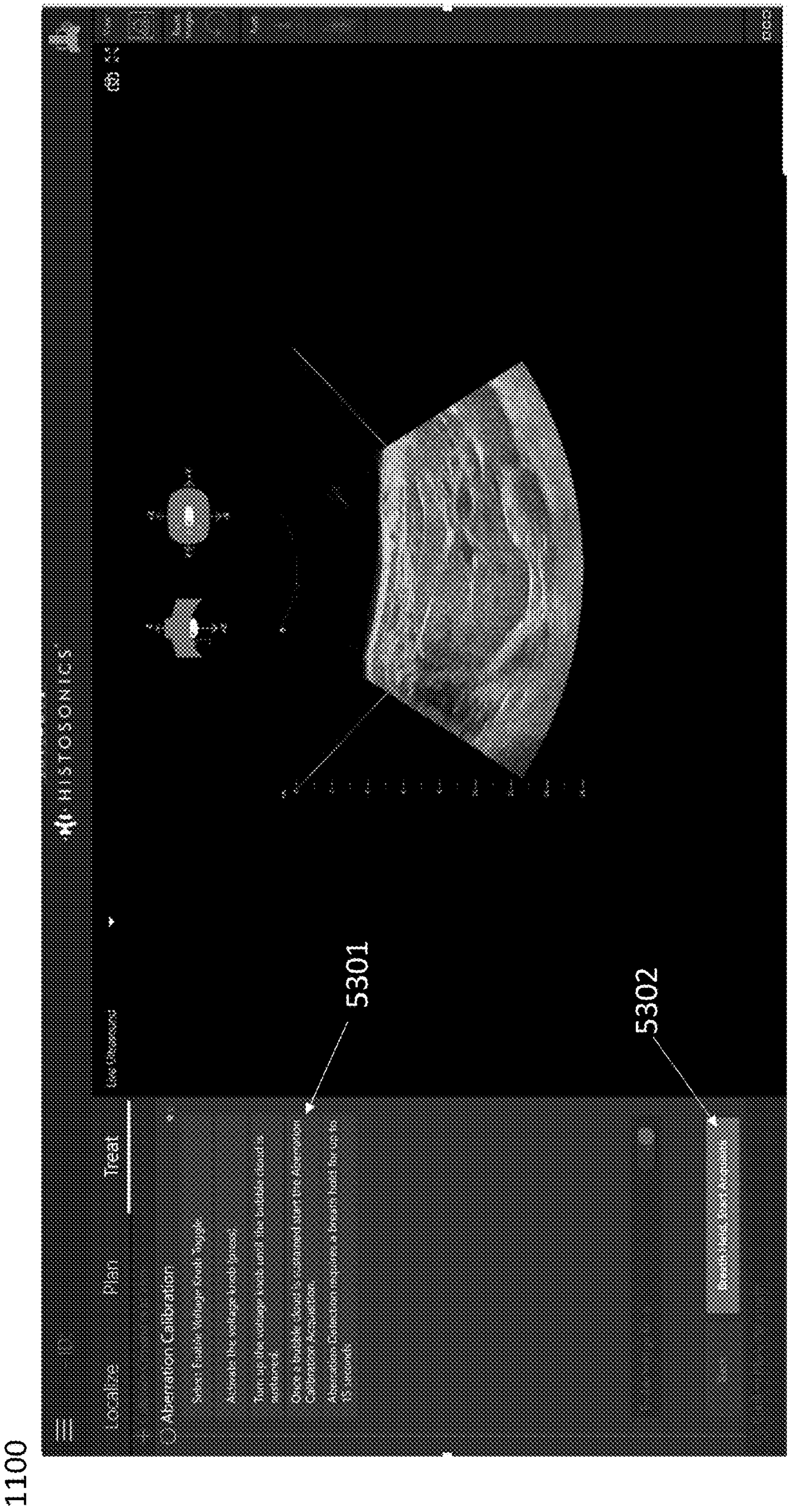
FIG. 53 is a UI and workflow for initiating acquisition of an aberration correction calibration.

Further as a part of cavitation detection described above, in FIG. 53 the UI 1100 may also comprise work-flow steps, screens and/or graphics for guiding the user through one or more steps to acquire receive (e.g., detection) data to enable aberration correction. At workflow step 5301 shown on UI 1100, sustained bubble cloud cavitation has been detected by the system (and shown to the user with UI 1100 in FIG. 52). Breath Held, Start Acquisition button 5302 can be enabled by the user to start enable aberration correction. This process can adjust transmission of the ultrasound waveforms based on obstructions or varying speeds of sounds in tissue to ensure that the cavitation is positioned at the desired position within the anatomy (e.g., within the treatment volume).

Upon completion of treatment, various forms of procedure and treatment reports may be provided. Reports may comprise various forms of data, including patient and treatment contextual information (disease type, size, stage, location, etc.), plan parameters (size, location, target and margin contour dimensions, plan depth, plan position in context to target tissue/tumor, etc.), energy settings (thresholds and/or voltage settings across plan points, average voltage, etc.), treatment details (time, etc.). This may further comprise screenshots from the UI, video recordings of the UI or procedure. The information/data may also include any that may have been included and/or utilized for pre-procedure simulation and/or the patient registration process described earlier. The various reports may be exportable to electronic health records or databases, and/or to local networks, media and/or other devices.

Figure 56:
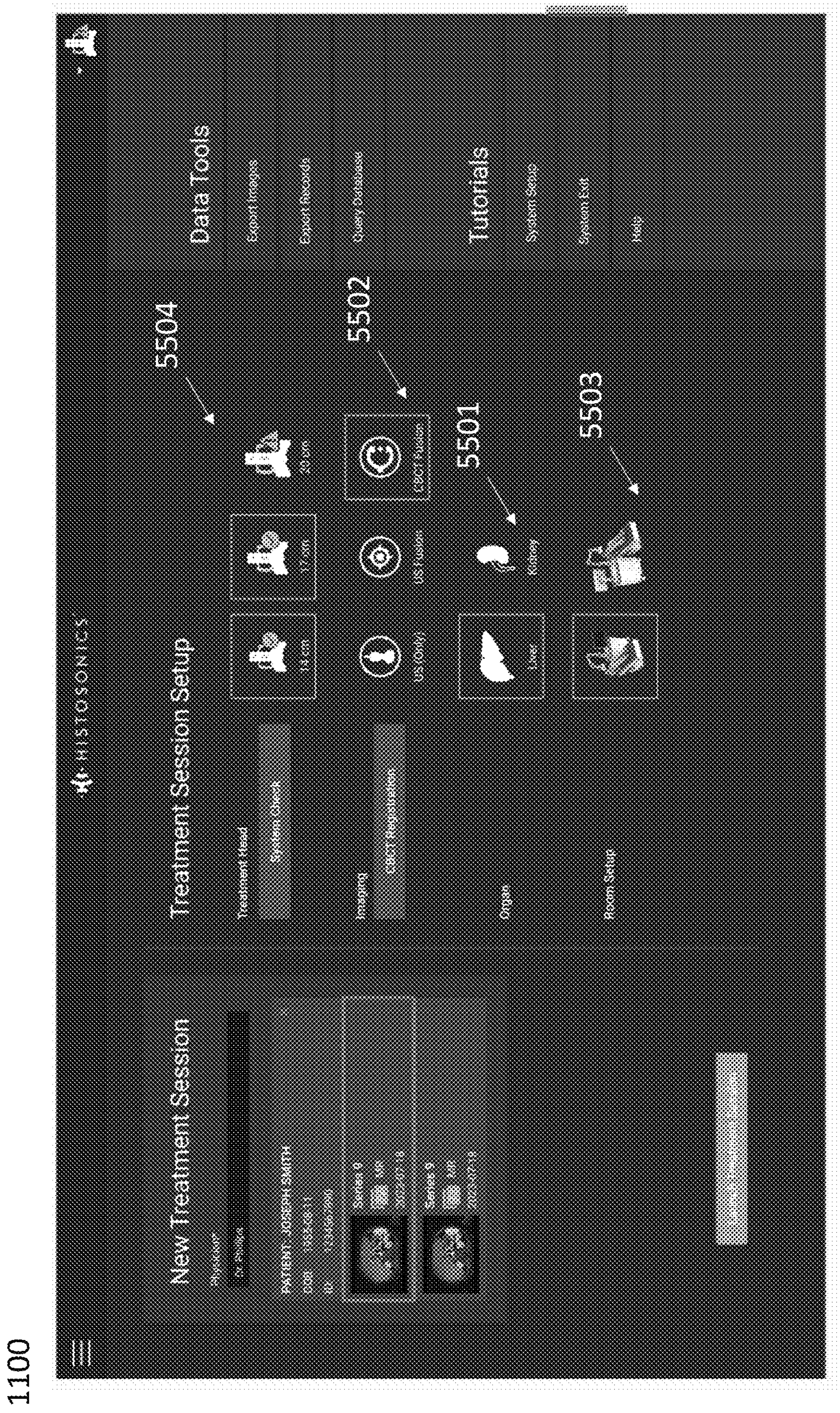
FIG. 56 is a UI that customizes treatment and setup workflows based on the treatment head type, imaging type, target organ, and/or room setup.

In some examples, referring to FIG. 56, the system and UI 1100 may be configured to be modular and enable users to select one or more work-flows based the procedure application, indication and/or anatomical location 5501 (e.g., abdominal, liver, kidney, pancreas, spleen, upper or lower GI, cardiothoracic, lung, breast, thyroid, head and neck, neuro/cranial, spine, etc.), based on desired imaging 5502 (e.g., ultrasound only, fusion, CBCT, etc.), based on room setup 5503, and/or based on which treatment head 5504 is selected, and/or allow skipping specific work-flow steps if they've already been completed within an allowed time period (e.g., system check).

Schematic Architecture

Figure 51:
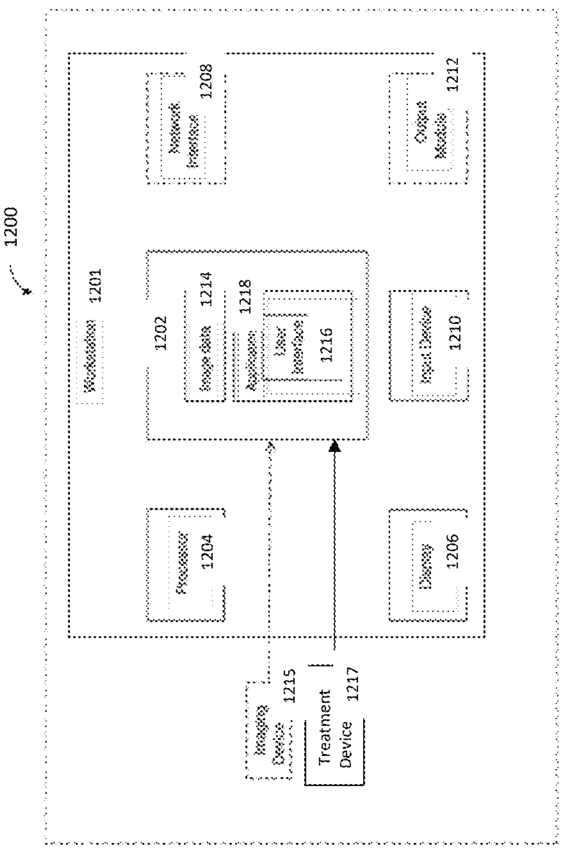
FIG. 51 is a schematic view of a histotripsy system in accordance with the disclosure.

Reference is now made to FIG. 51, which is a schematic diagram of a Histotripsy system 1200 configured for use with the methods of the disclosure including the methods 400 and 600. System 1200 may include a workstation 1201 (a computing device). The workstation 1001, as described above may be housed in the cart 12 and is connected to an ultrasonic imaging device 1015 (e.g., the imaging probe 22) and an ultrasonic treatment device (e.g., therapy transducer 18). In some embodiments, the system may be connected to an X-ray based imaging system, including a cone beam CT. Workstation 1001 may include a memory 1202, a processor 1204, a display 1206 (e.g., display 24 depicting UI 200, 500, 700, 1100) and an input device 1210. Processor or hardware processor 1204 may include one or more hardware processors. Workstation 1201 may optionally include an input/output module 1212 and a network interface 1208. In some embodiments, this may include streaming and/or connectivity to enable remote access to the system for query, retrieval, and/or receival of log or configuration files for service/support and/or for maintaining software or embedded solutions for the system and/or one or more subsystems (generator, robotic arm and control system, etc.). Memory 1202 may store an application 1218 and image data 1214. Application 1218 may include instructions executable by processor 1204 for executing the methods of the disclosure including the methods 50, 100, 400, 600, and 1000.

Application 1218 may further include a user interface 1216 (e.g., UI 200, 500, 700, 1100). Image data may include the pre-procedure CT and MRI scans or other images, ultrasound image data, and 2D and 3D reconstructions derived from the ultrasound image data, including multi-modal computer vision and fusion models. In some embodiments, including when connected to a cone beam CT, the UI may include graphics and instructions for guiding the user through how to set up, import, register, and navigate to the desired target. Processor 1204 may be coupled with memory 1202, display 1206, input device 1210, output module 1212, network interface 1208 and ultrasound imaging device 1215. Workstation 1201 may be a stationary computing device, such as a personal computer, or a portable computing device such as a tablet computer. Workstation 1201 may embed a plurality of computer devices.

Figure 54:
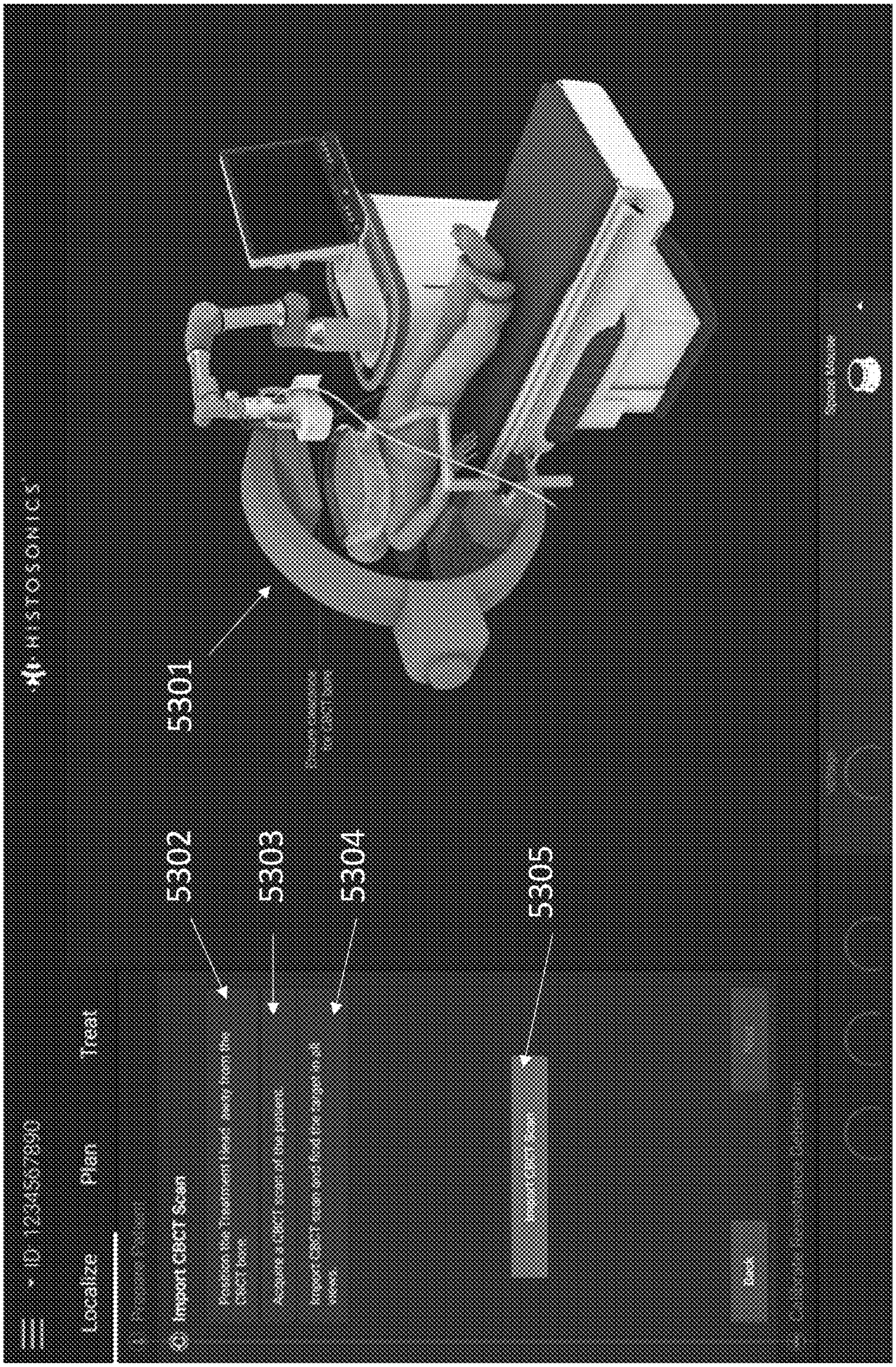
FIGS. 54 and 55A-55B illustrate workflows and UIs for guiding a user through the acquisition of CBCT images of a target tissue.

For example, FIG. 54 shows a UI 1100 including a workflow for positioning a CBCT machine 5301 around a patient to obtain CT images of the patient and/or target tissue. The UI can include workflow steps/user inputs 5302-5305 which can include positioning the treatment head of the histotripsy system away from the CBCT bore (5302), acquiring CBCT scan(s) of the patient (5303), importing the scans and identifying the target tissue (5304-5305).

Figure 55A:
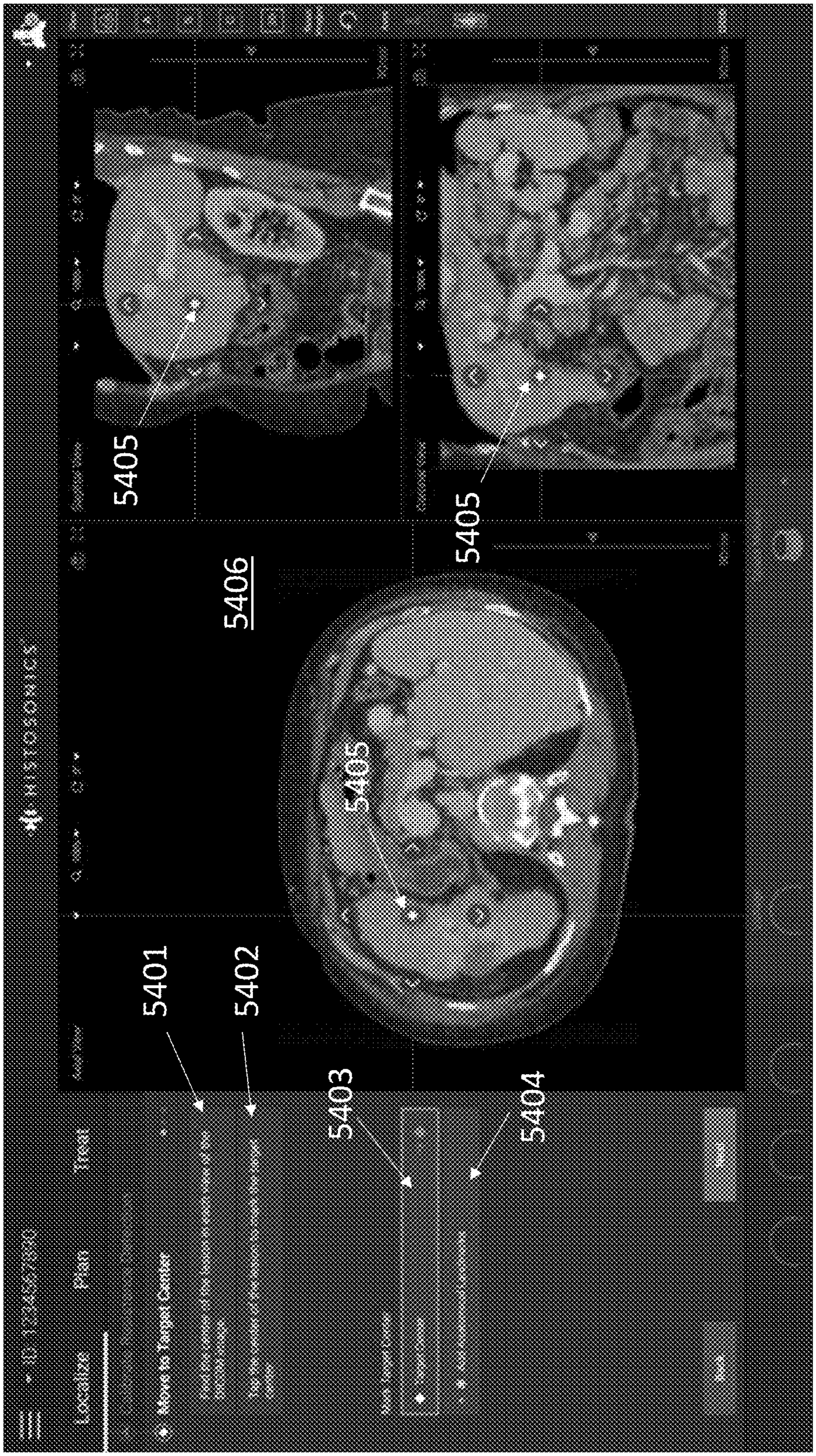

In FIG. 55A, workflow steps 5401-5402 guide the user to identify the center of a target lesion in each view of the imported CT images with a target center as shown in workflow step 5403. The target center 5405 is shown on each of the CT images 5406 as positioned by the user. The user can optionally add anatomical landmarks to the images as shown in workflow step 5404.

Figure 55B:
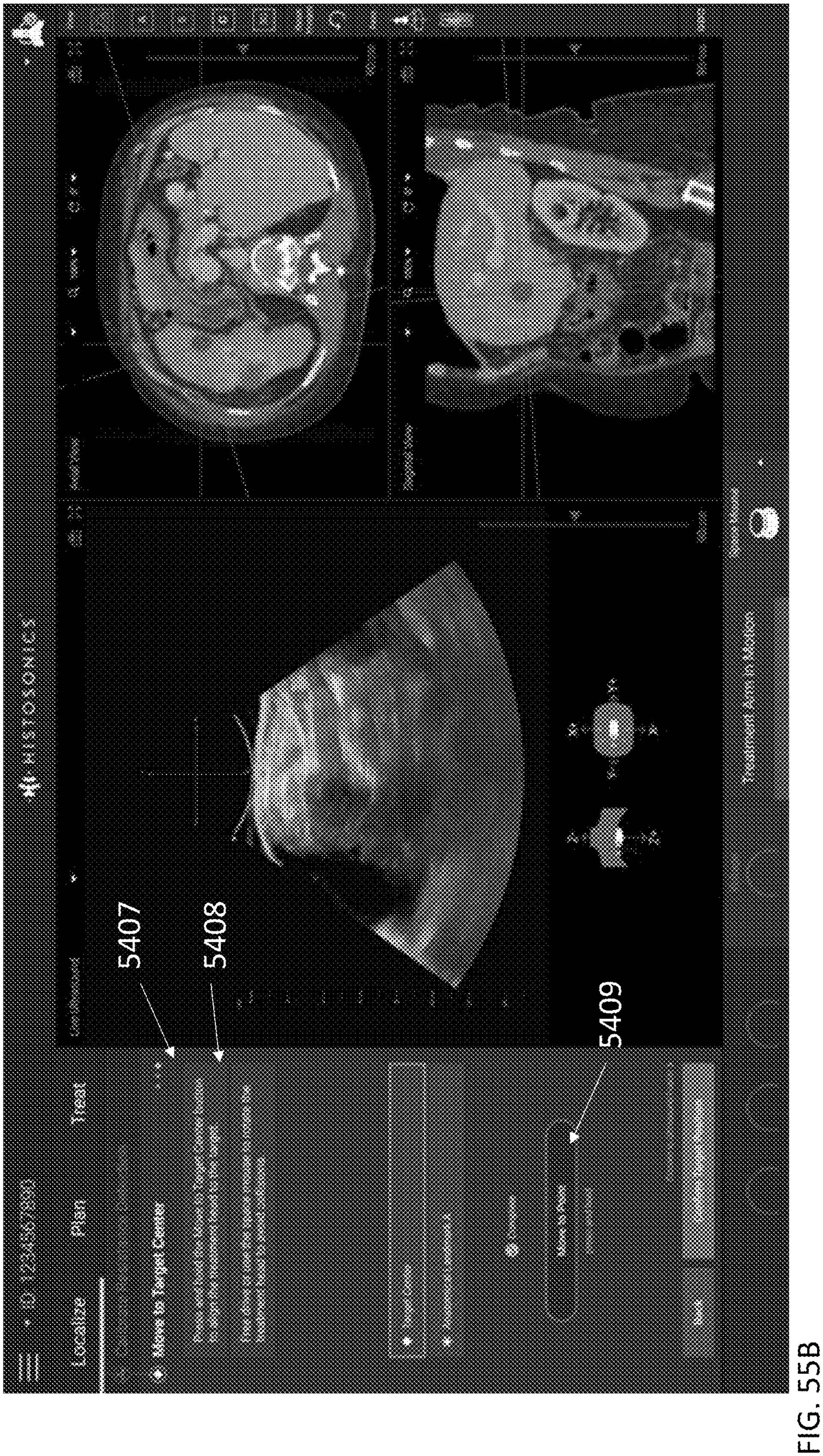

In FIG. 55B, workflow steps 5407-5408 guide the user to move the treatment head to align with the target center identified in the previous UI diagram. The user can hold "move to point" or "move to center" button 5409 to align the treatment head to the target center. Optionally, the user can manipulate the space mouse (or hardware input/joystick/mouse) to free drive the treatment head for positioning if it is required to avoid obstructions or collisions (e.g., with the patient or coupling container).

Memory 1202 may include any non-transitory computer-readable storage media for storing data and/or software including instructions that are executable by processor 1204 and which control the operation of workstation 1201 and, in some embodiments, may also control the operation of ultrasound imaging device 1215 and the ultrasound treatment device 1217. In an embodiment, memory 1202 may include one or more storage devices such as solid-state storage devices, e.g., flash memory chips. Alternatively, or in addition to the one or more solid-state storage devices, memory 1202 may include one or more mass storage devices connected to the processor 1204 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1204. That is, computer readable storage media may include non-transitory, volatile, and non-volatile, removable, and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1201.

Application 1218 may, when executed by processor 1204, cause display 1206 to present user interface 1216. User interface 1216 may be configured to present to the user a variety screens including any of FIGS. 4-13, 15, 17-22, 24-32, 34-40, and 42-50.

Network interface 1208 may be configured to connect to a network such as a local area network (LAN) consisting of a wired network and/or a wireless network, a wide area network (WAN), a wireless mobile network, a Bluetooth network, and/or the Internet. Network interface 1208 may be used to connect between workstation 1201 and imaging device 1215 or the treatment device 1217. Network interface 1208 may be also used to receive image data 1214. Input device 1210 may be any device by which a user may interact with workstation 1201, such as, for example, a mouse, keyboard, foot pedal, touch screen, and/or voice interface. Output module 1212 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

While detailed embodiments are disclosed herein, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the disclosure in virtually any appropriately detailed structure. Those skilled in the art will envision other modifications within the scope and spirit of the claims appended hereto.

We claim:

1. A histotripsy system comprising:

an ultrasound imaging system;

an ultrasound therapy transducer coupled to the ultrasound imaging system;

a robotic arm configured to position the ultrasound imaging system and the ultrasound therapy transducer with respect to a patient and a treatment location;

a display operably connected to the ultrasound imaging system;

a memory, storing thereon instructions that when executed by a processor operably connected to the memory:

receive real-time ultrasound images from the ultrasound imaging system, present the live ultrasound images on a user interface in the display;

identify a target;

receive via the user interface an input to alter a shape of a target contour around a treatment volume in the live ultrasound images;

present a target contour line representative of the target contour on the ultrasound images in the user interface;

receive via the user interface an input of a size of a margin around the target area;

present a margin contour line representative of the margin contour on the ultrasound images in the user interface;

determine survey points at locations where X, Y, and Z axes bisect the margin line in an XZ plane and a YZ plane;

receive an input to drive the ultrasound therapy transducer to a location where a focal location of the ultrasound therapy transducer is at one of the survey points; and determine whether resistance to movement of the ultrasound therapy transducer exceeds a threshold.

2. The histotripsy system of claim 1, wherein receipt via the user interface of an input to alter the shape of the treatment contour around a treatment volume occurs in live ultrasound images in the XZ plane and in the YZ plane.

3. The histotripsy system of claim 1, wherein the input to drive the ultrasound therapy transducer is received via the user interface in the display.

4. The histotripsy system of claim 1, wherein the input to drive the ultrasound therapy transducer is received for each survey point.

5. The histotripsy system of claim 4, wherein upon determination that the resistance to movement of the ultrasound therapy transducer in driving to reach all of the survey points does not exceed a threshold, a planned therapy is accepted and stored in the memory.

6. The histotripsy system of claim 4, wherein upon determination that the resistance to movement of the ultrasound therapy transducer in driving to reach any of the survey points exceeds a threshold, the instructions stored in memory and executed by the processor cause the user interface to present mitigation instructions.

7. The histotripsy system of claim 1, further comprising presenting a representation of the contour line and the survey points in a separate field in the user interface.

8. The histotripsy system of claim 7, wherein the input to drive the therapy transducer is received via the representation of the contour line and survey points in the separate field in the user interface.

9. The histotripsy system of claim 7, further comprising an indicator depicted on the survey point of the representation in the separate field on the user interface, wherein the indicator is depicted upon movement of the therapy transducer to a location at which the focal point coincides with the survey point.

10. The histotripsy system of claim 1, wherein the instructions when executed by the processor receive in input of a location of an intersection of a muscle layer and a fat layer in the live ultrasound images.

11. The histotripsy system of claim 1, wherein the instructions when executed by the processor cause activation of knobs which when manipulated adjust a parameter displayed in an indicator on the user interface.

12. The histotripsy system of claim 11, wherein the knobs adjust the contour along the X, Y, and Z axes.

13. The histotripsy system of claim 11, wherein the knobs adjust the size of the margin around the contour.

14. The histotripsy system of claim 11, wherein the knobs adjust the focal location of the therapy transducer.

15. A method of planning a histotripsy procedure comprising:

displaying live ultrasound images on a user interface;

moving an ultrasound assembly to a mark on a patient from which a treatment area within the patient can be observed in the live ultrasound images;

presenting a contour line around a treatment volume in the live ultrasound images on the user interface;

adjusting the contour line in the live ultrasound images;

identifying survey points where X, Y, and Z axes intersect the contour line in XZ plane and the YZ plane;

displaying a margin around the contour line;

displaying a focal point of a therapy transducer, wherein the therapy transducer is a component of the ultrasound assembly;

driving the ultrasound assembly such that the focal point of the therapy transducer coincides with at least one of survey points; and detecting a resistance to movement of the ultrasound assembly as it moves to reach the at least one survey point.

16. The method of claim 15, further comprising comparing the resistance to movement to a threshold.

17. The method of claim 15, further comprising altering a shape of the contour line around a treatment area in the live ultrasound images in the XZ plane and in the YZ plane.

18. The method of claim 15, wherein the ultrasound assembly is robotically driven to each survey point.

19. The method of claim 18, wherein upon determination that the resistance to movement of the therapy transducer in driving to reach each of the survey points does not exceed a threshold, a planned therapy is accepted and stored in a memory.

20. The method of claim 19, further comprising receiving in indication of a location of an intersection of a muscle layer and a fat layer in the live ultrasound images.

* * * * *